(12) United States Patent
Rodrigo et al.

(10) Patent No.: US 12,134,633 B2
(45) Date of Patent: *Nov. 5, 2024

(54) SEPARATION MATRIX

(71) Applicant: Cytiva BioProcess R&D AB, Uppsala (SE)

(72) Inventors: Gustav José Rodrigo, Uppsala (SE); Tomas Bjorkman, Uppsala (SE); Mats Ander, Uppsala (SE); Jesper Ulf Hansson, Uppsala (SE)

(73) Assignee: Cytiva BioProcess R&D AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/298,857

(22) Filed: Apr. 11, 2023

(65) Prior Publication Data

US 2023/0279047 A1 Sep. 7, 2023

Related U.S. Application Data

(63) Continuation of application No. 17/221,438, filed on Apr. 2, 2021, now Pat. No. 11,685,764, which is a continuation of application No. 16/893,574, filed on Jun. 5, 2020, now Pat. No. 10,995,113, which is a continuation of application No. 16/682,855, filed on Nov. 13, 2019, now Pat. No. 10,711,035, which is a continuation of application No. 16/096,952, filed as application No. PCT/EP2017/061164 on May 10, 2017, now Pat. No. 10,513,537, which is a continuation of application No. 15/282,367, filed on Sep. 30, 2016, now Pat. No. 10,654,887.

(30) Foreign Application Priority Data

May 11, 2016 (GB) .................................. 1608229
May 11, 2016 (GB) .................................. 1608232

(51) Int. Cl.

| | | |
|---|---|---|
| *C07K 1/22* | (2006.01) | |
| *B01D 15/38* | (2006.01) | |
| *B01J 20/24* | (2006.01) | |
| *B01J 20/28* | (2006.01) | |
| *B01J 20/286* | (2006.01) | |
| *B01J 20/32* | (2006.01) | |
| *C07K 14/31* | (2006.01) | |
| *C07K 16/00* | (2006.01) | |
| *C07K 16/06* | (2006.01) | |
| *C07K 17/10* | (2006.01) | |

(52) U.S. Cl.
CPC ............ *C07K 1/22* (2013.01); *B01D 15/3809* (2013.01); *B01J 20/24* (2013.01); *B01J 20/28016* (2013.01); *B01J 20/28078* (2013.01); *B01J 20/286* (2013.01); *B01J 20/3212* (2013.01); *B01J 20/3274* (2013.01); *C07K 14/31* (2013.01); *C07K 16/00* (2013.01); *C07K 16/065* (2013.01); *C07K 17/10* (2013.01)

(58) Field of Classification Search
CPC ....................................................... C07K 1/22
See application file for complete search history.

(56) References Cited

U.S. PATENT DOCUMENTS

| | | |
|---|---|---|
| 4,704,366 A | 11/1987 | Juarez-Salinas et al. |
| 4,708,714 A | 11/1987 | Larsson et al. |
| 4,801,687 A | 1/1989 | Ngo |
| 4,933,435 A | 6/1990 | Ngo |
| 5,011,686 A | 4/1991 | Pang |
| 5,084,398 A | 1/1992 | Huston et al. |
| 5,143,844 A | 9/1992 | Abrahmsen et al. |
| 5,476,786 A | 12/1995 | Huston |
| 5,831,012 A | 11/1998 | Nilsson et al. |
| 6,127,526 A | 10/2000 | Blank |
| 6,207,804 B1 | 3/2001 | Huston et al. |
| 6,296,804 B1 | 10/2001 | Chapman et al. |
| 6,399,750 B1 | 6/2002 | Johansson |
| 6,602,990 B1 | 8/2003 | Berg |
| 6,870,034 B2 | 3/2005 | Breece et al. |
| 7,220,356 B2 | 5/2007 | Thommes et al. |
| 7,396,467 B2 | 7/2008 | Berg et al. |
| 7,566,565 B2 | 7/2009 | Peters et al. |
| 7,709,209 B2 | 5/2010 | Hober et al. |
| 7,714,111 B2 | 5/2010 | Sun et al. |
| 7,820,799 B2 | 10/2010 | Godavarti et al. |

(Continued)

FOREIGN PATENT DOCUMENTS

| | | |
|---|---|---|
| EP | 2202310 A2 | 6/2010 |
| EP | 2412809 A1 | 2/2012 |

(Continued)

OTHER PUBLICATIONS

U.S. Non-Final Office Action from corresponding U.S. Appl. No. 17/114,773, mailed Jul. 6, 2023, 10 pages.

(Continued)

*Primary Examiner* — Albert M Navarro
(74) *Attorney, Agent, or Firm* — Eversheds-Sutherland (US) LLP

(57) ABSTRACT

The invention relates to a separation matrix comprising at least 11 mg/ml Fc-binding ligands covalently coupled to a porous support, wherein:

a) the ligands comprise multimers of alkali-stabilized Protein A domains, and b) the porous support comprises cross-linked polymer particles having a volume-weighted median diameter (d50,v) of 56-70 micrometers and a dry solids weight of 55-80 mg/ml.

38 Claims, 6 Drawing Sheets

Specification includes a Sequence Listing.

(56) References Cited

U.S. PATENT DOCUMENTS

| | | |
|---|---|---|
| 7,834,158 B2 | 11/2010 | Hober |
| 7,834,162 B2 | 11/2010 | Zhou |
| 7,884,264 B2 | 2/2011 | Dickey et al. |
| 7,901,581 B2 | 3/2011 | Bryntesson et al. |
| 8,080,246 B2 | 12/2011 | Lin et al. |
| 8,084,032 B2 | 12/2011 | Yumioka et al. |
| 8,182,696 B2 | 5/2012 | Theoleyre et al. |
| 8,183,207 B2 | 5/2012 | Lin et al. |
| 8,198,404 B2 | 6/2012 | Hober |
| 8,263,750 B2 | 9/2012 | Shukla et al. |
| 8,282,914 B2 | 10/2012 | Chou et al. |
| 8,329,860 B2 | 12/2012 | Hall et al. |
| 8,329,869 B2 | 12/2012 | Kraynov et al. |
| 8,354,510 B2 | 1/2013 | Hober et al. |
| 8,377,448 B2 | 2/2013 | Smith et al. |
| 8,586,713 B2 | 11/2013 | Davis et al. |
| 8,592,555 B2 | 11/2013 | Spector |
| 8,617,881 B2 | 12/2013 | Coljee et al. |
| 8,674,073 B2 | 3/2014 | Majima et al. |
| 8,728,479 B2 | 5/2014 | Greene et al. |
| 8,754,196 B2 | 6/2014 | Spector |
| 8,772,447 B2 | 7/2014 | Hall et al. |
| 8,822,642 B2 | 9/2014 | Levin et al. |
| 8,853,371 B2 | 10/2014 | Alfonso et al. |
| 8,859,726 B2 | 10/2014 | Bjorkman et al. |
| 8,883,134 B2 | 11/2014 | Cho et al. |
| 8,895,706 B2 | 11/2014 | Spector et al. |
| 9,018,305 B2 | 4/2015 | Spector et al. |
| 9,024,000 B2 | 5/2015 | Jeon et al. |
| 9,040,661 B2 | 5/2015 | Nakamura et al. |
| 9,051,375 B2 | 6/2015 | Li et al. |
| 9,073,970 B2 | 7/2015 | Muller-Spath et al. |
| 9,149,738 B2 | 10/2015 | Skudas |
| 9,156,892 B2 | 10/2015 | Hober |
| 9,162,161 B2 | 10/2015 | Tamori et al. |
| 9,187,555 B2 | 11/2015 | Bjorkman et al. |
| 9,266,939 B2 | 2/2016 | Crine et al. |
| 9,284,347 B2 | 3/2016 | Eckermann et al. |
| 9,290,549 B2 | 3/2016 | Hall et al. |
| 9,290,573 B2 | 3/2016 | Cong et al. |
| 9,296,791 B2 | 3/2016 | Hober et al. |
| 9,382,305 B2 | 7/2016 | Wilmen et al. |
| 9,481,730 B2 | 11/2016 | Bruenker et al. |
| 9,493,529 B2 | 11/2016 | Blanche et al. |
| 9,499,608 B2 | 11/2016 | Chen et al. |
| 9,517,264 B2 | 12/2016 | Fachini et al. |
| 9,534,023 B2 | 1/2017 | Hober |
| 9,540,442 B2 | 1/2017 | Tsurushita et al. |
| 9,556,258 B2 | 1/2017 | Nti-Gyabaah et al. |
| 9,573,989 B2 | 2/2017 | Watzig et al. |
| 9,587,235 B2 | 3/2017 | Buechler et al. |
| 9,637,541 B2 | 5/2017 | Kim et al. |
| 9,637,557 B2 | 5/2017 | Scheer et al. |
| 9,650,442 B2 | 5/2017 | Hosse et al. |
| 9,662,373 B2 | 5/2017 | Cload et al. |
| 9,676,871 B2 | 6/2017 | Strop et al. |
| 9,688,978 B2 | 6/2017 | Buechler et al. |
| 9,695,233 B2 | 7/2017 | Duerr et al. |
| 9,708,405 B2 | 7/2017 | Liu et al. |
| 9,714,292 B2 | 7/2017 | Auer et al. |
| 9,920,098 B2 | 3/2018 | Yoshida et al. |
| 10,065,995 B2 | 9/2018 | Yoshida et al. |
| 10,513,537 B2 | 12/2019 | Rodrigo |
| 10,654,887 B2 | 5/2020 | Rodrigo |
| 10,703,774 B2 | 7/2020 | Forss et al. |
| 10,711,035 B2 | 7/2020 | Rodrigo |
| 10,730,908 B2 | 8/2020 | Forss |
| 10,808,042 B2 | 10/2020 | Haupts |
| 10,889,615 B2 | 1/2021 | Rodrigo |
| 10,918,971 B2 | 2/2021 | Hober |
| 10,995,113 B2 | 5/2021 | Rodrigo |
| 11,136,359 B2 | 10/2021 | Rodrigo et al. |
| 11,623,941 B2 | 4/2023 | Forss |
| 11,685,764 B2 * | 6/2023 | Rodrigo ............... C07K 17/10 530/387.1 |
| 2005/0097625 A1 | 5/2005 | Meade et al. |
| 2005/0143566 A1 | 6/2005 | Hober |
| 2006/0194955 A1 | 8/2006 | Hober et al. |
| 2007/0207500 A1 | 9/2007 | Bian et al. |
| 2007/0243626 A1 | 10/2007 | Windeyer et al. |
| 2008/0069739 A1 | 3/2008 | Ludwig |
| 2008/0167450 A1 | 7/2008 | Pan |
| 2008/0230478 A1 | 9/2008 | Johansson et al. |
| 2010/0221844 A1 | 9/2010 | Bian et al. |
| 2010/0256338 A1 | 10/2010 | Brinkmann et al. |
| 2010/0267932 A1 | 10/2010 | Eon-Duval et al. |
| 2011/0117605 A1 | 5/2011 | Tolstrup et al. |
| 2011/0144311 A1 | 6/2011 | Chmielowski et al. |
| 2012/0071637 A1 | 3/2012 | Ambrosius et al. |
| 2012/0091063 A1 | 4/2012 | Bangtsson et al. |
| 2012/0148390 A1 | 6/2012 | Hsu et al. |
| 2012/0149875 A1 | 6/2012 | Johansson et al. |
| 2012/0208234 A1 | 8/2012 | Yoshida et al. |
| 2012/0238730 A1 | 9/2012 | Dong et al. |
| 2012/0263722 A1 | 10/2012 | Ghayur et al. |
| 2012/0283416 A1 | 11/2012 | Frauenschuh et al. |
| 2013/0096276 A1 | 4/2013 | Yoshida et al. |
| 2013/0096284 A1 | 4/2013 | Ishihara |
| 2013/0197197 A1 | 8/2013 | Eckermann et al. |
| 2013/0274451 A1 | 10/2013 | Bjorkman et al. |
| 2014/0018525 A1 | 1/2014 | Goklen et al. |
| 2014/0031522 A1 | 1/2014 | Li et al. |
| 2014/0094593 A1 | 4/2014 | Frauenschuh |
| 2014/0100356 A1 | 4/2014 | Yoshida et al. |
| 2014/0107315 A1 | 4/2014 | Yoshida et al. |
| 2014/0148390 A1 | 5/2014 | Haupts et al. |
| 2014/0154270 A1 | 6/2014 | Wang et al. |
| 2014/0155565 A1 | 6/2014 | Joehnck et al. |
| 2014/0228548 A1 | 8/2014 | Galperina |
| 2014/0242624 A1 | 8/2014 | Valliere-Douglass et al. |
| 2014/0251911 A1 | 9/2014 | Skudas |
| 2014/0303356 A1 | 10/2014 | Gramer et al. |
| 2014/0329995 A1 | 11/2014 | Johansson et al. |
| 2015/0009380 A1 | 1/2015 | Kobayashi et al. |
| 2015/0044209 A1 | 2/2015 | Brodt et al. |
| 2015/0080554 A1 | 3/2015 | Ander et al. |
| 2015/0093800 A1 | 4/2015 | Mahajan et al. |
| 2015/0133636 A1 | 5/2015 | Xenopoulos et al. |
| 2015/0137992 A1 | 5/2015 | Potyrailo et al. |
| 2015/0140683 A1 | 5/2015 | Rueger et al. |
| 2015/0209445 A1 | 7/2015 | Maderna et al. |
| 2015/0210749 A1 | 7/2015 | Combs et al. |
| 2015/0218250 A1 | 8/2015 | Auer et al. |
| 2015/0368352 A1 | 12/2015 | Liu |
| 2016/0024147 A1 | 1/2016 | Tustian et al. |
| 2016/0053025 A1 | 1/2016 | Oh et al. |
| 2016/0083480 A1 | 3/2016 | Ng et al. |
| 2016/0090426 A1 | 3/2016 | Zhou et al. |
| 2016/0108084 A1 | 4/2016 | Gruber et al. |
| 2016/0145340 A1 | 5/2016 | Borges et al. |
| 2016/0152668 A1 | 6/2016 | Hober |
| 2016/0152725 A1 | 6/2016 | Cheung et al. |
| 2016/0158377 A1 | 6/2016 | Ackler et al. |
| 2016/0159855 A1 | 6/2016 | Rodrigo et al. |
| 2016/0159857 A1 | 6/2016 | Rodrigo et al. |
| 2016/0159929 A1 | 6/2016 | Lee et al. |
| 2016/0166634 A1 | 6/2016 | Caplan et al. |
| 2016/0200797 A1 | 7/2016 | Hall et al. |
| 2016/0237124 A1 | 8/2016 | Qian et al. |
| 2016/0251395 A1 | 9/2016 | Davis et al. |
| 2016/0272710 A1 | 9/2016 | Hilden et al. |
| 2016/0289335 A1 | 10/2016 | Weisser et al. |
| 2016/0296648 A1 | 10/2016 | Chevallier et al. |
| 2016/0304617 A1 | 10/2016 | Damle et al. |
| 2016/0310612 A1 | 10/2016 | Lyon et al. |
| 2016/0311853 A1 | 10/2016 | Geierstanger et al. |
| 2016/0340443 A1 | 11/2016 | Rossi et al. |
| 2016/0362474 A1 | 12/2016 | Wang et al. |
| 2016/0362500 A1 | 12/2016 | Knoetgen |
| 2017/0043033 A1 | 2/2017 | Strop et al. |
| 2017/0081412 A1 | 3/2017 | Newman et al. |
| 2017/0088596 A1 | 3/2017 | Scheer et al. |
| 2017/0096485 A1 | 4/2017 | Bacac et al. |
| 2017/0114141 A1 | 4/2017 | Amann et al. |

(56) References Cited

U.S. PATENT DOCUMENTS

| | | |
|---|---|---|
| 2017/0121282 A1 | 5/2017 | Geierstanger et al. |
| 2017/0152298 A1 | 6/2017 | Banerjee et al. |
| 2017/0165370 A1 | 6/2017 | Govindan et al. |
| 2017/0182179 A1 | 6/2017 | Ackler et al. |
| 2017/0204199 A1 | 7/2017 | Sanches et al. |
| 2017/0216452 A1 | 8/2017 | Ma et al. |
| 2017/0218051 A1 | 8/2017 | Gnauer et al. |
| 2017/0226172 A1 | 8/2017 | Mohammadi et al. |
| 2017/0233453 A1 | 8/2017 | Zheng et al. |
| 2017/0233490 A1 | 8/2017 | Bossenmaier et al. |
| 2017/0247417 A1 | 8/2017 | Chang et al. |
| 2017/0247467 A1 | 8/2017 | Amann et al. |
| 2017/0260265 A1 | 9/2017 | Duerr et al. |
| 2017/0260289 A1 | 9/2017 | Petersen et al. |
| 2017/0327534 A1 | 11/2017 | Rodrigo et al. |
| 2017/0334954 A1 | 11/2017 | Rodrigo et al. |
| 2019/0119318 A1 | 4/2019 | Rodrigo et al. |
| 2021/0147577 A1 | 5/2021 | Rodrigo |

FOREIGN PATENT DOCUMENTS

| | | | |
|---|---|---|---|
| EP | 2557157 | A1 | 2/2013 |
| EP | 2728000 | A1 | 5/2014 |
| EP | 3050902 | A1 | 8/2016 |
| EP | 3335789 | A1 | 6/2018 |
| IN | 201717016314 | A | 10/2017 |
| JP | 2500329 | B2 | 5/1996 |
| JP | 2000-500649 | A | 1/2000 |
| JP | 2006304633 | A | 11/2006 |
| JP | 2010081866 | A | 4/2010 |
| JP | 2016-079149 | A | 5/2016 |
| JP | 2016-079153 | A | 5/2016 |
| JP | 2017-037070 | A | 2/2017 |
| WO | 1988/009344 | A1 | 12/1988 |
| WO | 03/080655 | A1 | 10/2003 |
| WO | 2005/075507 | A1 | 8/2005 |
| WO | 2008/049106 | A2 | 4/2008 |
| WO | 2010081866 | A2 | 7/2010 |
| WO | 2011/107518 | A1 | 9/2011 |
| WO | 2011/118699 | A1 | 9/2011 |
| WO | 2012/074463 | A1 | 6/2012 |
| WO | 2012/083425 | A1 | 6/2012 |
| WO | 2012/086660 | A1 | 6/2012 |
| WO | 2012/087231 | A1 | 6/2012 |
| WO | 2012/133349 | A1 | 10/2012 |
| WO | 2013/033517 | A1 | 3/2013 |
| WO | 2013/075849 | A1 | 5/2013 |
| WO | 2013/081540 | A1 | 6/2013 |
| WO | 2013/109302 | A2 | 7/2013 |
| WO | 2013/147691 | A1 | 10/2013 |
| WO | 2014/046278 | A1 | 3/2014 |
| WO | 2014146350 | | 9/2014 |
| WO | 2014/159064 | A1 | 10/2014 |
| WO | 2014/192877 | A1 | 12/2014 |
| WO | 2015005859 | A1 | 1/2015 |
| WO | 2015005862 | | 1/2015 |
| WO | 2015/048330 | A2 | 4/2015 |
| WO | 2015046473 | A1 | 4/2015 |
| WO | 2015/166072 | A1 | 11/2015 |
| WO | 2016/030791 | A1 | 3/2016 |
| WO | 2016/079033 | A1 | 5/2016 |
| WO | 2016079034 | A1 | 5/2016 |
| WO | 2016/097300 | A1 | 6/2016 |
| WO | 2017/011342 | A1 | 1/2017 |
| WO | 2017/036805 | A1 | 3/2017 |
| WO | 2017/050889 | A1 | 3/2017 |
| WO | 2017194592 | A1 | 11/2017 |
| WO | 2017194594 | A1 | 11/2017 |

OTHER PUBLICATIONS

Order Granted Request for Ex Parte Reexamination in U.S. Appl. No. 90/015,234, mailed Jun. 23, 2023, 11 pages.

Berry et al., "Substitution of Cysseine for Selenocysteine in Type 1 Iodothyronine Deiodinase Reduces the Catalytic Efficiency of the Protein but Enhances its Translation," Endocrinology, 1992, 131(4):1848-1852.

International Search Report for PCT Application No. PCT/EP2017/061160, mailed Aug. 25, 2017, 5 pages.

European Office Action for EP Application No. 15797942.8 mailed Jun. 25, 2019 (4 pages).

Russian Office Action for RU Application No. 2017115345/10 mailed Apr. 2, 2019 (English translation, 19 pages).

Gasser et al., "Antibody Production with Yeasts and Filamentous Fungi" On the Road to Large Scale?, Biotechnol Lett, 2007, 29:201-212.

Nikolaeva et al., "New Approach for Determination of the Identity of the Combined Vaccines for Diphtheria, Tetanus and Pertussis Prophylaxis," The Siberian Medical Journal, 2011, 26(2), 6 pages.

Pakula et al., "Genetic Analysis of Protein Stability and Function," Annu. rev. Genet., 1989, 23:289-310.

Singapore Written Opinion and Search Report for SG Application No. 112017030353P mailed May 3, 2018 (11 pages).

International Search Report and Written Opinion for PCT Application No. PCT/EP2015/076642 mailed Apr. 20, 2016 (19 pages).

International Search Report and Written Opinion for PCT Application No. PCT/EP2017/061162 mailed Sep. 11, 2017 (24 pages).

Uhlen et al., "Complete Sequence of the Staphylococcal Gene Encoding Protein A", Journal of Biological Chemistry, vol. 259, No. 3, Feb. 10, 1984, pp. 1695-1702.

Hedhammar et al., "Protein Engineering Strategies for Selective Protein Purification," Chemical Engineering Technology, vol. 28, No. 11, 2005, pp. 1315-1325.

JP Office Action for JP Application No. 2017-525398 mailed Nov. 11, 2019 (8 pages, English translation).

International Search Report for PCT Application No. PCT/EP2017/061164, mailed Aug. 30, 2017, 5 pages.

International Search Report and Written Opinion for PCT Application No. PCT/EP2017/061158, mailed Jul. 13, 2017, 15 pages.

PCT International Search Report and Written Opinion for PCT Application No. PCT/EP2017/061159 mailed Aug. 1, 2017 (11 pages).

Bach et al., "Differential binding of heavy chain variable domain 3 antigen binding fragments to protein a chromatography resins," J Chromatography A, 2015, 1409: 60-69.

Australian Office Examination Report No. 1 for AU Application No. 2015348641 mailed Dec. 17, 2019, 12 pages.

O'Seaghdha et al., "*Staphylococcus aureus* protein A binding to von Willebrand factor A1 domain is mediated by conserved IgG binding regions," FEBS J, 2006, 273, pp. 4831-4841.

Pakiman et al., "Comparison of Binding Capacity and Affinity of Monoclonal Antibody towards Different Affinity Resins using High-throughput Chromatography Method," J Appl Sci, 2012, 12, 11, pp. 1136-1141.

Weidle et al., "The intriguing options of multispecific antibody formats for treatment of cancer," Cancer Genom. Proteom, 2013, 10, pp. 1-18.

International Search Report for PCT Application No. PCT/EP2015/076639, mailed Feb. 10, 2016 (12 pages).

International-type Search Report for ITS/SE2014/000256, mailed May 13, 2015 (5 pages).

Japanese Office Action for Japanese Application No. 2017-525398, mailed Nov. 19, 2019 (8 pages).

Berry, J.D. "Introduction to Therapeutic Fc-Fusion Proteins," Therapeutic Fc-Fusion Proteins, pp. 219-232, Wiley-VCH 2014.

Bostrom et al., "Purification Systems Based on Bacterial Surface Proteins," Protein Purification, Intech, 2012, pp. 89-136, http://dx.doi.org/10.5772/31078 (50 pages).

PCT International Search Report and Written Opinion for PCT Application No. PCT/EP2017/061164 mailed Sep. 5, 2017 (10 pages).

GB Search Report for GB Application No. 1608229.9 mailed Feb. 28, 2017 (10 pages).

GB Search Report for GB Application No. 1608232.3 mailed Mar. 1, 2017 (10 pages).

(56) References Cited

OTHER PUBLICATIONS

Altschul et al., "Basic Local Alignment Search Tool," J. Mol. Biol., 1990, 215:403-410.
Arshady, "Styrene Based Polymer Supports Developed by Suspension Polymerization," Chimica e L'Industria, 1988, 70(9):70-75.
Gulich et al., "Stability Towards Alkalikine Conditions can be Engineered into a Protein Ligand," Journal of Biotechnology, 2000, 80:169-178.
Hjerten, "The Preparation of Agarose Spheres for Chromatography of Molecules and Particles," Biochim. Boiphys. Acta, 1964, 79:L393-398.
Hober et al., "Protein A Chromatography for Antibody Purification," Journal of Chromatography B, 2007, 848:40-47.
Gel Filtration Principles and Methods, Pharmacia LKB Biotechnology 1991, pp. 6-13.
European Office Action for EP Application No. 17728070.8 mailed Jul. 18, 2019 (9 pages).
European Office Action for EP Application No. 17728070.8 mailed Feb. 9, 2021 (4 pages).
Minakuchi et al., "Remarkable Alkaline Stability of an Engineering Protein A as Immunoglobulin Affinity Ligand: C Doman having only one Amino Acid Substitution," Protein Science, 2013, 22:1230-1238.
Chinese Office Action for CN Application No. 201580062121.1 mailed Jun. 23, 2020 (39 pages, with English translation).
Japanese Office Action for JP Application No. 2018-558405 mailed Mar. 29, 2021 (12 pages with English translation).
"Use of Sodium Hydroxide for Cleaning and Sanitization of Chromatography Media and systems," Application Note 18-1124-57 AI, 2014, https://www.cytivalifesciences.eo.jp/catalog/pdf/18112457AI_AppNote_NaOHforCIP_SIP_final_1.pdf.
Japanese Office Action for JP Application No. 2020-121312, mailed Aug. 10, 2021 (13 pages, with English Translation).
Mccaw et al. "Evaluation of a novel methacrylate-based protein A resin for the purification of immunoglobulins and Fe-Fusion Proteins" Biotechnology Prog. 2014, 30(5) Year: 2014, 12 pages.
Bowie, J., et al. "Deciphering the Message in Protein Sequences: Tolerance to Amino Acid Substitutions", Science, 1990,247:4948, pp. 1306-1310.
Burgess, VVH., et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", Tile Journal of Cell Biology, 1990, 111, pp. 2129-2138.
Lazar, E., et a!. "Transforming Growth Factor ex: Mutation of Aspartic Acid 4 7 and Leucine 48 Results in Different Biologicai Activities", Molecular and Cellular Biology, 1988, 8(3) 1247-1252.
Indian Office Action for IN Application No. 201847041236 mailed Sep. 1, 2022 (7 pages).
Chinese Office Action for CN Application No. 201780028976.1 mailed Sep. 3, 2021 (21 pages).
Japanese Office Action for JP Application No. 2018-558395 mailed May 24, 2021 (11 pages, with English Translation).
Non-Final Office Action for U.S. Appl. No. 16/682,855, mailed Dec. 5, 2019 (14 pages).
Non-Final Office Action for U.S. Appl. No. 16/893,574, mailed Oct. 6, 2020 (39 pages).
Office Action issued in Japanese Patent Application No. 2020-534551, mailed Dec. 5, 2022 with English Summary (13 pages).
Non-Final Office Action in corresponding U.S. Appl. No. 17/149,830, issued Jun. 18, 2024, 6 pages.

* cited by examiner

Alignment of Fc-binding domains

```
E     ---------AQQ  NAFYQVLNMP  NLNADQRNGF  IQSLKDDPSQ  SANVLGEAQK  LNDSQAPK  51  (SEQ ID NO: 1)
D     ADA QQNKFNKDQQ  SAFYEILNMP  NLNEEQRNGF  IQSLKDDPSQ  STNVLGEAKK  LNESQAPK  61  (SEQ ID NO: 2)
A     --A DNN-FNKEQQ  NAFYEILNMP  NLNEEQRNGF  IQSLKDDPSQ  SANLLAEAKK  LNESQAPK  58  (SEQ ID NO: 3)
B     --- ADNKFNKEQQ  NAFYEILHLP  NLNEEQRNGF  IQSLKDDPSQ  SANLLAEAKK  LNDAQAPK  58  (SEQ ID NO: 4)
C     --- ADNKFNKEQQ  NAFYEILHLP  NLTEEQRNGF  IQSLKDDPSV  SKEILAEAKK  LNDAQAPK  58  (SEQ ID NO: 5)
Z     --- VDNKFNKEQQ  NAFYEILHLP  NLNEEQRNAF  IQSLKDDPSQ  SANLLAEAKK  LNDAQAPK  58  (SEQ ID NO: 6)
Zvar  --- VDAKFDKEQQ  NAFYEILHLP  NLTEEQRNAF  IQSLKDDPSQ  SANLLAEAKK  LNDAQAPK  58  (SEQ ID NO: 7)

---       -QQ  NAFYEILHLP  NLTEEQRNAF  IQSLKDDPSQ  SANLLAEAKK  LNDAQ---  47  (SEQ ID NO: 51)
      ---       -QQ  NAFYEILHLP  NLTEEQRNGF  IQSLKDDPSV  SKEILAEAKK  LNDAQ---  47  (SEQ ID NO: 52)

Pos   1           10          20          30          40          50        58
```

Fig. 1

```
                         SEQUENCE LISTING

Sequence total quantity: 109
SEQ ID NO: 1            moltype = AA  length = 51
FEATURE                 Location/Qualifiers
source                  1..51
                        mol_type = protein
                        organism = Staphylococcus aureus
SEQUENCE: 1
AQQNAFYQVL NMPNLNADQR NGFIQSLKDD PSQSANVLGE AQKLNDSQAP K            51

SEQ ID NO: 2            moltype = AA  length = 61
FEATURE                 Location/Qualifiers
source                  1..61
                        mol_type = protein
                        organism = Staphylococcus aureus
SEQUENCE: 2
ADAQQNKFNK DQQSAFYEIL NMPNLNEEQR NGFIQSLKDD PSQSTNVLGE AKKLNESQAP   60
K                                                                  61

SEQ ID NO: 3            moltype = AA  length = 58
FEATURE                 Location/Qualifiers
source                  1..58
                        mol_type = protein
                        organism = Staphylococcus aureus
SEQUENCE: 3
ADNNFNKEQQ NAFYEILNMP NLNEEQRNGF IQSLKDDPSQ SANLLAEAKK LNESQAPK     58

SEQ ID NO: 4            moltype = AA  length = 58
FEATURE                 Location/Qualifiers
source                  1..58
                        mol_type = protein
                        organism = Staphylococcus aureus
SEQUENCE: 4
ADNKFNKEQQ NAFYEILHLP NLNEEQRNGF IQSLKDDPSQ SANLLAEAKK LNDAQAPK     58

SEQ ID NO: 5            moltype = AA  length = 58
FEATURE                 Location/Qualifiers
source                  1..58
                        mol_type = protein
                        organism = Staphylococcus aureus
SEQUENCE: 5
ADNKFNKEQQ NAFYEILHLP NLTEEQRNGF IQSLKDDPSV SKEILAEAKK LNDAQAPK     58

SEQ ID NO: 6            moltype = AA  length = 58
FEATURE                 Location/Qualifiers
source                  1..58
                        mol_type = protein
                        organism = Escherichia coli
SEQUENCE: 6
VDNKFNKEQQ NAFYEILHLP NLNEEQRNAF IQSLKDDPSQ SANLLAEAKK LNDAQAPK     58

SEQ ID NO: 7            moltype = AA  length = 58
FEATURE                 Location/Qualifiers
source                  1..58
                        mol_type = protein
                        organism = Escherichia coli
SEQUENCE: 7
VDAKFDKEQQ NAFYEILHLP NLTEEQRNAF IQSLKDDPSQ SANLLAEAKK LNDAQAPK     58
```

```
SEQ ID NO: 8          moltype = AA   length = 58
FEATURE               Location/Qualifiers
source                1..58
                      mol_type = protein
                      organism = Escherichia coli
SEQUENCE: 8
VDAKFDKEAQ EAFYEILHLP NLTEEQRNAF IQSLKDDPSQ SAALLAEAKK LNDAQAPK    58

SEQ ID NO: 9          moltype = AA   length = 58
FEATURE               Location/Qualifiers
source                1..58
                      mol_type = protein
                      organism = Escherichia coli
SEQUENCE: 9
VDAKFDKEAQ EAFYEILHLP NLTEEQRAAF IQSLKDDPSQ SAALLAEAKK LNDAQAPK    58

SEQ ID NO: 10         moltype = AA   length = 58
FEATURE               Location/Qualifiers
source                1..58
                      mol_type = protein
                      organism = Escherichia coli
SEQUENCE: 10
VDAKFDKEAQ EAFYEILHLP NLTEEQRNAF IQSLKDDPSV SKEILAEAKK LNDAQAPK    58

SEQ ID NO: 11         moltype = AA   length = 58
FEATURE               Location/Qualifiers
source                1..58
                      mol_type = protein
                      organism = Escherichia coli
SEQUENCE: 11
VDAKFDKEAQ EAFYEILHLP NLTEEQRNAF IQSLKDDPSV SKAILAEAKK LNDAQAPK    58

SEQ ID NO: 12         moltype = AA   length = 58
FEATURE               Location/Qualifiers
source                1..58
                      mol_type = protein
                      organism = Escherichia coli
SEQUENCE: 12
VDAKFDKEQQ EAFYEILHLP NLTEEQRNAF IASLKDDPSQ SANLLAEAKK LNDAQAPK    58

SEQ ID NO: 13         moltype = AA   length = 58
FEATURE               Location/Qualifiers
source                1..58
                      mol_type = protein
                      organism = Escherichia coli
SEQUENCE: 13
VDAKFDKEQQ EAFYEILHLP NLTEEQRNAF IQSLKDDPSQ SANLLAEAKK LNDAQAPK    58

SEQ ID NO: 14         moltype = AA   length = 58
FEATURE               Location/Qualifiers
source                1..58
                      mol_type = protein
                      organism = Escherichia coli
SEQUENCE: 14
VDAKFDKEQQ EAFYEILHLP NLTEEQRNAF IESLKDDPSE SANLLAEAKK LNDAQAPK    58

SEQ ID NO: 15         moltype = AA   length = 58
FEATURE               Location/Qualifiers
source                1..58
                      mol_type = protein
                      organism = Escherichia coli
SEQUENCE: 15
VDAKFDKEQQ EAFYEILHLP NLTEEQRNAF IESLKDDPSQ SANLLAEAKR LNDAQAPK    58

SEQ ID NO: 16         moltype = AA   length = 58
FEATURE               Location/Qualifiers
source                1..58
                      mol_type = protein
                      organism = Escherichia coli
SEQUENCE: 16
VDAKFDKEQQ KAFYEILHLP NLTEEQRNAF IQSLKDDPSQ SANLLAEAKK LNDAQAPK    58

SEQ ID NO: 17         moltype = AA   length = 237
FEATURE               Location/Qualifiers
source                1..237
                      mol_type = protein
                      organism = Escherichia coli
SEQUENCE: 17
```

```
AQGTVDAKFD KEAQEAFYEI LHLPNLTEEQ RNAFIQSLKD DPSQSAALLA EAKKLNDAQA    60
PKVDAKFDKE AQEAFYEILH LPNLTEEQRA AFIQSLKDDP SQSAALLAEA KKLNDAQAPK   120
VDAKFDKEAQ EAFYEILHLP NLTEEQRNAF IQSLKDDPSQ SAALLAEAKK LNDAQAPKVD   180
AKFDKEAQEA FYEILHLPNL TEEQRNAFIQ SLKDDPSQSA ALLAEAKKLN DAQAPKC      237

SEQ ID NO: 18          moltype = AA   length = 237
FEATURE                Location/Qualifiers
source                 1..237
                       mol_type = protein
                       organism = Escherichia coli
SEQUENCE: 18
AQGTVDAKFD KEAQEAFYEI LHLPNLTEEQ RAAFIQSLKD DPSQSAALLA EAKKLNDAQA    60
PKVDAKFDKE AQEAFYEILH LPNLTEEQRA AFIQSLKDDP SQSAALLAEA KKLNDAQAPK   120
VDAKFDKEAQ EAFYEILHLP NLTEEQRAAF IQSLKDDPSQ SAALLAEAKK LNDAQAPKVD   180
AKFDKEAQEA FYEILHLPNL TEEQRAAFIQ SLKDDPSQSA ALLAEAKKLN DAQAPKC      237

SEQ ID NO: 19          moltype = AA   length = 237
FEATURE                Location/Qualifiers
source                 1..237
                       mol_type = protein
                       organism = Escherichia coli
SEQUENCE: 19
AQGTVDAKFD KEAQEAFYEI LHLPNLTEEQ RNAFIQSLKD DPSVSKEILA EAKKLNDAQA    60
PKVDAKFDKE AQEAFYEILH LPNLTEEQRN AFIQSLKDDP SVSKEILAEA KKLNDAQAPK   120
VDAKFDKEAQ EAFYEILHLP NLTEEQRNAF IQSLKDDPSV SKEILAEAKK LNDAQAPKVD   180
AKFDKEAQEA FYEILHLPNL TEEQRNAFIQ SLKDDPSVSK EILAEAKKLN DAQAPKC      237

SEQ ID NO: 20          moltype = AA   length = 237
FEATURE                Location/Qualifiers
source                 1..237
                       mol_type = protein
                       organism = Escherichia coli
SEQUENCE: 20
AQGTVDAKFD KEAQEAFYEI LHLPNLTEEQ RNAFIQSLKD DPSVSKAILA EAKKLNDAQA    60
PKVDAKFDKE AQEAFYEILH LPNLTEEQRN AFIQSLKDDP SVSKAILAEA KKLNDAQAPK   120
VDAKFDKEAQ EAFYEILHLP NLTEEQRNAF IQSLKDDPSV SKAILAEAKK LNDAQAPKVD   180
AKFDKEAQEA FYEILHLPNL TEEQRNAFIQ SLKDDPSVSK AILAEAKKLN DAQAPKC      237

SEQ ID NO: 21          moltype = AA   length = 237
FEATURE                Location/Qualifiers
source                 1..237
                       mol_type = protein
                       organism = Escherichia coli
SEQUENCE: 21
AQGTVDAKFD KEQQNAFYEI LHLPNLTEEQ RNAFIQSLKD DPSQSANLLA EAKKLNDAQA    60
PKVDAKFDKE QQNAFYEILH LPNLTEEQRN AFIQSLKDDP SQSANLLAEA KKLNDAQAPK   120
VDAKFDKEQQ NAFYEILHLP NLTEEQRNAF IQSLKDDPSQ SANLLAEAKK LNDAQAPKVD   180
AKFDKEQQNA FYEILHLPNL TEEQRNAFIQ SLKDDPSQSA NLLAEAKKLN DAQAPKC      237

SEQ ID NO: 22          moltype = AA   length = 58
FEATURE                Location/Qualifiers
source                 1..58
                       mol_type = protein
                       organism = Staphylococcus aureus
SEQUENCE: 22
ADNNFNKEQQ NAFYEILNMP NLNEEQRNGF IQSLKDDPSQ SANLLSEAKK LNESQAPK     58

SEQ ID NO: 23          moltype = AA   length = 58
FEATURE                Location/Qualifiers
source                 1..58
                       mol_type = protein
                       organism = Escherichia coli
SEQUENCE: 23
VDAKFDKEQQ KAFYEILKLP NLTEEQRNAF IQKLKDEPSQ SRAILAEAKR YNDAQAPK     58

SEQ ID NO: 24          moltype = AA   length = 58
FEATURE                Location/Qualifiers
source                 1..58
                       mol_type = protein
                       organism = Escherichia coli
SEQUENCE: 24
VDAKFDKEAQ EAFYEILHLP NLTEEQRAAF IQSLKDDPSV SKAILAEAKK LNDAQAPK     58

SEQ ID NO: 25          moltype = AA   length = 58
FEATURE                Location/Qualifiers
source                 1..58
                       mol_type = protein
                       organism = Escherichia coli
SEQUENCE: 25
```

```
VDAKFDKEAQ KAFYEILKLP NLTEEQRAAF IQKLKDEPSQ SRAILAEAKR YNDAQAPK    58

SEQ ID NO: 26           moltype = AA  length = 58
FEATURE                 Location/Qualifiers
source                  1..58
                        mol_type = protein
                        organism = Escherichia coli
SEQUENCE: 26
VDAKFDKEQQ KAFYEILKLP NLTEEQRNAF IQSLKDEPSQ SRAILAEAKK LNDAQAPK    58

SEQ ID NO: 27           moltype = AA  length = 58
FEATURE                 Location/Qualifiers
source                  1..58
                        mol_type = protein
                        organism = Escherichia coli
SEQUENCE: 27
VDAKFDKEAQ KAFYEILKLP NLTEEQRNAF IQSLKDEPSQ SRAILAEAKK LNDAQAPK    58

SEQ ID NO: 28           moltype = AA  length = 58
FEATURE                 Location/Qualifiers
source                  1..58
                        mol_type = protein
                        organism = Escherichia coli
SEQUENCE: 28
VDAKFDKEAQ KAFYEILKLP NLTEEQRNAF IQSLKDEPSQ SRAILAEAKR LNDAQAPK    58

SEQ ID NO: 29           moltype = AA  length = 58
FEATURE                 Location/Qualifiers
source                  1..58
                        mol_type = protein
                        organism = Escherichia coli
SEQUENCE: 29
VDAKFDKEAQ KAFYEILKLP NLTEEQRNAF IQSLKDEPSQ SRNLLAEAKK LNDAQAPK    58

SEQ ID NO: 30           moltype = AA  length = 237
FEATURE                 Location/Qualifiers
source                  1..237
                        mol_type = protein
                        organism = Escherichia coli
SEQUENCE: 30
AQGTVDAKFD KEQQKAFYEI LKLPNLTEEQ RNAFIQKLKD EPSQSRAILA EAKRYNDAQA   60
PKVDAKFDKE QQKAFYEILK LPNLTEEQRN AFIQKLKDEP SQSRAILAEA KRYNDAQAPK  120
VDAKFDKEQQ KAFYEILKLP NLTEEQRNAF IQKLKDEPSQ SRAILAEAKR YNDAQAPKVD  180
AKFDKEQQKA FYEILKLPNL TEEQRNAFIQ KLKDEPSQSR AILAEAKRYN DAQAPKC     237

SEQ ID NO: 31           moltype = AA  length = 237
FEATURE                 Location/Qualifiers
source                  1..237
                        mol_type = protein
                        organism = Escherichia coli
SEQUENCE: 31
AQGTVDAKFD KEAQKAFYEI LKLPNLTEEQ RNAFIQSLKD EPSQSRNLLA EAKKLNDAQA   60
PKVDAKFDKE AQKAFYEILK LPNLTEEQRN AFIQSLKDEP SQSRNLLAEA KKLNDAQAPK  120
VDAKFDKEAQ KAFYEILKLP NLTEEQRNAF IQSLKDEPSQ SRNLLAEAKK LNDAQAPKVD  180
AKFDKEAQKA FYEILKLPNL TEEQRNAFIQ SLKDEPSQSR NLLAEAKKLN DAQAPKC     237

SEQ ID NO: 32           moltype = AA  length = 237
FEATURE                 Location/Qualifiers
source                  1..237
                        mol_type = protein
                        organism = Escherichia coli
SEQUENCE: 32
AQGTVDAKFD KEAQEAFYEI LHLPNLTEEQ RAAFIQSLKD DPSVSKAILA EAKKLNDAQA   60
PKVDAKFDKE AQEAFYEILH LPNLTEEQRA AFIQSLKDDP SVSKAILAEA KKLNDAQAPK  120
VDAKFDKEAQ EAFYEILHLP NLTEEQRAAF IQSLKDDPSV SKAILAEAKK LNDAQAPKVD  180
AKFDKEAQEA FYEILHLPNL TEEQRAAFIQ SLKDDPSVSK AILAEAKKLN DAQAPKC     237

SEQ ID NO: 33           moltype = AA  length = 353
FEATURE                 Location/Qualifiers
source                  1..353
                        mol_type = protein
                        organism = Escherichia coli
SEQUENCE: 33
AQGTVDAKFD KEAQEAFYEI LHLPNLTEEQ RNAFIQSLKD DPSVSKAILA EAKKLNDAQA   60
PKVDAKFDKE AQEAFYEILH LPNLTEEQRN AFIQSLKDDP SVSKAILAEA KKLNDAQAPK  120
VDAKFDKEAQ EAFYEILHLP NLTEEQRNAF IQSLKDDPSV SKAILAEAKK LNDAQAPKVD  180
AKFDKEAQEA FYEILHLPNL TEEQRNAFIQ SLKDDPSVSK AILAEAKKLN DAQAPKVDAK  240
FDKEAQEAFY EILHLPNLTE EQRNAFIQSL KDDPSVSKAI LAEAKKLNDA QAPKVDAKFD  300
KEAQEAFYEI LHLPNLTEEQ RNAFIQSLKD DPSVSKAILA EAKKLNDAQA PKC         353
```

```
SEQ ID NO: 34            moltype = AA   length = 237
FEATURE                  Location/Qualifiers
source                   1..237
                         mol_type = protein
                         organism = Escherichia coli
SEQUENCE: 34
AQGTVDAKFD KEAQEAFYEI LHLPNLTEEQ RNAFIQSLKD EPSVSKAILA EAKKLNDAQA   60
PKVDAKFDKE AQEAFYEILH LPNLTEEQRN AFIQSLKDEP SVSKAILAEA KKLNDAQAPK  120
VDAKFDKEAQ EAFYEILHLP NLTEEQRNAF IQSLKDEPSV SKAILAEAKK LNDAQAPKVD  180
AKFDKEAQEA FYEILHLPNL TEEQRNAFIQ SLKDEPSVSK AILAEAKKLN DAQAPKC     237

SEQ ID NO: 35            moltype = AA   length = 237
FEATURE                  Location/Qualifiers
source                   1..237
                         mol_type = protein
                         organism = Escherichia coli
SEQUENCE: 35
AQGTVDAKFD KEAQEAFYEI LHLPNLTEEQ RNAFIQSLKD EPSVSRAILA EAKKLNDAQA   60
PKVDAKFDKE AQEAFYEILH LPNLTEEQRN AFIQSLKDEP SVSRAILAEA KKLNDAQAPK  120
VDAKFDKEAQ EAFYEILHLP NLTEEQRNAF IQSLKDEPSV SRAILAEAKK LNDAQAPKVD  180
AKFDKEAQEA FYEILHLPNL TEEQRNAFIQ SLKDEPSVSR AILAEAKKLN DAQAPKC     237

SEQ ID NO: 36            moltype = AA   length = 58
FEATURE                  Location/Qualifiers
source                   1..58
                         mol_type = protein
                         organism = Escherichia coli
SEQUENCE: 36
ADNKFNKEAQ EAFYEILHLP NLNEEQRNGF IQSLKDDPSV SKAILAEAKK LNDAQAPK     58

SEQ ID NO: 37            moltype = AA   length = 58
FEATURE                  Location/Qualifiers
source                   1..58
                         mol_type = protein
                         organism = Escherichia coli
SEQUENCE: 37
ADNKFNKEAQ EAFYEILHLP NLTEEQRNGF IQSLKDDPSV SKAILAEAKK LNDAQAPK     58

SEQ ID NO: 38            moltype = AA   length = 58
FEATURE                  Location/Qualifiers
source                   1..58
                         mol_type = protein
                         organism = Escherichia coli
SEQUENCE: 38
VDAKFDKEQQ YAFYEILHLP NLTEEQRNAF IQSLKDDPSQ SANLLAEAKK LNDAQAPK     58

SEQ ID NO: 39            moltype = AA   length = 58
FEATURE                  Location/Qualifiers
source                   1..58
                         mol_type = protein
                         organism = Escherichia coli
SEQUENCE: 39
VDAKFDKEQQ TAFYEILHLP NLTEEQRNAF IQSLKDDPSQ SANLLAEAKK LNDAQAPK     58

SEQ ID NO: 40            moltype = AA   length = 58
FEATURE                  Location/Qualifiers
source                   1..58
                         mol_type = protein
                         organism = Escherichia coli
SEQUENCE: 40
VDAKFDKEQQ FAFYEILHLP NLTEEQRNAF IQSLKDDPSQ SANLLAEAKK LNDAQAPK     58

SEQ ID NO: 41            moltype = AA   length = 58
FEATURE                  Location/Qualifiers
source                   1..58
                         mol_type = protein
                         organism = Escherichia coli
SEQUENCE: 41
VDAKFDKEQQ LAFYEILHLP NLTEEQRNAF IQSLKDDPSQ SANLLAEAKK LNDAQAPK     58

SEQ ID NO: 42            moltype = AA   length = 58
FEATURE                  Location/Qualifiers
source                   1..58
                         mol_type = protein
                         organism = Escherichia coli
SEQUENCE: 42
VDAKFDKEQQ WAFYEILHLP NLTEEQRNAF IQSLKDDPSQ SANLLAEAKK LNDAQAPK     58
```

```
SEQ ID NO: 43              moltype = AA  length = 58
FEATURE                    Location/Qualifiers
source                     1..58
                           mol_type = protein
                           organism = Escherichia coli
SEQUENCE: 43
VDAKFDKEQQ IAFYEILHLP NLTEEQRNAF IQSLKDDPSQ SANLLAEAKK LNDAQAPK      58

SEQ ID NO: 44              moltype = AA  length = 58
FEATURE                    Location/Qualifiers
source                     1..58
                           mol_type = protein
                           organism = Escherichia coli
SEQUENCE: 44
VDAKFDKEQQ MAFYEILHLP NLTEEQRNAF IQSLKDDPSQ SANLLAEAKK LNDAQAPK      58

SEQ ID NO: 45              moltype = AA  length = 58
FEATURE                    Location/Qualifiers
source                     1..58
                           mol_type = protein
                           organism = Escherichia coli
SEQUENCE: 45
VDAKFDKEQQ VAFYEILHLP NLTEEQRNAF IQSLKDDPSQ SANLLAEAKK LNDAQAPK      58

SEQ ID NO: 46              moltype = AA  length = 58
FEATURE                    Location/Qualifiers
source                     1..58
                           mol_type = protein
                           organism = Escherichia coli
SEQUENCE: 46
VDAKFDKEQQ AAFYEILHLP NLTEEQRNAF IQSLKDDPSQ SANLLAEAKK LNDAQAPK      58

SEQ ID NO: 47              moltype = AA  length = 58
FEATURE                    Location/Qualifiers
source                     1..58
                           mol_type = protein
                           organism = Escherichia coli
SEQUENCE: 47
VDAKFDKEQQ HAFYEILHLP NLTEEQRNAF IQSLKDDPSQ SANLLAEAKK LNDAQAPK      58

SEQ ID NO: 48              moltype = AA  length = 58
FEATURE                    Location/Qualifiers
source                     1..58
                           mol_type = protein
                           organism = Escherichia coli
SEQUENCE: 48
VDAKFDKEQQ RAFYEILHLP NLTEEQRNAF IQSLKDDPSQ SANLLAEAKK LNDAQAPK      58

SEQ ID NO: 49              moltype = AA  length = 58
FEATURE                    Location/Qualifiers
source                     1..58
                           mol_type = protein
                           organism = Escherichia coli
SEQUENCE: 49
VDAKFDKEAQ EAFYEILHLP NLTEEQRNAF IQSLKDEPSV SKAILAEAKK LNDAQAPK      58

SEQ ID NO: 50              moltype = AA  length = 58
FEATURE                    Location/Qualifiers
source                     1..58
                           mol_type = protein
                           organism = Escherichia coli
SEQUENCE: 50
VDAKFDKEAQ EAFYEILHLP NLTEEQRNAF IQSLKDEPSV SRAILAEAKK LNDAQAPK      58

SEQ ID NO: 51              moltype = AA  length = 47
FEATURE                    Location/Qualifiers
source                     1..47
                           mol_type = protein
                           organism = Escherichia coli
SEQUENCE: 51
QQNAFYEILH LPNLTEEQRN AFIQSLKDDP SQSANLLAEA KKLNDAQ                  47

SEQ ID NO: 52              moltype = AA  length = 47
FEATURE                    Location/Qualifiers
source                     1..47
                           mol_type = protein
                           organism = Staphylococcus aureus
SEQUENCE: 52
QQNAFYEILH LPNLTEEQRN GFIQSLKDDP SVSKEILAEA KKLNDAQ                  47
```

```
SEQ ID NO: 53           moltype = AA  length = 47
FEATURE                 Location/Qualifiers
SITE                    1
                        note = misc_feature - Xaa can be any naturally occurring
                         amino acid
SITE                    3
                        note = misc_feature - Xaa can be any naturally occurring
                         amino acid
SITE                    10
                        note = misc_feature - Xaa can be any naturally occurring
                         amino acid
REGION                  20..21
                        note = misc_feature - Xaa can be any naturally occurring
                         amino acid
REGION                  24..25
                        note = misc_feature - Xaa can be any naturally occurring
                         amino acid
SITE                    29
                        note = misc_feature - Xaa can be any naturally occurring
                         amino acid
SITE                    32
                        note = misc_feature - Xaa can be any naturally occurring
                         amino acid
REGION                  34..36
                        note = misc_feature - Xaa can be any naturally occurring
                         amino acid
REGION                  42..43
                        note = misc_feature - Xaa can be any naturally occurring
                         amino acid
SITE                    45
                        note = misc_feature - Xaa can be any naturally occurring
                         amino acid
source                  1..47
                        mol_type = protein
                        organism = Escherichia coli
SEQUENCE: 53
XQXAFYEILX LPNLTEEQRX XFIXXLKDXP SXSXXXLAEA KXXNXAQ             47

SEQ ID NO: 54           moltype = AA  length = 58
FEATURE                 Location/Qualifiers
source                  1..58
                        mol_type = protein
                        organism = Escherichia coli
SEQUENCE: 54
VDAKFDKEAQ EAFYEILHLP NLTEEQRNGF IQSLKDDPSV SKAILAEAKK LNDAQAPK  58

SEQ ID NO: 55           moltype = AA  length = 58
FEATURE                 Location/Qualifiers
source                  1..58
                        mol_type = protein
                        organism = Escherichia coli
SEQUENCE: 55
VDAKFDKEAQ EAFYEILHLP NLTEEQRNSF IQSLKDDPSV SKAILAEAKK LNDAQAPK  58

SEQ ID NO: 56           moltype = AA  length = 58
FEATURE                 Location/Qualifiers
source                  1..58
                        mol_type = protein
                        organism = Escherichia coli
SEQUENCE: 56
VDAKFDKEAQ EAFYEILHLP NLTEEQRNYF IQSLKDDPSV SKAILAEAKK LNDAQAPK  58

SEQ ID NO: 57           moltype = AA  length = 58
FEATURE                 Location/Qualifiers
source                  1..58
                        mol_type = protein
                        organism = Escherichia coli
SEQUENCE: 57
VDAKFDKEAQ EAFYEILHLP NLTEEQRNQF IQSLKDDPSV SKAILAEAKK LNDAQAPK  58

SEQ ID NO: 58           moltype = AA  length = 58
FEATURE                 Location/Qualifiers
source                  1..58
                        mol_type = protein
                        organism = Escherichia coli
SEQUENCE: 58
VDAKFDKEAQ EAFYEILHLP NLTEEQRNTF IQSLKDDPSV SKAILAEAKK LNDAQAPK  58
```

```
SEQ ID NO: 59          moltype = AA   length = 58
FEATURE                Location/Qualifiers
source                 1..58
                       mol_type = protein
                       organism = Escherichia coli
SEQUENCE: 59
VDAKFDKEAQ EAFYEILHLP NLTEEQRNNF IQSLKDDPSV SKAILAEAKK LNDAQAPK      58

SEQ ID NO: 60          moltype = AA   length = 58
FEATURE                Location/Qualifiers
source                 1..58
                       mol_type = protein
                       organism = Escherichia coli
SEQUENCE: 60
VDAKFDKEAQ EAFYEILHLP NLTEEQRNFF IQSLKDDPSV SKAILAEAKK LNDAQAPK      58

SEQ ID NO: 61          moltype = AA   length = 58
FEATURE                Location/Qualifiers
source                 1..58
                       mol_type = protein
                       organism = Escherichia coli
SEQUENCE: 61
VDAKFDKEAQ EAFYEILHLP NLTEEQRNLF IQSLKDDPSV SKAILAEAKK LNDAQAPK      58

SEQ ID NO: 62          moltype = AA   length = 58
FEATURE                Location/Qualifiers
source                 1..58
                       mol_type = protein
                       organism = Escherichia coli
SEQUENCE: 62
VDAKFDKEAQ EAFYEILHLP NLTEEQRNWF IQSLKDDPSV SKAILAEAKK LNDAQAPK      58

SEQ ID NO: 63          moltype = AA   length = 58
FEATURE                Location/Qualifiers
source                 1..58
                       mol_type = protein
                       organism = Escherichia coli
SEQUENCE: 63
VDAKFDKEAQ EAFYEILHLP NLTEEQRNIF IQSLKDDPSV SKAILAEAKK LNDAQAPK      58

SEQ ID NO: 64          moltype = AA   length = 58
FEATURE                Location/Qualifiers
source                 1..58
                       mol_type = protein
                       organism = Escherichia coli
SEQUENCE: 64
VDAKFDKEAQ EAFYEILHLP NLTEEQRNMF IQSLKDDPSV SKAILAEAKK LNDAQAPK      58

SEQ ID NO: 65          moltype = AA   length = 58
FEATURE                Location/Qualifiers
source                 1..58
                       mol_type = protein
                       organism = Escherichia coli
SEQUENCE: 65
VDAKFDKEAQ EAFYEILHLP NLTEEQRNVF IQSLKDDPSV SKAILAEAKK LNDAQAPK      58

SEQ ID NO: 66          moltype = AA   length = 58
FEATURE                Location/Qualifiers
source                 1..58
                       mol_type = protein
                       organism = Escherichia coli
SEQUENCE: 66
VDAKFDKEAQ EAFYEILHLP NLTEEQRNDF IQSLKDDPSV SKAILAEAKK LNDAQAPK      58

SEQ ID NO: 67          moltype = AA   length = 58
FEATURE                Location/Qualifiers
source                 1..58
                       mol_type = protein
                       organism = Escherichia coli
SEQUENCE: 67
VDAKFDKEAQ EAFYEILHLP NLTEEQRNEF IQSLKDDPSV SKAILAEAKK LNDAQAPK      58

SEQ ID NO: 68          moltype = AA   length = 58
FEATURE                Location/Qualifiers
source                 1..58
                       mol_type = protein
                       organism = Escherichia coli
SEQUENCE: 68
VDAKFDKEAQ EAFYEILHLP NLTEEQRNHF IQSLKDDPSV SKAILAEAKK LNDAQAPK      58
```

```
SEQ ID NO: 69          moltype = AA  length = 58
FEATURE                Location/Qualifiers
source                 1..58
                       mol_type = protein
                       organism = Escherichia coli
SEQUENCE: 69
VDAKFDKEAQ EAFYEILHLP NLTEEQRNRF IQSLKDDPSV SKAILAEAKK LNDAQAPK    58

SEQ ID NO: 70          moltype = AA  length = 58
FEATURE                Location/Qualifiers
source                 1..58
                       mol_type = protein
                       organism = Escherichia coli
SEQUENCE: 70
VDAKFDKEAQ EAFYEILHLP NLTEEQRNKF IQSLKDDPSV SKAILAEAKK LNDAQAPK    58

SEQ ID NO: 71          moltype = AA  length = 58
FEATURE                Location/Qualifiers
source                 1..58
                       mol_type = protein
                       organism = Escherichia coli
SEQUENCE: 71
VDAKFDKEAQ EAFYEILHLP NLTEEQRNAF IQSLKDDPSV SKAILAEAKK LNFAQAPK    58

SEQ ID NO: 72          moltype = AA  length = 58
FEATURE                Location/Qualifiers
source                 1..58
                       mol_type = protein
                       organism = Escherichia coli
SEQUENCE: 72
VDAKFDKEAQ EAFYEILHLP NLTEEQRNAF IQSLKDDPSV SKAILAEAKK LNYAQAPK    58

SEQ ID NO: 73          moltype = AA  length = 58
FEATURE                Location/Qualifiers
source                 1..58
                       mol_type = protein
                       organism = Escherichia coli
SEQUENCE: 73
VDAKFDKEAQ EAFYEILHLP NLTEEQRNAF IQSLKDDPSV SKAILAEAKK LNWAQAPK    58

SEQ ID NO: 74          moltype = AA  length = 58
FEATURE                Location/Qualifiers
source                 1..58
                       mol_type = protein
                       organism = Escherichia coli
SEQUENCE: 74
VDAKFDKEAQ EAFYEILHLP NLTEEQRNAF IQSLKDDPSV SKAILAEAKK LNKAQAPK    58

SEQ ID NO: 75          moltype = AA  length = 58
FEATURE                Location/Qualifiers
source                 1..58
                       mol_type = protein
                       organism = Escherichia coli
SEQUENCE: 75
VDAKFDKEAQ EAFYEILHLP NLTEEQRNAF IQSLKDDPSV SKAILAEAKK LNRAQAPK    58

SEQ ID NO: 76          moltype = AA  length = 57
FEATURE                Location/Qualifiers
source                 1..57
                       mol_type = protein
                       organism = Escherichia coli
SEQUENCE: 76
VDAKFDKEQE AFYEILHLPN LTEEQRNAFI QSLKDDPSVS KAILAEAKKL NDAQAPK     57

SEQ ID NO: 77          moltype = AA  length = 57
FEATURE                Location/Qualifiers
source                 1..57
                       mol_type = protein
                       organism = Escherichia coli
SEQUENCE: 77
VDAKFDKEAQ EAFYEILHLP NLTEEQRNAF IQSLKDDPSS KAILAEAKKL NDAQAPK     57

SEQ ID NO: 78          moltype = AA  length = 57
FEATURE                Location/Qualifiers
source                 1..57
                       mol_type = protein
                       organism = Escherichia coli
SEQUENCE: 78
```

```
VDAKFDKEAQ EAFYEILHLP NLTEEQRNAF IQSLKDDPSV SAILAEAKKL NDAQAPK         57

SEQ ID NO: 79            moltype = AA   length = 57
FEATURE                  Location/Qualifiers
source                   1..57
                         mol_type = protein
                         organism = Escherichia coli
SEQUENCE: 79
VDAKFDKEAQ EAFYEILHLP NLTEEQRNAF IQSLKDDPSV SKILAEAKKL NDAQAPK         57

SEQ ID NO: 80            moltype = AA   length = 114
FEATURE                  Location/Qualifiers
source                   1..114
                         mol_type = protein
                         organism = Escherichia coli
SEQUENCE: 80
VDAKFDKEAQ EAFYEILHLP NLTEEQRNAF IQSLKDDPSV SKAILAEAKK LNDAQAPKVF      60
DKEAQEAFYE ILHLPNLTEE QRNAFIQSLK DDPSVSKAIL AEAKKLNDAQ APKC           114

SEQ ID NO: 81            moltype = AA   length = 114
FEATURE                  Location/Qualifiers
source                   1..114
                         mol_type = protein
                         organism = Escherichia coli
SEQUENCE: 81
VDAKFDKEAQ EAFYEILHLP NLTEEQRNAF IQSLKDDPSV SKAILAEAKK LNDAQAPAKF      60
DKEAQEAFYE ILHLPNLTEE QRNAFIQSLK DDPSVSKAIL AEAKKLNDAQ APKC           114

SEQ ID NO: 82            moltype = AA   length = 114
FEATURE                  Location/Qualifiers
source                   1..114
                         mol_type = protein
                         organism = Escherichia coli
SEQUENCE: 82
VDAKFDKEAQ EAFYEILHLP NLTEEQRNAF IQSLKDDPSV SKAILAEAKK LNDAQAPAKF      60
DKEAQEAFYE ILHLPNLTEE QRNAFIQSLK DDPSVSKAIL AEAKKLNDAQ APKC           114

SEQ ID NO: 83            moltype = AA   length = 112
FEATURE                  Location/Qualifiers
source                   1..112
                         mol_type = protein
                         organism = Escherichia coli
SEQUENCE: 83
VDAKFDKEAQ EAFYEILHLP NLTEEQRNAF IQSLKDDPSV SKAILAEAKK LNDAQAPKVD      60
AAQEAFYEIL HLPNLTEEQR NAFIQSLKDD PSVSKAILAE AKKLNDAQAP KC             112

SEQ ID NO: 84            moltype = AA   length = 114
FEATURE                  Location/Qualifiers
source                   1..114
                         mol_type = protein
                         organism = Escherichia coli
SEQUENCE: 84
VDAKFDKEAQ EAFYEILHLP NLTEEQRNAF IQSLKDDPSV SKAILAEAKK LNDAQVDAKF      60
DKEAQEAFYE ILHLPNLTEE QRNAFIQSLK DDPSVSKAIL AEAKKLNDAQ APKC           114

SEQ ID NO: 85            moltype = AA   length = 114
FEATURE                  Location/Qualifiers
source                   1..114
                         mol_type = protein
                         organism = Escherichia coli
SEQUENCE: 85
VDAKFDKEAQ EAFYEILHLP NLTEEQRNAF IQSLKDDPSV SKAILAEAKK LNDAQAPKKF      60
DKEAQEAFYE ILHLPNLTEE QRNAFIQSLK DDPSVSKAIL AEAKKLNDAQ APKC           114

SEQ ID NO: 86            moltype = AA   length = 109
FEATURE                  Location/Qualifiers
source                   1..109
                         mol_type = protein
                         organism = Escherichia coli
SEQUENCE: 86
VDAKFDKEAQ EAFYEILHLP NLTEEQRNAF IQSLKDDPSV SKAILAEAKK LNDAQAPKAQ      60
EAFYEILHLP NLTEEQRNAF IQSLKDDPSV SKAILAEAKK LNDAQAPKC                 109

SEQ ID NO: 87            moltype = AA   length = 121
FEATURE                  Location/Qualifiers
source                   1..121
                         mol_type = protein
                         organism = Escherichia coli
SEQUENCE: 87
```

```
VDAKFDKEAQ EAFYEILHLP NLTEEQRNAF IQSLKDDPSV SKAILAEAKK LNDAQAPKYE      60
DGVDAKFDKE AQEAFYEILH LPNLTEEQRN AFIQSLKDDP SVSKAILAEA KKLNDAQAPK     120
C                                                                    121

SEQ ID NO: 88           moltype = AA  length = 117
FEATURE                 Location/Qualifiers
source                  1..117
                        mol_type = protein
                        organism = Escherichia coli
SEQUENCE: 88
VDAKFDKEAQ EAFYEILHLP NLTEEQRNAF IQSLKDDPSV SKAILAEAKK LNDAQAPKVD      60
AKFDKEAQEA FYEILHLPNL TEEQRNAFIQ SLKDDPSVSK AILAEAKKLN DAQAPKC        117

SEQ ID NO: 89           moltype = AA  length = 55
FEATURE                 Location/Qualifiers
source                  1..55
                        mol_type = protein
                        organism = Escherichia coli
SEQUENCE: 89
VFDKEAQEAF YEILHLPNLT EEQRNAFIQS LKDDPSVSKA ILAEAKKLND AQAPK            55

SEQ ID NO: 90           moltype = AA  length = 55
FEATURE                 Location/Qualifiers
source                  1..55
                        mol_type = protein
                        organism = Escherichia coli
SEQUENCE: 90
AKFDKEAQEA FYEILHLPNL TEEQRNAFIQ SLKDDPSVSK AILAEAKKLN DAQAP            55

SEQ ID NO: 91           moltype = AA  length = 53
FEATURE                 Location/Qualifiers
source                  1..53
                        mol_type = protein
                        organism = Escherichia coli
SEQUENCE: 91
VDAAQEAFYE ILHLPNLTEE QRNAFIQSLK DDPSVSKAIL AEAKKLNDAQ APK              53

SEQ ID NO: 92           moltype = AA  length = 55
FEATURE                 Location/Qualifiers
source                  1..55
                        mol_type = protein
                        organism = Escherichia coli
SEQUENCE: 92
VDAKFDKEAQ EAFYEILHLP NLTEEQRNAF IQSLKDDPSV SKAILAEAKK LNDAQ            55

SEQ ID NO: 93           moltype = AA  length = 55
FEATURE                 Location/Qualifiers
source                  1..55
                        mol_type = protein
                        organism = Escherichia coli
SEQUENCE: 93
KFDKEAQEAF YEILHLPNLT EEQRNAFIQS LKDDPSVSKA ILAEAKKLND AQAPK            55

SEQ ID NO: 94           moltype = AA  length = 50
FEATURE                 Location/Qualifiers
source                  1..50
                        mol_type = protein
                        organism = Escherichia coli
SEQUENCE: 94
AQEAFYEILH LPNLTEEQRN AFIQSLKDDP SVSKAILAEA KKLNDAQAPK                  50

SEQ ID NO: 95           moltype = AA  length = 62
FEATURE                 Location/Qualifiers
source                  1..62
                        mol_type = protein
                        organism = Escherichia coli
SEQUENCE: 95
VDAKFDKEAQ EAFYEILHLP NLTEEQRNAF IQSLKDDPSV SKAILAEAKK LNDAQAPKYE       60
DG                                                                     62

SEQ ID NO: 96           moltype = AA  length = 11
FEATURE                 Location/Qualifiers
source                  1..11
                        mol_type = protein
                        organism = Escherichia coli
SEQUENCE: 96
APKVDAKFDK E                                                           11

SEQ ID NO: 97           moltype = AA  length = 11
```

```
FEATURE                 Location/Qualifiers
source                  1..11
                        mol_type = protein
                        organism = Escherichia coli
SEQUENCE: 97
APKVDNKFNK E                                                            11

SEQ ID NO: 98           moltype = AA  length = 11
FEATURE                 Location/Qualifiers
source                  1..11
                        mol_type = protein
                        organism = Escherichia coli
SEQUENCE: 98
APKADNKFNK E                                                            11

SEQ ID NO: 99           moltype = AA  length = 8
FEATURE                 Location/Qualifiers
source                  1..8
                        mol_type = protein
                        organism = Escherichia coli
SEQUENCE: 99
APKVFDKE                                                                 8

SEQ ID NO: 100          moltype = AA  length = 8
FEATURE                 Location/Qualifiers
source                  1..8
                        mol_type = protein
                        organism = Escherichia coli
SEQUENCE: 100
APAKFDKE                                                                 8

SEQ ID NO: 101          moltype = AA  length = 6
FEATURE                 Location/Qualifiers
source                  1..6
                        mol_type = protein
                        organism = Escherichia coli
SEQUENCE: 101
AKFDKE                                                                   6

SEQ ID NO: 102          moltype = AA  length = 6
FEATURE                 Location/Qualifiers
source                  1..6
                        mol_type = protein
                        organism = Escherichia coli
SEQUENCE: 102
APKVDA                                                                   6

SEQ ID NO: 103          moltype = AA  length = 8
FEATURE                 Location/Qualifiers
source                  1..8
                        mol_type = protein
                        organism = Escherichia coli
SEQUENCE: 103
VDAKFDKE                                                                 8

SEQ ID NO: 104          moltype = AA  length = 8
FEATURE                 Location/Qualifiers
source                  1..8
                        mol_type = protein
                        organism = Escherichia coli
SEQUENCE: 104
APKKFDKE                                                                 8

SEQ ID NO: 105          moltype = AA  length = 15
FEATURE                 Location/Qualifiers
source                  1..15
                        mol_type = protein
                        organism = Escherichia coli
SEQUENCE: 105
APKYEDGVDA KFDKE                                                        15

SEQ ID NO: 106          moltype = AA  length = 4
FEATURE                 Location/Qualifiers
source                  1..4
                        mol_type = protein
                        organism = Escherichia coli
SEQUENCE: 106
YEDG                                                                     4
```

```
SEQ ID NO: 107          moltype = AA  length = 4
FEATURE                 Location/Qualifiers
source                  1..4
                        mol_type = protein
                        organism = Escherichia coli
SEQUENCE: 107
AQGT                                                                    4

SEQ ID NO: 108          moltype = AA  length = 10
FEATURE                 Location/Qualifiers
source                  1..10
                        mol_type = protein
                        organism = Escherichia coli
SEQUENCE: 108
AQVDAKFDKE                                                             10

SEQ ID NO: 109          moltype = AA  length = 12
FEATURE                 Location/Qualifiers
source                  1..12
                        mol_type = protein
                        organism = Escherichia coli
SEQUENCE: 109
AQGTVDAKFD KE                                                          12
```

SEPARATION MATRIX

CROSS REFERENCE TO RELATED APPLICATIONS

This application is a continuation of U.S. application Ser. No. 17/221,438, filed Apr. 2, 2021, which is a continuation of U.S. Application No. 16/893,574, filed Jun. 5, 2020, now U.S. Pat. No. 10,995,113, issued Jun. 4, 2021, which is a continuation of U.S. application Ser. No. 16/682,855, filed Nov. 13, 2019, now U.S. Pat. No. 10,711,035, issued Jul. 14, 2020, which is a continuation of U.S. application Ser. No. 16/096,952, filed Oct. 26, 2018, now U.S. Pat. No. 10,513, 537, issued Dec. 24, 2019, which claims the priority benefit of PCT/EP2017/061164 filed on May 10, 2017, which claims priority benefit of U.S. application Ser. No. 15/282, 367, filed Sep. 30, 2016, and Great Britain Application Nos. 1608229.9 and 1608232.3, both of which were filed May 11, 2016. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on Oct. 22, 2018, is named 313838A_ST26.XML and is 104,000 bytes in size.

TECHNICAL FIELD OF THE INVENTION

The present invention relates to the field of affinity chromatography, and more specifically to mutated immunoglobulin-binding domains of Protein A, which are useful in affinity chromatography of immunoglobulins. The invention also relates to multimers of the mutated domains and to separation matrices containing the mutated domains or multimers.

BACKGROUND OF THE INVENTION

Immunoglobulins represent the most prevalent biopharmaceutical products in either manufacture or development worldwide. The high commercial demand for and hence value of this particular therapeutic market has led to the emphasis being placed on pharmaceutical companies to maximize the productivity of their respective mAb manufacturing processes whilst controlling the associated costs.

Affinity chromatography is used in most cases, as one of the key steps in the purification of these immunoglobulin molecules, such as monoclonal or polyclonal antibodies. A particularly interesting class of affinity reagents is proteins capable of specific binding to invariable parts of an immunoglobulin molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species. These domains are commonly denoted as the E-, D-, A-, B- and C-domains.

Staphylococcal protein A (SpA) based reagents have due to their high affinity and selectivity found a widespread use in the field of biotechnology, e.g. in affinity chromatography for capture and purification of antibodies as well as for detection or quantification. At present, SpA-based affinity medium probably is the most widely used affinity medium for isolation of monoclonal antibodies and their fragments from different samples including industrial cell culture supernatants. Accordingly, various matrices comprising protein A-ligands are commercially available, for example, in the form of native protein A (e.g. Protein A SEPHAROSE, GE Healthcare, Uppsala, Sweden) and also comprised of recombinant protein A (e.g. rProtein A-SEPHAROSE, GE Healthcare). More specifically, the genetic manipulation performed in the commercial recombinant protein A product is aimed at facilitating the attachment thereof to a support and at increasing the productivity of the ligand.

These applications, like other affinity chromatography applications, require comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product, in order to regenerate the matrix before subsequent use. Such removal usually involves a procedure known as cleaning-in-place (CIP), wherein agents capable of eluting contaminants from the stationary phase are used. One such class of agents often used is alkaline solutions that are passed over said stationary phase. At present the most extensively used cleaning and sanitizing agent is NaOH, and the concentration thereof can range from 0.1 up to e.g. 1 M, depending on the degree and nature of contamination. This strategy is associated with exposing the matrix to solutions with pH-values above 13. For many affinity chromatography matrices containing proteinaceous affinity ligands such alkaline environment is a very harsh condition and consequently results in decreased capacities owing to instability of the ligand to the high pH involved.

An extensive research has therefore been focused on the development of engineered protein ligands that exhibit an improved capacity to withstand alkaline pH-values. For example, Gulich et al. (Susanne Gulich, Martin Linhult, Per-Ake Nygren, Mathias Uhlén, Sophia Hober, Journal of Biotechnology 80 (2000), 169-178) suggested protein engineering to improve the stability properties of a Streptococcal albumin-binding domain (ABD) in alkaline environments. Gulich et al. created a mutant of ABD, wherein all the four asparagine residues have been replaced by leucine (one residue), aspartate (two residues) and lysine (one residue). Further, Gulich et al. report that their mutant exhibits a target protein binding behavior similar to that of the native protein, and that affinity columns containing the engineered ligand show higher binding capacities after repeated exposure to alkaline conditions than columns prepared using the parental non-engineered ligand. Thus, it is concluded therein that all four asparagine residues can be replaced without any significant effect on structure and function.

Recent work shows that changes can also be made to protein A (SpA) to effect similar properties. US patent application publication US 2005/0143566, which is hereby incorporated by reference in its entirety, discloses that when at least one asparagine residue is mutated to an amino acid other than glutamine or aspartic acid, the mutation confers an increased chemical stability at pH-values of up to about 13-14 compared to the parental SpA, such as the B-domain of SpA, or Protein Z, a synthetic construct derived from the B-domain of SpA (U.S. Pat. No. 5,143,844, incorporated by reference in its entirety). The authors show that when these mutated proteins are used as affinity ligands, the separation media as expected can better withstand cleaning procedures using alkaline agents. Further mutations of protein A domains with the purpose of increasing the alkali stability have also been published in U.S. Pat. No. 8,329,860, JP 2006304633A, U.S. Pat. No. 8,674,073, US 2010/0221844, US 2012/0208234, U.S. Pat. No. 9,051,375, US 2014/0031522, US 2013/0274451 and WO 2014/146350, all of which are hereby incorporated by reference in their entireties. However, the currently available mutants are still sensitive to alkaline pH and the NaOH concentration during cleaning is usually limited to 0.1 M, which means that complete cleaning is difficult to achieve. Higher NaOH concentrations, which would improve the cleaning, lead to unacceptable capacity losses.

There is thus still a need in this field to obtain a separation matrix containing protein ligands having a further improved stability towards alkaline cleaning procedures. There is also a need for such separation matrices with an improved binding capacity to allow for economically efficient purification of therapeutic antibodies.

SUMMARY OF THE INVENTION

One aspect of the invention is to provide a polypeptide with improved alkaline stability. This is achieved with an Fc-binding polypeptide comprising a mutant of a parental Fc-binding domain of *Staphylococcus* Protein A (SpA), as defined by, or having at least 80% such as at least 90%, 95% or 98% identity to, SEQ ID NO: 1, SEQ ID NO: 2, SEQ ID NO:3, SEQ ID NO: 4, SEQ ID NO: 5, SEQ ID NO:6, SEQ ID NO:7, SEQ ID NO:22, SEQ ID NO:51 or SEQ ID NO:52, wherein at least the asparagine or serine residue at the position corresponding to position 11 in SEQ ID NO:4-7 has been mutated to an amino acid selected from the group consisting of glutamic acid, lysine, tyrosine, threonine, phenylalanine, leucine, isoleucine, tryptophan, methionine, valine, alanine, histidine and arginine. Alternatively, the polypeptide comprises a sequence as defined by, or having at least 80% or at least 90%, 95% or 98% identity to SEQ ID NO:53.

$X_1Q$ $X_2AFYEILX_3LP$ $NLTEEQRX_4X_5F$ $IX_6X_7LKDX_8PSX_9$ $SX_{10}X_{11}X_{12}LAEAKX_{13}X_{14}NX_{15}AQ$ (SEQ ID NO:53)

wherein individually of each other:
  $X_1$=A or Q or is deleted
  $X_2$=E, K, Y, T, F, L, W, I, M, V, A, H or R
  $X_3$=H or K
  $X_4$=A or N
  $X_5$=A, G, S, Y, Q, T, N, F, L, W, I, M, V, D, E, H, R or K
  $X_6$=Q or E
  $X_7$=S or K
  $X_8$=E or D
  $X_9$=Q or V or is deleted
  $X_{10}$=K, R or A or is deleted
  $X_{11}$=A, E or N or is deleted
  $X_{12}$=I or L
  $X_{13}$=K or R
  $X_{14}$=L or Y
  $X_{15}$=D, F, Y, W, K or R One advantage is that the alkaline stability is improved over the parental polypeptides, with a maintained highly selective binding towards immunoglobulins and other Fc-containing proteins.

A second aspect of the invention is to provide a multimer with improved alkaline stability, comprising a plurality of polypeptides. This is achieved with a multimer of the polypeptide disclosed above.

A third aspect of the invention is to provide a nucleic acid or a vector encoding a polypeptide or multimer with improved alkaline stability. This is achieved with a nucleic acid or vector encoding a polypeptide or multimer as disclosed above.

A fourth aspect of the invention is to provide an expression system capable of expressing a polypeptide or multimer with improved alkaline stability. This is achieved with an expression system comprising a nucleic acid or vector as disclosed above.

A fifth aspect of the invention is to provide a separation matrix capable of selectively binding immunoglobulins and other Fc-containing proteins and exhibiting an improved alkaline stability. This is achieved with a separation matrix comprising at least 11 mg/ml Fc-binding ligands covalently coupled to a porous support, wherein:
  a) the ligands comprise multimers of alkali-stabilized Protein A domains,
  b) the porous support comprises cross-linked polymer particles having a volume-weighted median diameter (d50,v) of 56-70 micrometers and a dry solids weight of 55-80 mg/ml. Alternatively, it is achieved with a separation matrix comprising at least 15 mg/ml Fc-binding ligands covalently coupled to a porous support, wherein said ligands comprise multimers of alkali-stabilized Protein A domains.

One advantage is that a high dynamic binding capacity is provided. A further advantage is that a high degree of alkali stability is achieved.

A sixth aspect of the invention is to provide an efficient and economical method of isolating an immunoglobulin or other Fc-containing protein. This is achieved with a method comprising the steps of:
  a) contacting a liquid sample comprising an immunoglobulin with a separation matrix as disclosed above,
  b) washing the separation matrix with a washing liquid,
  c) eluting the immunoglobulin from the separation matrix with an elution liquid, and
  d) cleaning the separation matrix with a cleaning liquid.

Further suitable embodiments of the invention are described in the dependent claims. Co-pending applications PCT EP2015/076639, PCT EP2015/076642, GB 1608229.9 and GB 1608232.3 are hereby incorporated by reference in their entireties.

Definitions

The terms "antibody" and "immunoglobulin" are used interchangeably herein, and are understood to include also fragments of antibodies, fusion proteins comprising antibodies or antibody fragments and conjugates comprising antibodies or antibody fragments.

The terms an "Fc-binding polypeptide" and "Fc-binding protein" mean a polypeptide or protein respectively, capable of binding to the crystallisable part (Fc) of an antibody and includes e.g. Protein A and Protein G, or any fragment or fusion protein thereof that has maintained said binding property.

The term "linker" herein means an element linking two polypeptide units, monomers or domains to each other in a multimer.

The term "spacer" herein means an element connecting a polypeptide or a polypeptide multimer to a support.

The term "% identity" with respect to comparisons of amino acid sequences is determined by standard alignment algorithms such as, for example, Basic Local Alignment Tool (BLAST) described in Altshul et al. (1990) J. Mol. Biol., 215: 403-410. A web-based software for this is freely available from the US National Library of Medicine at blast.ncbi.nlm.nih.gov/Blast.cgi?PROGRAM= blastp&PAGE_TYPE=BlastSearch&LINK_LOC= blasthome. Here, the algorithm "blastp (protein-protein BLAST)" is used for alignment of a query sequence with a subject sequence and determining i.a. the % identity.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF FIGURES

FIG. 1 shows an alignment of the Fc-binding domains as defined by SEQ ID NO:1-7 and 51-52.

DETAILED DESCRIPTION OF EMBODIMENTS

Figure 2:
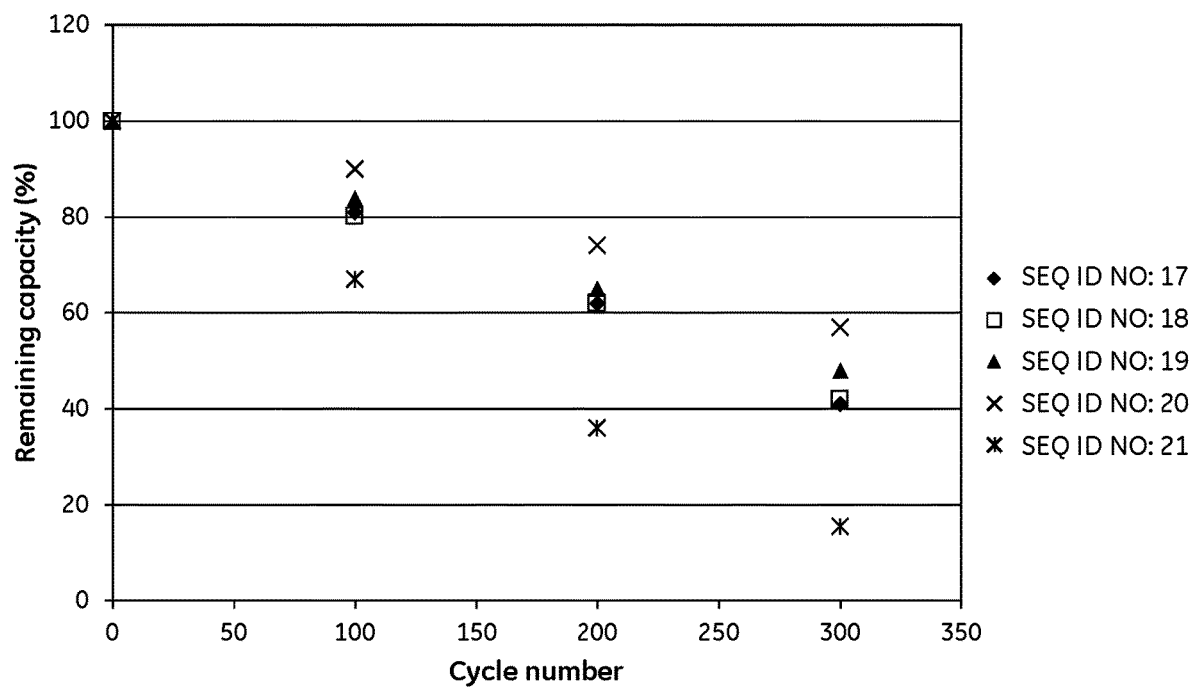
FIG. 2 shows results from Example 2 for the alkali stability of parental and mutated tetrameric Zvar (SEQ ID NO:7) polypeptide variants coupled to an SPR biosensor chip.

In one aspect the present invention discloses an Fc-binding polypeptide, which comprises, or consists essentially of, a mutant of an Fc-binding domain of *Staphylococcus* Protein A (SpA), as defined by, or having at least 90%, at least 95% or at least 98% identity to, SEQ ID NO:1 (E-domain), SEQ ID NO:2 (D-domain), SEQ ID NO:3 (A-domain), SEQ ID NO:22 (variant A-domain), SEQ ID NO:4 (B-domain), SEQ ID NO:5 (C-domain), SEQ ID NO:6 (Protein Z), SEQ ID NO:7 (Zvar), SEQ ID NO:51 (Zvar without the linker region amino acids 1-8 and 56-58) or SEQ ID NO:52 (C-domain without the linker region amino acids 1-8 and 56-58) as illustrated in FIG. 1, wherein at least the asparagine (or serine, in the case of SEQ ID NO:2) residue at the position* corresponding to position 11 in SEQ ID NO:4-7 has been mutated to an amino acid selected from the group consisting of glutamic acid, lysine, tyrosine, threonine, phenylalanine, leucine, isoleucine, tryptophan, methionine, valine, alanine, histidine and arginine. Protein Z (SEQ ID NO:6) is a mutated B-domain as disclosed in U.S. Pat. No. 5,143,844, hereby incorporated by reference in its entirety, while SEQ ID NO:7 denotes a further mutated variant of Protein Z, here called Zvar, with the mutations N3A,N6D,N23T. SEQ ID NO:22 is a natural variant of the A-domain in Protein A from *Staphylococcus aureus* strain N315, having an A46S mutation, using the position terminology of FIG. 1. The mutation of N11 in these domains confers an improved alkali stability in comparison with the parental domain/polypeptide, without impairing the immunoglobulin-binding properties. Hence, the polypeptide can also be described as an Fc- or immunoglobulin-binding polypeptide, or alternatively as an Fc- or immunoglobulin-binding polypeptide unit.

*Throughout this description, the amino acid residue position numbering convention of FIG. 1 is used, and the position numbers are designated as corresponding to those in SEQ ID NO:4-7. This applies also to multimers, where the position numbers designate the positions in the polypeptide units or monomers according to the convention of FIG. 1.

SEQ ID NO:51 (truncated Zvar)
QQ NAFYEILHLP NLTEEQRNAF IQSLKDDPSQ SANLLAEAKK LNDAQ SEQ ID NO:52 (truncated C domain)
QQ NAFYEILHLP NLTEEQRNGF IQSLKDDPSV SKEILAEAKK LNDAQ In alternative language, the invention discloses an Fc-binding polypeptide which comprises a sequence as defined by, or having at least 90%, at least 95% or at least 98% identity to SEQ ID NO:53.

SEQ ID NO:53
$X_1Q$ $X_2AFYEILX_3LP$ $NLTEEQRX_4X_5F$ $IX_6X_7LKDX_8PSX_9$ $SX_{10}X_{11}X_{12}LAEAKX_{13}X_{14}NX_{15}AQ$ wherein individually of each other:
$X_1$=A, Q or is deleted
$X_2$=E, K, Y, T, F, L, W, I, M, V, A, H or R
$X_3$=H or K
$X_4$=A or N
$X_5$=A, G, S, Y, Q, T, N, F, L, W, I, M, V, D, E, H, R or K, such as S, Y, Q, T, N, F, L, W, I, M, V, D, E, H, R or K
$X_6$=Q or E
$X_7$=S or K
$X_8$=E or D
$X_9$=Q, V or is deleted
$X_{10}$=K, R, A or is deleted
$X_{11}$=A, E, N or is deleted
$X_{12}$=I or L
$X_{13}$=K or R
$X_{14}$=L or Y
$X_{15}$=D, F, Y, W, K or R Specifically, the amino acid residues in SEQ ID NO:53 may individually of each other be:
$X_1$=A or is deleted
$X_2$=E
$X_3$=H
$X_4$=N
$X_6$=Q
$X_7$=S
$X_8$=D $X_9$=V or is deleted
$X_{10}$=K or is deleted
$X_{11}$=A or is deleted
$X_{12}$=I
$X_{13}$=K
$X_{14}$=L.

In certain embodiments, the amino acid residues in SEQ ID NO:53 may be: $X_1$=A, $X_2$=E, $X_3$=H, $X_4$=N, $X_6$=Q, $X_7$=S, $X_8$=D, $X_9$=V, $X_{10}$=K, $X_{11}$=A, $X_{12}$=I, $X_{13}$=K, $X_{14}$=L. In some embodiments $X_2$=E, $X_3$=H, $X_4$=N, $X_5$=A, $X_6$=Q, $X_7$=S, $X_8$=D, $X_{12}$=I, $X_{13}$=K, $X_{14}$=L and $X_{15}$=D and one or more of $X_1$, $X_9$, $X_{10}$ and $X_{11}$ is deleted. In further embodiments, $X_1$=A, $X_2$=E, $X_3$=H, $X_4$=N, $X_5$=S, Y, Q, T, N, F, L, W, I, M, V, D, E, H, R or K, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D, or alternatively $X_1$=A, $X_2$=E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=F, Y, W, K or R.

The N11 ($X_2$) mutation (e.g. a N11E or N11K mutation) may be the only mutation or the polypeptide may also comprise further mutations, such as substitutions in at least one of the positions corresponding to positions 3, 6, 9, 10, 15, 18, 23, 28, 29, 32, 33, 36, 37, 40, 42, 43, 44, 47, 50, 51, 55 and 57 in SEQ ID NO:4-7. In one or more of these positions, the original amino acid residue may e.g. be substituted with an amino acid which is not asparagine, proline or cysteine. The original amino acid residue may e.g. be substituted with an alanine, a valine, a threonine, a serine, a lysine, a glutamic acid or an aspartic acid. Further, one or more amino acid residues may be deleted, e.g. from positions 1-6 and/or from positions 56-58.

In some embodiments, the amino acid residue at the position corresponding to position 9 in SEQ ID NO:4-7 ($X_1$) is an amino acid other than glutamine, asparagine, proline or cysteine, such as an alanine or it can be deleted. The combination of the mutations at positions 9 and 11 provides particularly good alkali stability, as shown by the examples. In specific embodiments, in SEQ ID NO: 7 the amino acid residue at position 9 is an alanine and the amino acid residue at position 11 is a lysine or glutamic acid, such as a lysine. Mutations at position 9 are also discussed in copending application PCT/SE2014/050872, which is hereby incorporated by reference in its entirety.

In some embodiments, the amino acid residue at the position corresponding to position 50 in SEQ ID NO:4-7 ($X_{13}$) is an arginine or a glutamic acid.

In certain embodiments, the amino acid residue at the position corresponding to position 3 in SEQ ID NO:4-7 is an alanine and/or the amino acid residue at the position corresponding to position 6 in SEQ ID NO:4-7 is an aspartic acid. One of the amino acid residues at positions 3 and 6 may be an asparagine and in an alternative embodiment both amino acid residues at positions 3 and 6 may be asparagines.

In some embodiments the amino acid residue at the position corresponding to position 43 in SEQ ID NO:4-7 ($X_{11}$) is an alanine or a glutamic acid, such as an alanine or it can be deleted. In specific embodiments, the amino acid residues at positions 9 and 11 in SEQ ID NO: 7 are alanine and lysine/glutamic acid respectively, while the amino acid residue at position 43 is alanine or glutamic acid.

In certain embodiments the amino acid residue at the position corresponding to position 28 in SEQ ID NO:4-7 ($X_5$) is an alanine or an asparagine, such as an alanine.

In some embodiments the amino acid residue at the position corresponding to position 40 in SEQ ID NO:4-7 ($X_9$) is selected from the group consisting of asparagine, alanine, glutamic acid and valine, or from the group consisting of glutamic acid and valine or it can be deleted. In specific embodiments, the amino acid residues at positions 9 and 11 in SEQ ID NO: 7 are alanine and glutamic acid respectively, while the amino acid residue at position 40 is valine. Optionally, the amino acid residue at position 43 may then be alanine or glutamic acid.

In certain embodiments, the amino acid residue at the position corresponding to position 42 in SEQ ID NO:4-7 ($X_{10}$) is an alanine, lysine or arginine or it can be deleted.

In some embodiments the amino acid residue at the position corresponding to position 18 in SEQ ID NO:4-7 ($X_3$) is a lysine or a histidine, such as a lysine.

In certain embodiments the amino acid residue at the position corresponding to position 33 in SEQ ID NO:4-7 ($X_7$) is a lysine or a serine, such as a lysine. In some embodiments the amino acid residue at the position corresponding to position 37 in SEQ ID NO:4-7 ($X_8$) is a glutamic acid or an aspartic acid, such as a glutamic acid.

In certain embodiments the amino acid residue at the position corresponding to position 51 in SEQ ID NO:4-7 ($X_{14}$) is a tyrosine or a leucine, such as a tyrosine.

In some embodiments, the amino acid residue at the position corresponding to position 44 in SEQ ID NO:4-7 ($X_{12}$) is a leucine or an isoleucine. In specific embodiments, the amino acid residues at positions 9 and 11 in SEQ ID NO: 7 are alanine and lysine/glutamic acid respectively, while the amino acid residue at position 44 is isoleucine. Optionally, the amino acid residue at position 43 may then be alanine or glutamic acid.

In some embodiments, the amino acid residues at the positions corresponding to positions 1, 2, 3 and 4 or to positions 3, 4, 5 and 6 in SEQ ID NO: 4-7 have been deleted. In specific variants of these embodiments, the parental polypeptide is the C domain of Protein A (SEQ ID NO: 5). The effects of these deletions on the native C domain are described in U.S. Pat. Nos. 9,018,305 and 8,329,860, which are hereby incorporated by reference in their entireties.

In certain embodiments, the mutation in SEQ ID NO:4-7, such as in SEQ ID NO:7, is selected from the group consisting of: N11K; N11E; N11Y; N11T; N11F; N11L; N11W; N11I; N11M; N11V; N11A; N11H; N11R; N11E, Q32A; N11E,Q32E,Q40E; N11E,Q32E,K50R; Q9A,N11E, N43A; Q9A,N11E,N28A,N43A; Q9A,N11E,Q40V,A42K, N43E,L44I; Q9A,N11E,Q40V,A42K,N43A,L44I; N11K, H18K,S33K,D37E,A42R,N43A,L44I,K50R,L51Y; Q9A, N11E,N28A,Q40V,A42K,N43A,L44I; Q9A,N11K,H18K, S33K,D37E,A42R,N43A,L44I,K50R,L51Y; N11K,H18K, D37E,A42R, N43A,L44I; Q9A,N11K,H18K,D37E,A42R, N43A,L44I; Q9A,N11K,H18K,D37E,A42R, N43A,L44I, K50R; Q9A,N11K,H18K,D37E,A42R; Q9A,N11E,D37E, Q40V,A42K,N43A,L44I and Q9A,N11E,D37E,Q40V, A42R,N43A,L44I. These mutations provide particularly high alkaline stabilities. The mutation in SEQ ID NO:4-7, such as in SEQ ID NO:7, can also be selected from the group consisting of N11K; N11Y; N11F; N11L; N11W; N11I; N11M; N11V; N11A; N11H; N11R; Q9A,N11E,N43A; Q9A,N11E,N28A,N43A; Q9A,N11E,Q40V,A42K,N43E, L44I; Q9A,N11E,Q40V,A42K,N43A,L44I; Q9A,N11E, N28A,Q40V,A42K,N43A,L44I; N11K,H18K,S33K,D37E, A42R,N43A,L44I,K50R,L51Y; Q9A,N11K,H18K,S33K, D37E,A42R,N43A,L44I,K50R,L51Y; N11K,H18K,D37E, A42R, N43A,L44I; Q9A,N11K,H18K,D37E,A42R,N43A, L44I and Q9A,N11K,H18K,D37E, A42R,N43A,L44I, K50R.

In some embodiments, the polypeptide comprises or consists essentially of a sequence defined by or having at least 90%, 95% or 98% identity to an amino acid sequence selected from the group consisting of: SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:23, SEQ ID NO:24, SEQ ID NO:25, SEQ ID NO:26, SEQ ID NO:27, SEQ ID NO:28, SEQ ID NO:29, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49 and SEQ ID NO:50. It may e.g. comprise or consist essentially of a sequence defined by or having at least 90%, 95% or 98% identity to an amino acid sequence selected from the group consisting of: SEQ ID NO:8, SEQ ID NO:9, SEQ ID NO:10, SEQ ID NO:11, SEQ ID NO:16, SEQ ID NO:23, SEQ ID NO:24, SEQ ID NO:25, SEQ ID NO:26, SEQ ID NO:27, SEQ ID NO:28 and SEQ ID NO:29. It can also comprise or consist essentially of a sequence defined by or having at least 90%, 95% or 98% identity to an amino acid sequence selected from the group consisting of: SEQ ID NO:8, SEQ ID NO:9, SEQ ID NO:10, SEQ ID NO:11, SEQ ID NO:16, SEQ ID NO:23, SEQ ID NO:24, SEQ ID NO:25, SEQ ID NO:27, SEQ ID NO:28, SEQ ID NO:38, SEQ ID NO:40; SEQ ID NO:41; SEQ ID NO:42; SEQ NO:43, SEQ ID NO:44, SEQ ID NO:45, SEQ ID NO:46, SEQ ID NO:47 and SEQ ID NO:48.

In certain embodiments, the polypeptide comprises or consists essentially of a sequence defined by or having at least 90%, 95% or 98% identity to an amino acid sequence selected from the group consisting of SEQ ID NO:54-70. comprises or consists essentially of a sequence defined by or having at least 90%, 95% or 98% identity to an amino acid sequence selected from the group consisting of SEQ ID NO:71-75, or it may comprise or consist essentially of a sequence defined by or having at least 90%, 95% or 98% identity to an amino acid sequence selected from the group consisting of SEQ ID NO:76-79. It may further comprise or consist essentially of a sequence defined by or having at least 90%, 95% or 98% identity to an amino acid sequence selected from the group consisting of SEQ ID NO:89-95.

The polypeptide may e.g. be defined by a sequence selected from the groups above or from subsets of these groups, but it may also comprise additional amino acid residues at the N- and/or C-terminal end, e.g. a leader sequence at the N-terminal end and/or a tail sequence at the C-terminal end.

```
Zvar (Q9A, N11E, N43A)
                                                                          SEQ ID NO: 8
VDAKFDKEAQ EAFYEILHLP NLTEEQRNAF IQSLKDDPSQ SAALLAEAKK
LNDAQAPK Zvar (Q9A, N11E, N28A, N43A)
                                                                          SEQ ID NO: 9
VDAKFDKEAQ EAFYEILHLP NLTEEQRAAF IQSLKDDPSQ SAALLAEAKK
LNDAQAPK Zvar (Q9A, N11E, Q40V, A42K, N43E, L44I)
                                                                          SEQ ID NO: 10
VDAKFDKEAQ EAFYEILHLP NLTEEQRNAF IQSLKDDPSV SKEILAEAKK
LNDAQAPK Zvar (Q9A, N11E, Q40V, A42K, N43A, L44I)
                                                                          SEQ ID NO: 11
VDAKFDKEAQ EAFYEILHLP NLTEEQRNAF IQSLKDDPSV SKAILAEAKK
LNDAQAPK Zvar (N11E, Q32A)
                                                                          SEQ ID NO: 12
VDAKFDKEQQ EAFYEILHLP NLTEEQRNAF IASLKDDPSQ SANLLAEAKK
LNDAQAPK Zvar (N11E)
                                                                          SEQ ID NO: 13
VDAKFDKEQQ EAFYEILHLP NLTEEQRNAF IQSLKDDPSQ SANLLAEAKK
LNDAQAPK Zvar (N11E, Q32E, Q40E)
                                                                          SEQ ID NO: 14
VDAKFDKEQQ EAFYEILHLP NLTEEQRNAF IESLKDDPSE SANLLAEAKK
LNDAQAPK Zvar (N11E, Q32E, K50R)
                                                                          SEQ ID NO: 15
VDAKFDKEQQ EAFYEILHLP NLTEEQRNAF IESLKDDPSQ SANLLAEAKR
LNDAQAPK Zvar (N11K)
                                                                          SEQ ID NO: 16
VDAKFDKEQQ KAFYEILHLP NLTEEQRNAF IQSLKDDPSQ SANLLAEAKK
LNDAQAPK Zvar (N11K, H18K, S33K, D37E, A42R, N43A, L44I, K50R, L51Y)
                                                                          SEQ ID NO: 23
VDAKFDKEQQ KAFYEILKLP NLTEEQRNAF IQKLKDEPSQ SRAILAEAKR
YNDAQAPK
```

-continued

Zvar (Q9A, N11E, N28A, Q40V, A42K, N43A, L44I)

VDAKFDKEAQ EAFYEILHLP NLTEEQRAAF IQSLKDDPSV SKAILAEAKK
LNDAQAPK

SEQ ID NO: 24

Zvar (Q9A, N11K, H18K, S33K, D37E, A42R, N43A, L44I, K50R, L51Y)

VDAKFDKEAQ KAFYEILKLP NLTEEQRAAF IQKLKDEPSQ SRAILAEAKR
YNDAQAPK

SEQ ID NO: 25

Zvar (N11K, H18K, D37E, A42R, N43A, L44I)

VDAKFDKEQQ KAFYEILKLP NLTEEQRNAF IQSLKDEPSQ SRAILAEAKK
LNDAQAPK

SEQ ID NO: 26

Zvar (Q9A, N11K, H18K, D37E, A42R, N43A, L44I)

VDAKFDKEAQ KAFYEILKLP NLTEEQRNAF IQSLKDEPSQ SRAILAEAKK
LNDAQAPK

SEQ ID NO: 27

Zvar (Q9A, N11K, H18K, D37E, A42R, N43A, L44I, K50R)

VDAKFDKEAQ KAFYEILKLP NLTEEQRNAF IQSLKDEPSQ SRAILAEAKR
LNDAQAPK

SEQ ID NO: 28

Zvar (Q9A, N11K, H18K, D37E, A42R)

VDAKFDKEAQ KAFYEILKLP NLTEEQRNAF IQSLKDEPSQ SRNLLAEAKK
LNDAQAPK

SEQ ID NO: 29

B (Q9A, N11E, Q40V, A42K, N43A, L44I)

ADNKFNKEAQ EAFYEILHLP NLNEEQRNGF IQSLKDDPSV SKAILAEAKK
LNDAQAPK

SEQ ID NO: 36

C (Q9A, N11E, E43A)

ADNKFNKEAQ EAFYEILHLP NLTEEQRNGF IQSLKDDPSV SKAILAEAKK
LNDAQAPK

SEQ ID NO: 37

Zvar (N11Y) SANLLAEAKK

VDAKFDKEQQ YAFYEILHLP NLTEEQRNAF IQSLKDDPSQ
LNDAQAPK

SEQ ID NO: 38

Zvar (N11T)

VDAKFDKEQQ TAFYEILHLP NLTEEQRNAF IQSLKDDPSQ SANLLAEAKK
LNDAQAPK

SEQ ID NO: 39

Zvar (N11F)

VDAKFDKEQQ FAFYEILHLP NLTEEQRNAF IQSLKDDPSQ SANLLAEAKK
LNDAQAPK

SEQ ID NO: 40

Zvar (N11L)

VDAKFDKEQQ LAFYEILHLP NLTEEQRNAF IQSLKDDPSQ SANLLAEAKK
LNDAQAPK

SEQ ID NO: 41

Zvar (N11W)

VDAKFDKEQQ WAFYEILHLP NLTEEQRNAF IQSLKDDPSQ SANLLAEAKK
LNDAQAPK

SEQ ID NO: 42

Zvar (N11I)

VDAKFDKEQQ IAFYEILHLP NLTEEQRNAF IQSLKDDPSQ SANLLAEAKK
LNDAQAPK

SEQ ID NO: 43

Zvar (N11M)

VDAKFDKEQQ MAFYEILHLP NLTEEQRNAF IQSLKDDPSQ SANLLAEAKK
LNDAQAPK

SEQ ID NO: 44

Zvar (N11V)

VDAKFDKEQQ VAFYEILHLP NLTEEQRNAF IQSLKDDPSQ SANLLAEAKK
LNDAQAPK

SEQ ID NO: 45

-continued

Zvar (N11A)

VDAKFDKEQQ AAFYEILHLP NLTEEQRNAF IQSLKDDPSQ SANLLAEAKK LNDAQAPK

SEQ ID NO: 46

Zvar (N11H)

VDAKFDKEQQ HAFYEILHLP NLTEEQRNAF IQSLKDDPSQ SANLLAEAKK LNDAQAPK

SEQ ID NO: 47

Zvar (N11R)

VDAKFDKEQQ RAFYEILHLP NLTEEQRNAF IQSLKDDPSQ SANLLAEAKK LNDAQAPK

SEQ ID NO: 48

Zvar (Q9A, N11E, D37E, Q40V, A42K, N43A, L44I)

VDAKFDKEAQ EAFYEILHLP NLTEEQRNAF IQSLKDEPSV SKAILAEAKK LNDAQAPK

SEQ ID NO: 49

Zvar (Q9A, N11E, D37E, Q40V, A42R, N43A, L44I)

VDAKFDKEAQ EAFYEILHLP NLTEEQRNAF IQSLKDEPSV SRAILAEAKK LNDAQAPK

SEQ ID NO: 50

Zvar (Q9A, N11E, A29G, Q40V, A42K, N43A, L44I)

VDAKFDKEAQ EAFYEILHLP NLTEEQRNGF IQSLKDDPSV SKAILAEAKK LNDAQAPK

SEQ ID NO: 54

Zvar (Q9A, N11E, A29S, Q40V, A42K, N43A, L44I)

VDAKFDKEAQ EAFYEILHLP NLTEEQRNSF IQSLKDDPSV SKAILAEAKK LNDAQAPK

SEQ ID NO: 55

Zvar (Q9A, N11E, A29Y, Q40V, A42K, N43A, L44I)

VDAKFDKEAQ EAFYEILHLP NLTEEQRNYF IQSLKDDPSV SKAILAEAKK LNDAQAPK

SEQ ID NO: 56

Zvar (Q9A, N11E, A29Q, Q40V, A42K, N43A, L44I)

VDAKFDKEAQ EAFYEILHLP NLTEEQRNQF IQSLKDDPSV SKAILAEAKK LNDAQAPK

SEQ ID NO: 57

Zvar (Q9A, N11E, A29T, Q40V, A42K, N43A, L44I)

VDAKFDKEAQ EAFYEILHLP NLTEEQRNTF IQSLKDDPSV SKAILAEAKK LNDAQAPK

SEQ ID NO: 58

Zvar (Q9A, N11E, A29N, Q40V, A42K, N43A, L44I)

VDAKFDKEAQ EAFYEILHLP NLTEEQRNNF IQSLKDDPSV SKAILAEAKK LNDAQAPK

SEQ ID NO: 59

Zvar (Q9A, N11E, A29F, Q40V, A42K, N43A, L44I)

VDAKFDKEAQ EAFYEILHLP NLTEEQRNFF IQSLKDDPSV SKAILAEAKK LNDAQAPK

SEQ ID NO: 60

Zvar (Q9A, N11E, A29L, Q40V, A42K, N43A, L44I)

VDAKFDKEAQ EAFYEILHLP NLTEEQRNLF IQSLKDDPSV SKAILAEAKK LNDAQAPK

SEQ ID NO: 61

Zvar (Q9A, N11E, A29W, Q40V, A42K, N43A, L44I)

VDAKFDKEAQ EAFYEILHLP NLTEEQRNWF IQSLKDDPSV SKAILAEAKK LNDAQAPK

SEQ ID NO: 62

Zvar (Q9A, N11E, A29I, Q40V, A42K, N43A, L44I)

VDAKFDKEAQ EAFYEILHLP NLTEEQRNIF IQSLKDDPSV SKAILAEAKK LNDAQAPK

SEQ ID NO: 63

Zvar (Q9A, N11E, A29M, Q40V, A42K, N43A, L44I)

VDAKFDKEAQ EAFYEILHLP NLTEEQRNMF IQSLKDDPSV SKAILAEAKK LNDAQAPK

SEQ ID NO: 64

Zvar (Q9A, N11E, A29V, Q40V, A42K, N43A, L44I)

SEQ ID NO: 65

VDAKFDKEAQ EAFYEILHLP NLTEEQRNVF IQSLKDDPSV SKAILAEAKK LNDAQAPK

Zvar (Q9A, N11E, A29D, Q40V, A42K, N43A, L44I)

SEQ ID NO: 66

VDAKFDKEAQ EAFYEILHLP NLTEEQRNDF IQSLKDDPSV SKAILAEAKK LNDAQAPK

Zvar (Q9A, N11E, A29E, Q40V, A42K, N43A, L44I)

SEQ ID NO: 67

VDAKFDKEAQ EAFYEILHLP NLTEEQRNEF IQSLKDDPSV SKAILAEAKK LNDAQAPK

Zvar (Q9A, N11E, A29H, Q40V, A42K, N43A, L44I)

SEQ ID NO: 68

VDAKFDKEAQ EAFYEILHLP NLTEEQRNHF IQSLKDDPSV SKAILAEAKK LNDAQAPK

Zvar (Q9A, N11E, A29R, Q40V, A42K, N43A, L44I)

SEQ ID NO: 69

VDAKFDKEAQ EAFYEILHLP NLTEEQRNRF IQSLKDDPSV SKAILAEAKK LNDAQAPK

Zvar (Q9A, N11E, A29K, Q40V, A42K, N43A, L44I)

SEQ ID NO: 70

VDAKFDKEAQ EAFYEILHLP NLTEEQRNKF IQSLKDDPSV SKAILAEAKK LNDAQAPK

Zvar (Q9A, N11E, Q40V, A42K, N43A, L44I, D53F)

SEQ ID NO: 71

VDAKFDKEAQ EAFYEILHLP NLTEEQRNAF IQSLKDDPSV SKAILAEAKK LNFAQAPK

Zvar (Q9A, N11E, Q40V, A42K, N43A, L44I, D53Y)

SEQ ID NO: 72

VDAKFDKEAQ EAFYEILHLP NLTEEQRNAF IQSLKDDPSV SKAILAEAKK LNYAQAPK

Zvar (Q9A, N11E, Q40V, A42K, N43A, L44I, D53W)

SEQ ID NO: 73

VDAKFDKEAQ EAFYEILHLP NLTEEQRNAF IQSLKDDPSV SKAILAEAKK LNWAQAPK

Zvar (Q9A, N11E, Q40V, A42K, N43A, L44I, D53K)

SEQ ID NO: 74

VDAKFDKEAQ EAFYEILHLP NLTEEQRNAF IQSLKDDPSV SKAILAEAKK LNKAQAPK

Zvar (Q9A, N11E, Q40V, A42K, N43A, L44I, D53R)

SEQ ID NO: 75

VDAKFDKEAQ EAFYEILHLP NLTEEQRNAF IQSLKDDPSV SKAILAEAKK LNRAQAPK

Zvar (Q9del, N11E, Q40V, A42K, N43A, L44I)

SEQ ID NO: 76

VDAKFDKE_Q EAFYEILHLP NLTEEQRNAF IQSLKDDPSV SKAILAEAKK LNDAQAPK

Zvar (Q9A, N11E, Q40del, A42K, N43A, L44I)

SEQ ID NO: 77

VDAKFDKEAQ EAFYEILHLP NLTEEQRNAF IQSLKDDPS_ SKAILAEAKK LNDAQAPK

Zvar (Q9A, N11E, Q40V, A42del, N43A, L44I)

SEQ ID NO: 78

VDAKFDKEAQ EAFYEILHLP NLTEEQRNAF IQSLKDDPSV S_AILAEAKK LNDAQAPK

Zvar (Q9A, N11E, Q40V, A42K, N43del, L44I)

SEQ ID NO: 79

VDAKFDKEAQ EAFYEILHLP NLTEEQRNAF IQSLKDDPSV SK_ILAEAKK LNDAQAPK

Zvar (D2del, A3del, K4del, Q9A, N11E, Q40V, A42K, N43A, L44I)

SEQ ID NO: 89

V___FDKEAQ EAFYEILHLP NLTEEQRNAF IQSLKDDPSV SKAILAEAKK LNDAQAPK

-continued

```
Zvar (V1del, D2del, Q9A, N11E, Q40V, A42K, N43A, L44I, K58del)
                                                                          SEQ ID NO: 90
__AKFDKEAQ EAFYEILHLP NLTEEQRNAF IQSLKDDPSV SKAILAEAKK
LNDAQAP_

Zvar (K4del, F5del, D6del, K7del, E8del, Q9A, N11E, Q40V, A42K, N43A, L44I)
                                                                          SEQ ID NO: 91
VDA_____AQ EAFYEILHLP NLTEEQRNAF IQSLKDDPSV SKAILAEAKK
LNDAQAPK Zvar (Q9A, N11E, Q40V, A42K, N43A, L44I, A56del, P57del, K58del)
                                                                          SEQ ID NO: 92
VDAKFDKEAQ EAFYEILHLP NLTEEQRNAF IQSLKDDPSV SKAILAEAKK
LNDAQ Zvar (V1del,, D2del, A3del, Q9A, N11E, Q40V, A42K, N43A, L44I)
                                                                          SEQ ID NO: 93
___KFDKEAQ EAFYEILHLP NLTEEQRNAF IQSLKDDPSV SKAILAEAKK
LNDAQAPK Zvar (V1del, D2del, A3del, K4del, F5del, D6del, K7del, E8del, Q9A, N11E, Q40V, A42K,
N43A, L44I)
                                                                          SEQ ID NO: 94
_____AQ EAFYEILHLP NLTEEQRNAF IQSLKDDPSV SKAILAEAKK LNDAQAPK Zvar (Q9A, N11E, Q40V, A42K, N43A, L441, K58_insYEDG)
                                                                          SEQ ID NO: 95
VDAKFDKEAQ EAFYEILHLP NLTEEQRNAF IQSLKDDPSV SKAILAEAKK
LNDAQAPKYE DG
```

In a second aspect the present invention discloses a multimer comprising, or consisting essentially of, a plurality of polypeptide units as defined by any embodiment disclosed above. The use of multimers may increase the immunoglobulin binding capacity and multimers may also have a higher alkali stability than monomers. The multimer can e.g. be a dimer, a trimer, a tetramer, a pentamer, a hexamer, a heptamer, an octamer or a nonamer. It can be a homomultimer, where all the units in the multimer are identical or it can be a heteromultimer, where at least one unit differs from the others. Advantageously, all the units in the multimer are alkali stable, such as by comprising the mutations disclosed above. The polypeptides can be linked to each other directly by peptide bonds between the C-terminal and N-terminal ends of the polypeptides. Alternatively, two or more units in the multimer can be linked by linkers comprising oligomeric or polymeric species, such as linkers comprising peptides with up to 25 or 30 amino acids, such as 3-25 or 3-20 amino acids. The linkers may e.g. comprise or consist essentially of a peptide sequence defined by, or having at least 90% identity or at least 95% identity, with an amino acid sequence selected from the group consisting of APKVDAKFDKE (SEQ ID NO:96), APKVDNKFNKE (SEQ ID NO:97), APKADNKFNKE (SEQ ID NO:98), APKVFDKE (SEQ ID NO:99), APAKFDKE (SEQ ID NO:100), AKFDKE (SEQ ID NO:101), APKVDA (SEQ ID NO:102), VDAKFDKE (SEQ ID NO:103), APKKFDKE (SEQ ID NO:104), APK, APKYEDGVDAKFDKE (SEQ ID NO:105) and YEDG (SEQ ID NO:106). They can also consist essentially of a peptide sequence defined by or having at least 90% identity or at least 95% identity with an amino acid sequence selected from the group consisting of APKADNKFNKE (SEQ ID NO:98), APKVFDKE (SEQ ID NO:99), APAKFDKE (SEQ ID NO:100), AKFDKE (SEQ ID NO:101), APKVDA (SEQ ID NO:102), VDAKFDKE (SEQ ID NO:103), APKKFDKE (SEQ ID NO:104), APK and APKYEDGVDAKFDKE (SEQ ID NO:105). In some embodiments the linkers do not consist of the peptides APKVDAKFDKE (SEQ ID NO:96) or APKVDNKFNKE (SEQ ID NO:97), or alternatively do not consist of the peptides APKVDAKFDKE (SEQ ID NO:96), APKVDNKFNKE (SEQ ID NO:97).

The nature of such a linker should preferably not destabilize the spatial conformation of the protein units. This can e.g. be achieved by avoiding the presence of proline in the linkers. Furthermore, said linker should preferably also be sufficiently stable in alkaline environments not to impair the properties of the mutated protein units. For this purpose, it is advantageous if the linkers do not contain asparagine. It can additionally be advantageous if the linkers do not contain glutamine. The multimer may further at the N-terminal end comprise a plurality of amino acid residues e.g. originating from the cloning process or constituting a residue from a cleaved off signaling sequence. The number of additional amino acid residues may e.g. be 20 or less, such as 15 or less, such as 10 or less or 5 or less. As a specific example, the multimer may comprise an AQ, AQGT (SEQ ID NO:107), VDAKFDKE (SEQ ID NO:103), AQVDAKFDKE (SEQ ID NO:108) or AQGTVDAKFDKE (SEQ ID NO:109) sequence at the N-terminal end.

In certain embodiments, the multimer may comprise, or consist essentially, of a sequence selected from the group consisting of: SEQ ID NO:80-87. These and additional sequences are listed below and named as Parent(Mutations)n, where n is the number of monomer units in a multimer.

Zvar (Q9A, N11E, N43A)4

AQGT VDAKFDKEAQ EAFYEILHLP NLTEEQRNAF IQSLKDDPSQ SAALLAEAKK
LNDAQAPK VDAKFDKEAQ EAFYEILHLP NLTEEQRNAF IQSLKDDPSQ
SAALLAEAKK LNDAQAPK VDAKFDKEAQ EAFYEILHLP NLTEEQRNAF
IQSLKDDPSQ SAALLAEAKK LNDAQAPK VDAKFDKEAQ EAFYEILHLP
NLTEEQRNAF IQSLKDDPSQ SAALLAEAKK LNDAQAPKC

SEQ ID NO: 17

Zvar (Q9A, N11E, N28A, N43A)4

AQGT VDAKFDKEAQ EAFYEILHLP NLTEEQRAAF IQSLKDDPSQ SAALLAEAKK
LNDAQAPK VDAKFDKEAQ EAFYEILHLP NLTEEQRAAF IQSLKDDPSQ
SAALLAEAKK LNDAQAPK VDAKFDKEAQ EAFYEILHLP NLTEEQRAAF
IQSLKDDPSQ SAALLAEAKK LNDAQAPK VDAKFDKEAQ EAFYEILHLP
NLTEEQRAAF IQSLKDDPSQ SAALLAEAKK LNDAQAPKC

SEQ ID NO: 18

Zvar (Q9A, N11E, Q40V, A42K, N43E, L44I)4

AQGT VDAKFDKEAQ EAFYEILHLP NLTEEQRNAF IQSLKDDPSV SKEILAEAKK
LNDAQAPK VDAKFDKEAQ EAFYEILHLP NLTEEQRNAF IQSLKDDPSV SKEILAEAKK
LNDAQAPK VDAKFDKEAQ EAFYEILHLP NLTEEQRNAF IQSLKDDPSV SKEILAEAKK
LNDAQAPK VDAKFDKEAQ EAFYEILHLP NLTEEQRNAF IQSLKDDPSV SKEILAEAKK
LNDAQAPKC

SEQ ID NO: 19

Zvar (Q9A, N11E, Q40V, A42K, N43A, L44I)4

AQGT VDAKFDKEAQ EAFYEILHLP NLTEEQRNAF IQSLKDDPSV SKAILAEAKK
LNDAQAPK VDAKFDKEAQ EAFYEILHLP NLTEEQRNAF IQSLKDDPSV SKAILAEAKK
LNDAQAPK VDAKFDKEAQ EAFYEILHLP NLTEEQRNAF IQSLKDDPSV SKAILAEAKK
LNDAQAPK VDAKFDKEAQ EAFYEILHLP NLTEEQRNAF IQSLKDDPSV SKAILAEAKK
LNDAQAPKC

SEQ ID NO: 20

Zvar (N11K, H18K, S33K, D37E, A42R, N43A, L44I, K50R, L51Y)4

AQGT VDAKFDKEQQ KAFYEILKLP NLTEEQRNAF IQKLKDEPSQ SRAILAEAKR
YNDAQAPK VDAKFDKEQQ KAFYEILKLP NLTEEQRNAF IQKLKDEPSQ
SRAILAEAKR YNDAQAPK VDAKFDKEQQ KAFYEILKLP NLTEEQRNAF
IQKLKDEPSQ SRAILAEAKR YNDAQAPK VDAKFDKEQQ KAFYEILKLP
NLTEEQRNAF IQKLKDEPSQ SRAILAEAKR YNDAQAPKC

SEQ ID NO: 30

Zvar (Q9A, N11K, H18K, D37E, A42R)4

AQGT VDAKFDKEAQ KAFYEILKLP NLTEEQRNAF IQSLKDEPSQ SRNLLAEAKK
LNDAQAPK VDAKFDKEAQ KAFYEILKLP NLTEEQRNAF IQSLKDEPSQ
SRNLLAEAKK LNDAQAPK VDAKFDKEAQ KAFYEILKLP NLTEEQRNAF
IQSLKDEPSQ SRNLLAEAKK LNDAQAPK VDAKFDKEAQ KAFYEILKLP
NLTEEQRNAF IQSLKDEPSQ SRNLLAEAKK LNDAQAPKC

SEQ ID NO: 31

Zvar (Q9A, N11E, N28A, Q40V, A42K, N43A, L44I)4

AQGT VDAKFDKEAQ EAFYEILHLP NLTEEQRAAF IQSLKDDPSV SKAILAEAKK
LNDAQAPK VDAKFDKEAQ EAFYEILHLP NLTEEQRAAF IQSLKDDPSV
SKAILAEAKK LNDAQAPK VDAKFDKEAQ EAFYEILHLP NLTEEQRAAF

SEQ ID NO: 32

-continued

IQSLKDDPSV SKAILAEAKK LNDAQAPK VDAKFDKEAQ EAFYEILHLP

NLTEEQRAAF IQSLKDDPSV SKAILAEAKK LNDAQAPKC

Zvar (Q9A, N11E, Q40V, A42K, N43A, L44I)6
SEQ ID NO: 33

AQGT VDAKFDKEAQ EAFYEILHLP NLTEEQRNAF IQSLKDDPSV SKAILAEAKK

LNDAQAPK VDAKFDKEAQ EAFYEILHLP NLTEEQRNAF IQSLKDDPSV SKAILAEAKK

LNDAQAPK VDAKFDKEAQ EAFYEILHLP NLTEEQRNAF IQSLKDDPSV SKAILAEAKK

LNDAQAPK VDAKFDKEAQ EAFYEILHLP NLTEEQRNAF IQSLKDDPSV SKAILAEAKK

LNDAQAPK VDAKFDKEAQ EAFYEILHLP NLTEEQRNAF IQSLKDDPSV SKAILAEAKK

LNDAQAPK VDAKFDKEAQ EAFYEILHLP NLTEEQRNAF IQSLKDDPSV SKAILAEAKK

LNDAQAPKC

Zvar (Q9A, N11E, D37E, Q40V, A42K, N43A, L44I)4
SEQ ID NO: 34

AQGT VDAKFDKEAQ EAFYEILHLP NLTEEQRNAF IQSLKDEPSV SKAILAEAKK

LNDAQAPK VDAKFDKEAQ EAFYEILHLP NLTEEQRNAF IQSLKDEPSV

SKAILAEAKK LNDAQAPK VDAKFDKEAQ EAFYEILHLP NLTEEQRNAF

IQSLKDEPSV SKAILAEAKK LNDAQAPK VDAKFDKEAQ EAFYEILHLP

NLTEEQRNAF IQSLKDEPSV SKAILAEAKK LNDAQAPKC

Zvar (Q9A, N11E, D37E, Q40V, A42R, N43A, L44I)4
SEQ ID NO: 35

AQGT VDAKFDKEAQ EAFYEILHLP NLTEEQRNAF IQSLKDEPSV SRAILAEAKK

LNDAQAPK VDAKFDKEAQ EAFYEILHLP NLTEEQRNAF IQSLKDEPSV

SRAILAEAKK LNDAQAPK VDAKFDKEAQ EAFYEILHLP NLTEEQRNAF

IQSLKDEPSV SRAILAEAKK LNDAQAPK VDAKFDKEAQ EAFYEILHLP

NLTEEQRNAF IQSLKDEPSV SRAILAEAKK LNDAQAPKC

Zvar (Q9A, N11E, Q40V, A42K, N43A, L44I)2 with D2, A3 and K4 in linker deleted
SEQ ID NO: 80

VDAKFDKEAQ EAFYEILHLP NLTEEQRNAF IQSLKDDPSV SKAILAEAKK

LNDAQAPK VFDKEAQ EAFYEILHLP NLTEEQRNAF IQSLKDDPSV SKAILAEAKK

LNDAQAPKC

Zvar (Q9A, N11E, Q40V, A42K, N43A, L44I)2 with K58, V1 and D2 in linker deleted
SEQ ID NO: 81

VDAKFDKEAQ EAFYEILHLP NLTEEQRNAF IQSLKDDPSV SKAILAEAKK

LNDAQAP AKFDKEAQ EAFYEILHLP NLTEEQRNAF IQSLKDDPSV SKAILAEAKK

LNDAQAPKC

Zvar (Q9A, N11E, Q40V, A42K, N43A, L44I)2 with P57, K58, V1, D2 and A3 in linker deleted
SEQ ID NO: 82

VDAKFDKEAQ EAFYEILHLP NLTEEQRNAF IQSLKDDPSV SKAILAEAKK

LNDAQAP AKFDKEAQ EAFYEILHLP NLTEEQRNAF IQSLKDDPSV SKAILAEAKK

LNDAQAPKC

Zvar (Q9A, N11E, Q40V, A42K, N43A, L44I)2 with K4, F5, D6, K7 and E8 in linker deleted
SEQ ID NO: 83

VDAKFDKEAQ EAFYEILHLP NLTEEQRNAF IQSLKDDPSV SKAILAEAKK

LNDAQAPK VDAAQ EAFYEILHLP NLTEEQRNAF IQSLKDDPSV SKAILAEAKK

LNDAQAPKC

-continued

```
Zvar (Q9A, N11E, Q40V, A42K, N43A, L44I)2 with A56, P57 and K58 in linker deleted
                                                                      SEQ ID NO: 84
VDAKFDKEAQ EAFYEILHLP NLTEEQRNAF IQSLKDDPSV SKAILAEAKK LNDAQ

VDAKFDKEAQ EAFYEILHLP NLTEEQRNAF IQSLKDDPSV SKAILAEAKK

LNDAQAPKC

Zvar (Q9A, N11E, Q40V, A42K, N43A, L44I)2 with V1, D2 and A3 in linker deleted
                                                                      SEQ ID NO: 85
VDAKFDKEAQ EAFYEILHLP NLTEEQRNAF IQSLKDDPSV SKAILAEAKK

LNDAQAPK KFDKEAQ EAFYEILHLP NLTEEQRNAF IQSLKDDPSV SKAILAEAKK

LNDAQAPKC

Zvar (Q9A, N11E, Q40V, A42K, N43A, L44I)2 with V1, D2, A3, K4, F5, D6, K7 and E8
in linker deleted
                                                                      SEQ ID NO: 86
VDAKFDKEAQ EAFYEILHLP NLTEEQRNAF IQSLKDDPSV SKAILAEAKK

LNDAQAPK AQ EAFYEILHLP NLTEEQRNAF IQSLKDDPSV SKAILAEAKK

LNDAQAPKC

Zvar (Q9A, N11E, Q40V, A42K, N43A, L44I)
2 with YEDG inserted in linker between K58 and V1
                                                                      SEQ ID NO: 87
VDAKFDKEAQ EAFYEILHLP NLTEEQRNAF IQSLKDDPSV SKAILAEAKK

LNDAQAPK YEDG VDAKFDKEAQ EAFYEILHLP NLTEEQRNAF IQSLKDDPSV

SKAILAEAKK LNDAQAPKC

Zvar2
                                                                      SEQ ID NO: 88
VDAKFDKEAQ EAFYEILHLP NLTEEQRNAF IQSLKDDPSV SKAILAEAKK

LNDAQAPK VDAKFDKEAQ EAFYEILHLP NLTEEQRNAF IQSLKDDPSV

SKAILAEAKK LNDAQAPKC
```

In some embodiments, the polypeptide and/or multimer, as disclosed above, further comprises at the C-terminal or N-terminal end one or more coupling elements, selected from the group consisting of one or more cysteine residues, a plurality of lysine residues and a plurality of histidine residues. The coupling element(s) may also be located within 1-5 amino acid residues, such as within 1-3 or 1-2 amino acid residues from the C-terminal or N-terminal end. The coupling element may e.g. be a single cysteine at the C-terminal end. The coupling element(s) may be directly linked to the C- or N-terminal end, or it/they may be linked via a stretch comprising up to 15 amino acids, such as 1-5, 1-10 or 5-10 amino acids. This stretch should preferably also be sufficiently stable in alkaline environments not to impair the properties of the mutated protein. For this purpose, it is advantageous if the stretch does not contain asparagine. It can additionally be advantageous if the stretch does not contain glutamine. An advantage of having a C-terminal cysteine is that endpoint coupling of the protein can be achieved through reaction of the cysteine thiol with an electrophilic group on a support. This provides excellent mobility of the coupled protein which is important for the binding capacity.

The alkali stability of the polypeptide or multimer can be assessed by coupling it to an SPR chip, e.g. to Biacore CM5 sensor chips as described in the examples, using e.g. NHS- or maleimide coupling chemistries, and measuring the immunoglobulin-binding capacity of the chip, typically using polyclonal human IgG, before and after incubation in alkaline solutions at a specified temperature, e.g. 22+/−2° C. The incubation can e.g. be performed in 0.5 M NaOH for a number of 10 min cycles, such as 100, 200 or 300 cycles. The IgG capacity of the matrix after 100 10 min incubation cycles in 0.5 M NaOH at 22+/−2° C. can be at least 55, such as at least 60, at least 80 or at least 90% of the IgG capacity before the incubation. Alternatively, the remaining IgG capacity after 100 cycles for a particular mutant measured as above can be compared with the remaining IgG capacity for the parental polypeptide/multimer. In this case, the remaining IgG capacity for the mutant may be at least 105%, such as at least 110%, at least 125%, at least 150% or at least 200% of the parental polypeptide/multimer.

In a third aspect the present invention discloses a nucleic acid encoding a polypeptide or multimer according to any embodiment disclosed above. Thus, the invention encompasses all forms of the present nucleic acid sequence such as the RNA and the DNA encoding the polypeptide or multimer. The invention embraces a vector, such as a plasmid, which in addition to the coding sequence comprises the required signal sequences for expression of the polypeptide or multimer according the invention. In one embodiment, the vector comprises nucleic acid encoding a multimer according to the invention, wherein the separate nucleic acids encoding each unit may have homologous or heterologous DNA sequences.

In a fourth aspect the present invention discloses an expression system, which comprises, a nucleic acid or a vector as disclosed above. The expression system may e.g. be a gram-positive or gram-negative prokaryotic host cell system, e.g. *E. coli* or *Bacillus* sp. which has been modified to express the present polypeptide or multimer. In an alternative embodiment, the expression system is a eukaryotic host cell system, such as a yeast, e.g. *Pichia pastoris* or *Saccharomyces cerevisiae*, or mammalian cells, e.g. CHO cells.

In a fifth aspect, the present invention discloses a separation matrix, wherein a plurality of polypeptides or multimers according to any embodiment disclosed above have been coupled to a solid support. The separation matrix may comprise at least 11, such as 11-21, 15-21 or 15-18 mg/ml Fc-binding ligands covalently coupled to a porous support, wherein:
  a) the ligands comprise multimers of alkali-stabilized Protein A domains,
  b) the porous support comprises cross-linked polymer particles having a volume-weighted median diameter (d50,v) of 56-70, such as 56-66, micrometers and a dry solids weight of 55-80, such as 60-78 or 65-78, mg/ml. The cross-linked polymer particles may further have a pore size corresponding to an inverse gel filtration chromatography Kd value of 0.69-0.85, such as 0.70-0.85 or 0.69-0.80, for dextran of Mw 110 kDa. Suitably, the cross-linked polymer particles can have a high rigidity, to be able to withstand high flow rates. The rigidity can be measured with a pressure-flow test as further described in Example 8, where a column packed with the matrix is subjected to increasing flow rates of distilled water. The pressure is increased stepwise and the flow rate and back pressure measured, until the flow rate starts to decrease with increasing pressures. The maximum flow rate achieved and the maximum pressure (the back pressure corresponding to the maximum flow rate) are measured and used as measures of the rigidity.

When measured in a FINELINE 35 column (GE Healthcare Life Sciences) at a bed height of 300+/−10 mm, the max pressure can suitably be at least 0.58 MPa, such as at least 0.60 MPa. This allows for the use of smaller particle diameters, which is beneficial for the dynamic capacity.

The multimers may e.g. comprise tetramers, pentamers, hexamers or heptamers of alkali-stabilized Protein A domains, such as hexamers of alkali-stabilized Protein A domains. The combination of the high ligand contents with the particle size range, the dry solids weight range and the optional Kd range provides for a high binding capacity, e.g. such that the 10% breakthrough dynamic binding capacity for IgG is at least 45 mg/ml, such as at least 50 or at least 55 mg/ml at 2.4 min residence time. Alternatively, or additionally, the 10% breakthrough dynamic binding capacity for IgG may be at least 60 mg/ml, such as at least 65, at least 70 or at least 75 mg/ml at 6 min residence time.

The alkali-stabilized Protein A multimers are highly selective for IgG and the separation matrix can suitably have a dissociation constant for human IgG2 of below 0.2 mg/ml, such as below 0.1 mg/ml, in 20 mM phosphate buffer, 180 mM NaCl, pH 7.5. This can be determined according to the adsorption isotherm method described in N Pakiman et al: J Appl Sci 12, 1136-1141 (2012).

In certain embodiments the alkali-stabilized Protein A domains comprise mutants of a parental Fc-binding domain of *Staphylococcus* Protein A (SpA), as defined by, or having at least 80% such as at least 90%, 95% or 98% identity to, SEQ ID NO: 1, SEQ ID NO: 2, SEQ ID NO:3, SEQ ID NO: 4, SEQ ID NO: 5, SEQ ID NO:6, SEQ ID NO:7, SEQ ID NO:22, SEQ ID NO:51 or SEQ ID NO:52, wherein at least the asparagine or serine residue at the position corresponding to position 11 in SEQ ID NO:4-7 has been mutated to an amino acid selected from the group consisting of glutamic acid, lysine, tyrosine, threonine, phenylalanine, leucine, isoleucine, tryptophan, methionine, valine, alanine, histidine and arginine, such as an amino acid selected from the group consisting of glutamic acid and lysine. The amino acid residue at the position corresponding to position 40 in SEQ ID NO:4-7 may further be, or be mutated to, a valine. The alkali-stabilized Protein A domains may also comprise any mutations as described in the polypeptide and/or multimer embodiments above.

In some embodiments the alkali-stabilized Protein A domains comprise an Fc-binding polypeptide having an amino acid sequence as defined by, or having at least 80% or at least 90, 95% or 98% identity to SEQ ID NO:53.

$X_1Q$ $X_2$AFYEIL$X_3$LP NLTEEQR$X_4X_5$F I$X_6X_7$LKD$X_8$PS$X_9$ S$X_{10}X_{11}X_{12}$LAEAK$X_{13}X_{14}$N$X_{15}$AQ (SEQ ID NO:53)

wherein individually of each other:
  $X_1$=A or Q or is deleted
  $X_2$=E, K, Y, T, F, L, W, I, M, V, A, H or R
  $X_3$=H or K
  $X_4$=A or N
  $X_5$=A, G, S, Y, Q, T, N, F, L, W, I, M, V, D, E, H, R or K
  $X_6$=Q or E
  $X_7$=S or K
  $X_8$=E or D
  $X_9$=Q or V or is deleted
  $X_{10}$=K, R or A or is deleted
  $X_{11}$=A, E or N or is deleted
  $X_{12}$=I or L
  $X_{13}$=K or R
  $X_{14}$=L or Y
  $X_{15}$=D, F, Y, W, K or R In some embodiments, the amino acid residues may individually of each other be:
  a) $X_1$=A or is deleted, $X_2$=E, $X_3$=H, $X_4$=N, $X_6$=Q, $X_7$=S, $X_8$=D, $X_9$=V or is deleted, $X_{10}$=K or is deleted, $X_{11}$=A or is deleted, $X_{12}$=I, $X_{13}$=K, $X_{14}$=L.
  b) $X_1$=A, $X_2$=E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.
  c) $X_1$ is A, $X_2$=E, $X_3$=H, $X_4$=N, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D or
  d) $X_1$ is A, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

In certain embodiments the invention discloses a separation matrix comprising at least 15, such as 15-21 or 15-18 mg/ml Fc-binding ligands covalently coupled to a porous support, wherein the ligands comprise multimers of alkali-stabilized Protein A domains. These multimers can suitably be as disclosed in any of the embodiments described above or as specified below.

Such a matrix is useful for separation of immunoglobulins or other Fc-containing proteins and, due to the improved alkali stability of the polypeptides/multimers, the matrix will withstand highly alkaline conditions during cleaning, which is essential for long-term repeated use in a bioprocess separation setting. The alkali stability of the matrix can be assessed by measuring the immunoglobulin-binding capacity, typically using polyclonal human IgG, before and after incubation in alkaline solutions at a specified temperature, e.g. 22+/−2° C. The incubation can e.g. be performed in 0.5 M or 1.0 M NaOH for a number of 15 min cycles, such as 100, 200 or 300 cycles, corresponding to a total incubation time of 25, 50 or 75 h. The IgG capacity of the matrix after 96-100 15 min incubation cycles or a total incubation time of 24 or 25 h in 0.5 M NaOH at 22+/−2° C. can be at least 80, such as at least 85, at least 90 or at least 95% of the IgG capacity before the incubation. The capacity of the matrix after a total incubation time of 24 h in 1.0 M NaOH at 22+/−2° C. can be at least 70, such as at least 80 or at least 90% of the IgG capacity before the incubation. The 10% breakthrough dynamic binding capacity (Qb10%) for IgG at 2.4 min or 6 min residence time may e.g. be reduced by less than 20% after incubation 31 h in 1.0 M aqueous NaOH at 22+/−2 C.

As the skilled person will understand, the expressed polypeptide or multimer should be purified to an appropriate extent before being immobilized to a support. Such purification methods are well known in the field, and the immobilization of protein-based ligands to supports is easily carried out using standard methods. Suitable methods and supports will be discussed below in more detail.

The solid support of the matrix according to the invention can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—CONH$_2$, possibly in N-substituted forms), amiNO: (—NH$_2$, possibly in substituted form), oligo- or polyethylenoxy groups on their external and, if present, also on internal surfaces. The solid support can suitably be porous. The porosity can be expressed as a Kav or Kd value (the fraction of the pore volume available to a probe molecule of a particular size) measured by inverse size exclusion chromatography, e.g. according to the methods described in Gel Filtration Principles and Methods, Pharmacia LKB Biotechnology 1991, pp 6-13. Kav is determined as the ratio $(V_e-V_o)/(V_t-V_o)$, where $V_e$ is the elution volume of a probe molecule (e.g. Dextran 110 kD), $V_o$ is the void volume of the column (e.g. the elution volume of a high Mw void marker, such as raw dextran) and $V_t$ is the total volume of the column. Kd can be determined as $(V_e-V_o)/V_i$, where $V_i$ is the elution volume of a salt (e.g. NaCl) able to access all the volume except the matrix volume (the volume occupied by the matrix polymer molecules). By definition, both Kd and Kav values always lie within the range 0-1. The Kav value can advantageously be 0.6-0.95, e.g. 0.7-0.90 or 0.6-0.8, as measured with dextran of Mw 110 kDa as a probe molecule. The Kd value as measured with dextran of Mw 110 kDa can suitably be 0.68-0.90, such as 0.68-0.85 or 0.70-0.85. An advantage of this is that the support has a large fraction of pores able to accommodate both the polypeptides/multimers of the invention and immunoglobulins binding to the polypeptides/multimers and to provide mass transport of the immunoglobulins to and from the binding sites.

The polypeptides or multimers may be attached to the support via conventional coupling techniques utilising e.g. thiol, amiNO: and/or carboxy groups present in the ligand. Bisepoxides, epichlorohydrin, CNBr, N-hydroxysuccinimide (NHS) etc are well-known coupling reagents. Between the support and the polypeptide/multimer, a molecule known as a spacer can be introduced, which improves the availability of the polypeptide/multimer and facilitates the chemical coupling of the polypeptide/multimer to the support. Depending on the nature of the polypeptide/multimer and the coupling conditions, the coupling may be a multipoint coupling (e.g. via a plurality of lysines) or a single point coupling (e.g. via a single cysteine). Alternatively, the polypeptide/multimer may be attached to the support by non-covalent bonding, such as physical adsorption or biospecific adsorption.

In some embodiments the matrix comprises 5-25, such as 5-20 mg/ml, 5-15 mg/ml, 5-11 mg/ml or 6-11 mg/ml of the polypeptide or multimer coupled to the support. The amount of coupled polypeptide/multimer can be controlled by the concentration of polypeptide/multimer used in the coupling process, by the activation and coupling conditions used and/or by the pore structure of the support used. As a general rule the absolute binding capacity of the matrix increases with the amount of coupled polypeptide/multimer, at least up to a point where the pores become significantly constricted by the coupled polypeptide/multimer. Without being bound by theory, it appears though that for the Kd values recited for the support, the constriction of the pores by coupled ligand is of lower significance. The relative binding capacity per mg coupled polypeptide/multimer will decrease at high coupling levels, resulting in a cost-benefit optimum within the ranges specified above.

In certain embodiments the polypeptides or multimers are coupled to the support via thioether bonds. Methods for performing such coupling are well-known in this field and easily performed by the skilled person in this field using standard techniques and equipment. Thioether bonds are flexible and stable and generally suited for use in affinity chromatography. In particular when the thioether bond is via a terminal or near-terminal cysteine residue on the polypeptide or multimer, the mobility of the coupled polypeptide/multimer is enhanced which provides improved binding capacity and binding kinetics. In some embodiments the polypeptide/multimer is coupled via a C-terminal cysteine provided on the protein as described above. This allows for efficient coupling of the cysteine thiol to electrophilic groups, e.g. epoxide groups, halohydrin groups etc. on a support, resulting in a thioether bridge coupling.

In certain embodiments the support comprises a polyhydroxy polymer, such as a polysaccharide. Examples of polysaccharides include e.g. dextran, starch, cellulose, pullulan, agar, agarose etc. Polysaccharides are inherently hydrophilic with low degrees of nonspecific interactions, they provide a high content of reactive (activatable) hydroxyl groups and they are generally stable towards alkaline cleaning solutions used in bioprocessing.

In some embodiments the support comprises agar or agarose. The supports used in the present invention can easily be prepared according to standard methods, such as inverse suspension gelation (S Hjertén: Biochim Biophys Acta 79(2), 393-398 (1964). Alternatively, the base matrices are commercially available products, such as crosslinked agarose beads sold under the name of SEPHAROSE™ FF (GE Healthcare). In an embodiment, which is especially advantageous for large-scale separations, the support has been adapted to increase its rigidity using the methods described in U.S. Pat. No. 6,602,990 or U.S. Pat. No. 7,396,467, which are hereby incorporated by reference in their entireties, and hence renders the matrix more suitable for high flow rates.

In certain embodiments the support, such as a polymer, polysaccharide or agarose support, is crosslinked, such as with hydroxyalkyl ether crosslinks. Crosslinker reagents producing such crosslinks can be e.g. epihalohydrins like epichlorohydrin, diepoxides like butanediol diglycidyl ether, allylating reagents like allyl halides or allyl glycidyl ether. Crosslinking is beneficial for the rigidity of the support and improves the chemical stability. Hydroxyalkyl ether crosslinks are alkali stable and do not cause significant nonspecific adsorption.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare) is used. In another alternative, the solid support according to the invention comprises a support of inorganic nature, e.g. silica, zirconium oxide etc.

In yet another embodiment, the solid support is in another form such as a surface, a chip, capillaries, or a filter (e.g. a membrane or a depth filter matrix).

As regards the shape of the matrix according to the invention, in one embodiment the matrix is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used.

In a sixth aspect, the present invention discloses a method of isolating an immunoglobulin, wherein a separation matrix as disclosed above is used. The method may comprise the steps of:
a) contacting a liquid sample comprising an immunoglobulin with a separation matrix as disclosed above,
b) washing the separation matrix with a washing liquid,
c) eluting the immunoglobulin from the separation matrix with an elution liquid, and
d) cleaning the separation matrix with a cleaning liquid, which may comprise 0.1-1.0 M NaOH or KOH, such as 0.4-1.0 M NaOH or KOH.

Steps a)-d) may be repeated at least 10 times, such as at least 50 times or 50-200 times.

In certain embodiments, the method comprises the steps of:
a) contacting a liquid sample comprising an immunoglobulin with a separation matrix as disclosed above,
b) washing said separation matrix with a washing liquid,
c) eluting the immunoglobulin from the separation matrix with an elution liquid, and
d) cleaning the separation matrix with a cleaning liquid, which can alternatively be called a cleaning-in-place (CIP) liquid, e.g. with a contact (incubation) time of at least 10 min.

The method may also comprise steps of, before step a), providing an affinity separation matrix according to any of the embodiments described above and providing a solution comprising an immunoglobulin and at least one other substance as a liquid sample and of, after step c), recovering the eluate and optionally subjecting the eluate to further separation steps, e.g. by anion or cation exchange chromatography, multimodal chromatography and/or hydrophobic interaction chromatography. Suitable compositions of the liquid sample, the washing liquid and the elution liquid, as well as the general conditions for performing the separation are well known in the art of affinity chromatography and in particular in the art of Protein A chromatography.

The liquid sample comprising an Fc-containing protein and at least one other substance may comprise host cell proteins (HCP), such as CHO cell, *E Coli* or yeast proteins. Contents of CHO cell and *E Coli* proteins can conveniently be determined by immunoassays directed towards these proteins, e.g. the CHO HCP or *E Coli* HCP ELISA kits from *Cygnus* Technologies. The host cell proteins or CHO cell/*E Coli* proteins may be desorbed during step b).

The elution may be performed by using any suitable solution used for elution from Protein A media. This can e.g. be a solution or buffer with pH 5 or lower, such as pH 2.5-5 or 3-5. It can also in some cases be a solution or buffer with pH 11 or higher, such as pH 11-14 or pH 11-13. In some embodiments the elution buffer or the elution buffer gradient comprises at least one mono- di- or trifunctional carboxylic acid or salt of such a carboxylic acid. In certain embodiments the elution buffer or the elution buffer gradient comprises at least one anion species selected from the group consisting of acetate, citrate, glycine, succinate, phosphate, and formiate.

In some embodiments, the cleaning liquid is alkaline, such as with a pH of 13-14. Such solutions provide efficient cleaning of the matrix, in particular at the upper end of the interval In certain embodiments, the cleaning liquid comprises 0.1-2.0 M NaOH or KOH, such as 0.5-2.0 or 0.5-1.0 M NaOH or KOH. These are efficient cleaning solutions, and in particular so when the NaOH or KOH concentration is above 0.1 M or at least 0.5 M. The high stability of the polypeptides of the invention enables the use of such strongly alkaline solutions.

The method may also include a step of sanitizing the matrix with a sanitization liquid, which may e.g. comprise a peroxide, such as hydrogen peroxide and/or a peracid, such as peracetic acid or performic acid.

In some embodiments, steps a)-d) are repeated at least 10 times, such as at least 50 times, 50-200, 50-300 or 50-500 times. This is important for the process economy in that the matrix can be re-used many times.

Steps a)-c) can also be repeated at least 10 times, such as at least 50 times, 50-200, 50-300 or 50-500 times, with step d) being performed after a plurality of instances of step c), such that step d) is performed at least 10 times, such as at least 50 times. Step d) can e.g. be performed every second to twentieth instance of step c).

EXAMPLES

Mutagenesis of Protein

Site-directed mutagenesis was performed by a two-step PCR using oligonucleotides coding for the mutations. As template a plasmid containing a single domain of either Z, B or C was used. The PCR fragments were ligated into an *E. coli* expression vector. DNA sequencing was used to verify the correct sequence of inserted fragments. To form multimers of mutants an Acc I site located in the starting codons (GTA GAC) of the B, C or Z domain was used, corresponding to amino acids VD. The vector for the monomeric domain was digested with Acc I and phosphatase treated. Acc I sticky-ends primers were designed, specific for each variant, and two overlapping PCR products were generated from each template. The PCR products were purified and the concentration was estimated by comparing the PCR products on a 2% agarose gel. Equal amounts of the pair wise PCR products were hybridized (90° C.→25° C. in 45 min) in ligation buffer. The resulting product consists approximately to ¼ of fragments likely to be ligated into an Acc I site (correct PCR fragments and/or the digested vector). After ligation and transformation colonies were PCR screened to identify constructs containing the desired mutant. Positive clones were verified by DNA sequencing.

Construct Expression and Purification

The constructs were expressed in the bacterial periplasm by fermentation of *E. coli* K12 in standard media. After fermentation the cells were heat-treated to release the periplasm content into the media. The constructs released into the medium were recovered by microfiltration with a membrane having a 0.2 μm pore size.

Each construct, now in the permeate from the filtration step, was purified by affinity. The permeate was loaded onto a chromatography medium containing immobilized IgG (IgG Sepharose 6FF, GE Healthcare). The loaded product was washed with phosphate buffered saline and eluted by lowering the pH.

The elution pool was adjusted to a neutral pH (pH 8) and reduced by addition of dithiothreitol. The sample was then loaded onto an anion exchanger. After a wash step the construct was eluted in a NaCl gradient to separate it from any contaminants. The elution pool was concentrated by ultrafiltration to 40-50 mg/ml. It should be noted that the successful affinity purification of a construct on an immobilized IgG medium indicates that the construct in question has a high affinity to IgG.

The purified ligands were analyzed with RPC LC-MS to determine the purity and to ascertain that the molecular weight corresponded to the expected (based on the amino acid sequence).

Example 1

The purified monomeric ligands listed in Table 1, further comprising for SEQ ID NO:8-16, 23-28 and 36-48 an AQGT leader sequence at the N-terminus and a cysteine at the C terminus, were immobilized on Biacore CM5 sensor chips (GE Healthcare, Sweden), using the amine coupling kit of GE Healthcare (for carbodiimide coupling of amines on the carboxymethyl groups on the chip) in an amount sufficient to give a signal strength of about 200-1500 RU in a Biacore surface plasmon resonance (SPR) instrument (GE Healthcare, Sweden). To follow the IgG binding capacity of the immobilized surface 1 mg/ml human polyclonal IgG (Gammanorm) was flowed over the chip and the signal strength (proportional to the amount of binding) was noted. The surface was then cleaned-in-place (CIP), i.e. flushed with 500 mM NaOH for 10 minutes at room temperature (22+/−2° C.). This was repeated for 96-100 cycles and the immobilized ligand alkaline stability was followed as the remaining IgG binding capacity (signal strength) after each cycle. The results are shown in Table 1 and indicate that at least the ligands Zvar(N11K)1, Zvar(N11E)1, Zvar(N11Y)1, Zvar(N11T)1, Zvar(N11F)1, Zvar(N11L)1, Zvar(N11W)1, ZN11I)1, Zvar(N11M)1, Zvar(N11V)1, Zvar(N11A)1, Zvar(N11H1), Zvar(N11R)1, Zvar(N11E,Q32A)1, Zvar(N11E,Q32E,Q40E)1 and Zvar(N11E,Q32E,K50R)1, Zvar(Q9A,N11E,N43A)1, Zvar(Q9A,N11E,N28A,N43A)1, Zvar(Q9A,N11E,Q40V,A42K,N43A,L44I)1, Zvar(Q9A,N11E,Q40V,A42K,N43A,L44I)1, Zvar(Q9A,N11E,N28A,Q40V,A42K,N43A,L44I)1, Zvar(N11K,H18K,S33K,D37E,A42R,N43A,L44I,K50R,L51Y)1, Zvar(Q9A,N11K,H18K,S33K,D37E,A42R,N43A,L44I,K50R,L51Y)1, Zvar(N11K,H18K,D37E,A42R,N43A,L44I)1, Zvar(Q9A,N11K,H18K,D37E,A42R,N43A,L44I)1 and Zvar(Q9A,N11K,H18K,D37E,A42R,N43A,L44I,K50R)1, as well as the varieties of Zvar(Q9A,N11E,Q40V,A42K,N43A,L44I)1 having G, S, Y, Q, T, N, F, L, W, I, M, V, D, E, H, R or K in position 29, the varieties of Zvar(Q9A,N11E,Q40V,A42K,N43A,L44I)1 having F, Y, W, K or R in position 53 and the varieties of Zvar(Q9A,N11E,Q40V,A42K,N43A,L44I)1 where Q9, Q40, A42 or N43 has been deleted, have an improved alkali stability compared to the parental structure Zvar1, used as the reference. Further, the ligands B(Q9A,N11E,Q40V,A42K,N43A,L44I)1 and C(Q9A,N11E,E43A)1 have an improved stability compared to the parental B and C domains, used as references.

TABLE 1

Monomeric ligands, evaluated by Biacore (0.5M NaOH).

| Ligand | Sequence | Capacity after 96-100 cycles | Reference capacity after 96-100 cycles | Capacity relative to reference |
|---|---|---|---|---|
| Zvar(N11E, Q32A)1 | SEQ ID NO: 12 | 57% | 55% | 1.036 |
| Zvar(N11E)1 | SEQ ID NO: 13 | 59% | 55% | 1.073 |
| Zvar(N11E, Q32E, Q40E)1 | SEQ ID NO: 14 | 52% | 51% | 1.020 |
| Zvar(N11E, Q32E, K50R)1 | SEQ ID NO: 15 | 53% | 51% | 1.039 |
| Zvar(N11K)1 | SEQ ID NO: 16 | 62% | 49% | 1.270 |
| Zvar(N11Y)1 | SEQ ID NO: 38 | 55% | 46% | 1.20 |
| Zvar(N11T)1 | SEQ ID NO: 39 | 50% | 46% | 1.09 |
| Zvar(N11F)1 | SEQ ID NO: 40 | 55% | 46% | 1.20 |
| Zvar(N11L)1 | SEQ ID NO: 41 | 57% | 47% | 1.21 |
| Zvar(N11W)1 | SEQ ID NO: 42 | 57% | 47% | 1.21 |

TABLE 1-continued

Monomeric ligands, evaluated by Biacore (0.5M NaOH).

| Ligand | Sequence | Capacity after 96-100 cycles | Reference capacity after 96-100 cycles | Capacity relative to reference |
|---|---|---|---|---|
| Zvar(N11I)1 | SEQ ID NO: 43 | 57% | 47% | 1.21 |
| Zvar(N11M)1 | SEQ ID NO: 44 | 58% | 46% | 1.26 |
| Zvar(N11V)1 | SEQ ID NO: 45 | 56% | 46% | 1.22 |
| Zvar(N11A)1 | SEQ ID NO: 46 | 58% | 46% | 1.26 |
| Zvar(N11H)1 | SEQ ID NO: 47 | 57% | 46% | 1.24 |
| Zvar(N11R)1 | SEQ ID NO: 48 | 59% | 46% | 1.28 |
| Zvar(Q9A, N11E, N43A)1 | SEQ ID NO: 8 | 70% | 47% | 1.49 |
| Zvar(Q9A, N11E, N28A, N43A)1 | SEQ ID NO: 9 | 68% | 47% | 1.45 |
| Zvar(Q9A, N11E, Q40V, A42K, N43E, L44I)1 | SEQ ID NO: 10 | 67% | 47% | 1.43 |
| Zvar(Q9A, N11E, Q40V, A42K, N43A, L44I)1 | SEQ ID NO: 11 | 66% | 47% | 1.40 |
| Zvar(Q9A, N11E, N28A, Q40V, A42K, N43A, L44I)1 | SEQ ID NO: 24 | 65% | 48% | 1.35 |
| Zvar(N11K, H18K, S33K, D37E, A42R, N43A, L44I, K50R, L51Y)1 | SEQ ID NO: 23 | 67% | 46% | 1.46 |
| Zvar(Q9A, N11K, H18K, S33K, D37E, A42R, N43A, L44I, K50R, L51Y)1 | SEQ ID NO: 25 | 59% | 46% | 1.28 |
| Zvar(N11K, H18K, D37E, A42R, N43A, L44I)1 | SEQ ID NO: 26 | 59% | 45% | 1.31 |
| Zvar(Q9A, N11K, H18K, D37E, A42R, N43A, L44I)1 | SEQ ID NO: 27 | 63% | 45% | 1.40 |
| Zvar(Q9A, N11K, H18K, D37E, A42R, N43A, L44I, K50R)1 | SEQ ID NO: 28 | 67% | 45% | 1.49 |
| B(Q9A, N11E, Q40V, A42K, N43A, L44I)1 | SEQ ID NO: 36 | 39% | 35% | 1.11 |
| C(Q9A, N11E, E43A)1 | SEQ ID NO: 37 | 60% | 49% | 1.22 |
| Zvar(Q9A, N11E, A29G, Q40V, A42K, N43A, L44I)1 | SEQ ID NO: 54 | 69% | 48% | 1.44 |
| Zvar(Q9A, N11E, A29S, Q40V, A42K, N43A, L44I)1 | SEQ ID NO: 55 | 66% | 48% | 1.38 |
| Zvar(Q9A, N11E, A29Y, Q40V, A42K, N43A, L44I)1 | SEQ ID NO: 56 | 61% | 48% | 1.27 |
| Zvar(Q9A, N11E, A29Q, Q40V, A42K, N43A, L44I)1 | SEQ ID NO: 57 | 60% | 47% | 1.28 |
| Zvar(Q9A, N11E, A29T, Q40V, A42K, N43A, L44I)1 | SEQ ID NO: 58 | 60% | 47% | 1.28 |
| Zvar(Q9A, N11E, A29N, Q40V, A42K, N43A, L44I)1 | SEQ ID NO: 59 | 61% | 47% | 1.30 |
| Zvar(Q9A, N11E, A29F, Q40V, A42K, N43A, L44I)1 | SEQ ID NO: 60 | 62% | 46% | 1.35 |
| Zvar(Q9A, N11E, A29L, Q40V, A42K, N43A, L44I)1 | SEQ ID NO: 61 | 61% | 46% | 1.33 |
| Zvar(Q9A, N11E, A29W, Q40V, A42K, N43A, L44I)1 | SEQ ID NO: 62 | 60% | 46% | 1.30 |
| Zvar(Q9A, N11E, A29I, Q40V, A42K, N43A, L44I)1 | SEQ ID NO: 63 | 58% | 47% | 1.23 |
| Zvar(Q9A, N11E, A29M, Q40V, A42K, N43A, L44I)1 | SEQ ID NO: 64 | 62% | 47% | 1.32 |
| Zvar(Q9A, N11E, A29V, Q40V, A42K, N43A, L44I)1 | SEQ ID NO: 65 | 62% | 47% | 1.32 |
| Zvar(Q9A, N11E, A29D, Q40V, A42K, N43A, L44I)1 | SEQ ID NO: 66 | 56% | 47% | 1.19 |
| Zvar(Q9A, N11E, A29E, Q40V, A42K, N43A, L44I)1 | SEQ ID NO: 67 | 57% | 47% | 1.21 |
| Zvar(Q9A, N11E, A29H, Q40V, A42K, N43A, L44I)1 | SEQ ID NO: 68 | 57% | 47% | 1.21 |
| Zvar(Q9A, N11E, A29R, Q40V, A42K, N43A, L44I)1 | SEQ ID NO: 69 | 58% | 46% | 1.26 |
| Zvar(Q9A, N11E, A29K, Q40V, A42K, N43A, L44I)1 | SEQ ID NO: 70 | 59% | 46% | 1.28 |
| Zvar(Q9A, N11E, Q40V, A42K, N43A, L44I, D53F)1 | SEQ ID NO: 71 | 58% | 46% | 1.26 |

TABLE 1-continued

Monomeric ligands, evaluated by Biacore (0.5M NaOH).

| Ligand | Sequence | Capacity after 96-100 cycles | Reference capacity after 96-100 cycles | Capacity relative to reference |
|---|---|---|---|---|
| Zvar(Q9A, N11E, Q40V, A42K, N43A, L44I, D53Y)1 | SEQ ID NO: 72 | 59% | 46% | 1.28 |
| Zvar(Q9A, N11E, Q40V, A42K, N43A, L44I, D53W)1 | SEQ ID NO: 73 | 62% | 46% | 1.35 |
| Zvar(Q9A, N11E, Q40V, A42K, N43A, L44I, D53K)1 | SEQ ID NO: 74 | 65% | 46% | 1.41 |
| Zvar(Q9A, N11E, Q40V, A42K, N43A, L44I, D53R)1 | SEQ ID NO: 75 | 60% | 46% | 1.30 |
| Zvar(Q9del, N11E, Q40V, A42K, N43A, L44I)1 | SEQ ID NO: 76 | 60% | 46% | 1.30 |
| Zvar(Q9A, N11E, Q40del, A42K, N43A, L44I)1 | SEQ ID NO: 77 | 59% | 46% | 1.28 |
| Zvar(Q9A, N11E, Q40V, A42del, N43A, L44I)1 | SEQ ID NO: 78 | 57% | 46% | 1.24 |
| Zvar(Q9A, N11E, Q40V, A42K, N43del, L44I)1 | SEQ ID NO: 79 | 55% | 46% | 1.20 |

The Biacore experiment can also be used to determine the binding and dissociation rates between the ligand and IgG. This was used with the set-up as described above and with an IgG1 monoclonal antibody as probe molecule. For the reference Zvar1, the on-rate ($10^5$ $M^{-1}s^{-1}$) was 3.1 and the off-rate ($10^5$ $s^{-1}$) was 22.1, giving an affinity (off-rate/on-rate) of 713 pM. For Zvar(Q9A,N11E,Q40V,A42K,N43A, L44I)1 (SEQ ID NO:11), the on-rate was 4.1 and the off-rate 43.7, with affinity 1070 pM. The IgG affinity was thus somewhat higher for the mutated variant.

Example 2

The purified dimeric, tetrameric and hexameric ligands listed in Table 2 were immobilized on Biacore CM5 sensor chips (GE Healthcare, Sweden), using the amine coupling kit of GE Healthcare (for carbodiimide coupling of amines on the carboxymethyl groups on the chip) in an amount sufficient to give a signal strength of about 200-1500 RU in a Biacore instrument (GE Healthcare, Sweden). To follow the IgG binding capacity of the immobilized surface 1 mg/ml human polyclonal IgG (Gammanorm) was flowed over the chip and the signal strength (proportional to the amount of binding) was noted. The surface was then cleaned-in-place (CIP), i.e. flushed with 500 mM NaOH for 10 minutes at room temperature (22+/−2° C.). This was repeated for 300 cycles and the immobilized ligand alkaline stability was followed as the remaining IgG binding capacity (signal strength) after each cycle. The results are shown in Table 2 and in FIG. 2 and indicate that at least the ligands Zvar(Q9A,N11E,N43A)4, Zvar(Q9A,N11E,N28A,N43A)4, Zvar(Q9A,N11E,Q40V,A42K,N43E,L44I)4 and Zvar(Q9A, N11E,Q40V,A42K,N43A,L44I)4, Zvar(Q9A,N11E,D37E, Q40V,A42K,N43A,L44I)4 and Zvar(Q9A,N11E,D37E, Q40V,A42R,N43A,L44I)4 have an improved alkali stability compared to the parental structure Zvar4, which was used as a reference. The hexameric ligand Zvar(Q9A,N11E,Q40V, A42K,N43A,L44I)6 also has improved alkali stability compared to the parental structure Zvar6, used as a reference. Further, Zvar(Q9A,N11E,Q40V,A42K,N43A,L44I) dimers with deletions of a) D2,A3,K4; b) K58,V1,D2; c) P57,K58, V1,D2,A3; d) K4,F5,D6,K7,E8; e) A56,P57,K58; V1,D2, A3 or f) V1,D2,A3,K4,F5,D6,K7,E8 from the linker region between the two monomer units have improved alkali stability compared to the parental structure Zvar2, used as a reference. Also Zvar(Q9A,N11E,Q40V,A42K,N43A,L44I) dimers with an insertion of YEDG between K58 and V1 in the linker region have improved alkali stability compared to Zvar2.

TABLE 2

Dimeric, tetrameric and hexameric ligands, evaluated by Biacore (0.5M NaOH).

| Ligand | SEQ ID NO: | Remaining capacity 100 cycles (%) | Capacity relative to ref. 100 cycles | Remaining capacity 200 cycles (%) | Capacity relative to ref. 200 cycles | Remaining capacity 300 cycles (%) | Capacity relative to ref. 300 cycles |
|---|---|---|---|---|---|---|---|
| Zvar4 | 21 | 67 | 1 | 36 | 1 | 16 | 1 |
| Zvar(Q9A, N11E, N43A)4 | 17 | 81 | 1.21 | 62 | 1.72 | 41 | 2.56 |
| Zvar(Q9A, N11E, N28A, N43A)4 | 18 | 80 | 1.19 | 62 | 1.72 | 42 | 2.62 |
| Zvar(Q9A, N11E, Q40V, A42K, N43E, L44I)4 | 19 | 84 | 1.25 | 65 | 1.81 | 48 | 3.00 |
| Zvar(Q9A, N11E, Q40V, A42K, N43A, L44I)4 | 20 | 90 | 1.34 | 74 | 2.06 | 57 | 3.56 |

TABLE 2-continued

Dimeric, tetrameric and hexameric ligands, evaluated by Biacore (0.5M NaOH).

| Ligand | SEQ ID NO: | Remaining capacity 100 cycles (%) | Capacity relative to ref. 100 cycles | Remaining capacity 200 cycles (%) | Capacity relative to ref. 200 cycles | Remaining capacity 300 cycles (%) | Capacity relative to ref. 300 cycles |
|---|---|---|---|---|---|---|---|
| Zvar(Q9A, N11E, N28A, Q40V, A42K, N43A, L44I)4 | 32 | 84 | 1.24 | Not tested | Not tested | Not tested | Not tested |
| Zvar(Q9A, N11E, Q40V, A42K, N43A, L44I)6 | 33 | 87 | 1.30 | Not tested | Not tested | Not tested | Not tested |
| Zvar(Q9A, N11E, D37E, Q40V, A42K, N43A, L44I)4 | 34 | 81 | 1.13 | Not tested | Not tested | Not tested | Not tested |
| Zvar(Q9A, N11E, D37E, Q40V, A42R, N43A, L44I)4 | 35 | 84 | 1.17 | Not tested | Not tested | Not tested | Not tested |
| Zvar(Q9A, N11E, Q40V, A42K, N43A, L44I)2 with D2, A3 and K4 in linker deleted | 80 | 70 | 1.27 | Not tested | Not tested | Not tested | Not tested |
| Zvar(Q9A, N11E, Q40V, A42K, N43A, L44I)2 with K58, V1 and D2 in linker deleted | 81 | 76 | 1.38 | Not tested | Not tested | Not tested | Not tested |
| Zvar(Q9A, N11E, Q40V, A42K, N43A, L44I)2 with P57, K58, V1, D2 and A3 in linker deleted | 82 | 74 | 1.35 | Not tested | Not tested | Not tested | Not tested |
| Zvar(Q9A, N11E, Q40V, A42K, N43A, L44I)2 with K4, F5, D6, K7 and E8 in linker deleted | 83 | 70 | 1.30 | Not tested | Not tested | Not tested | Not tested |
| Zvar(Q9A, N11E, Q40V, A42K, N43A, L44I)2 with A56, P57 and K58 in linker deleted | 84 | 68 | 1.26 | Not tested | Not tested | Not tested | Not tested |
| Zvar(Q9A, N11E, Q40V, A42K, N43A, L44I)2 with V1, D2 and A3 in linker deleted | 85 | 75 | 1.39 | Not tested | Not tested | Not tested | Not tested |
| Zvar(Q9A, N11E, Q40V, A42K, N43A, L44I)2 with V1, D2, A3, K4, F5, D6, K7 and E8 in linker deleted | 86 | 62 | 1.13 | Not tested | Not tested | Not tested | Not tested |
| Zvar(Q9A, N11E, Q40V, A42K, N43A, L44I)2 with YEDG inserted in linker between K58 and V1 | 87 | 72 | 1.31 | Not tested | Not tested | Not tested | Not tested |
| Zvar2 | 88 | 55 | 1 | Not tested | Not tested | Not tested | Not tested |

Example 3

Example 2 was repeated with 100 CIP cycles of three ligands using 1 M NaOH instead of 500 mM as in Example 2. The results are shown in Table 3 and show that all three ligands have an improved alkali stability also in 1M NaOH, compared to the parental structure Zvar4 which was used as a reference.

TABLE 3

Tetrameric ligands, evaluated by Biacore (1M NaOH).

| Ligand | Sequence | Remaining capacity 100 cycles (%) | Capacity relative to ref. 100 cycles |
|---|---|---|---|
| Zvar4 | SEQ ID NO: 21 | 27 | 1 |
| Zvar(Q9A, N11E, N28A, N43A)4 | SEQ ID NO: 18 | 55 | 2.04 |
| Zvar(Q9A, N11E, Q40V, A42K, N43E, L44I)4 | SEQ ID NO: 19 | 54 | 2.00 |
| Zvar(Q9A, N11E, Q40V, A42K, N43A, L44I)4 | SEQ ID NO: 20 | 56 | 2.07 |

Example 4

Figure 3:
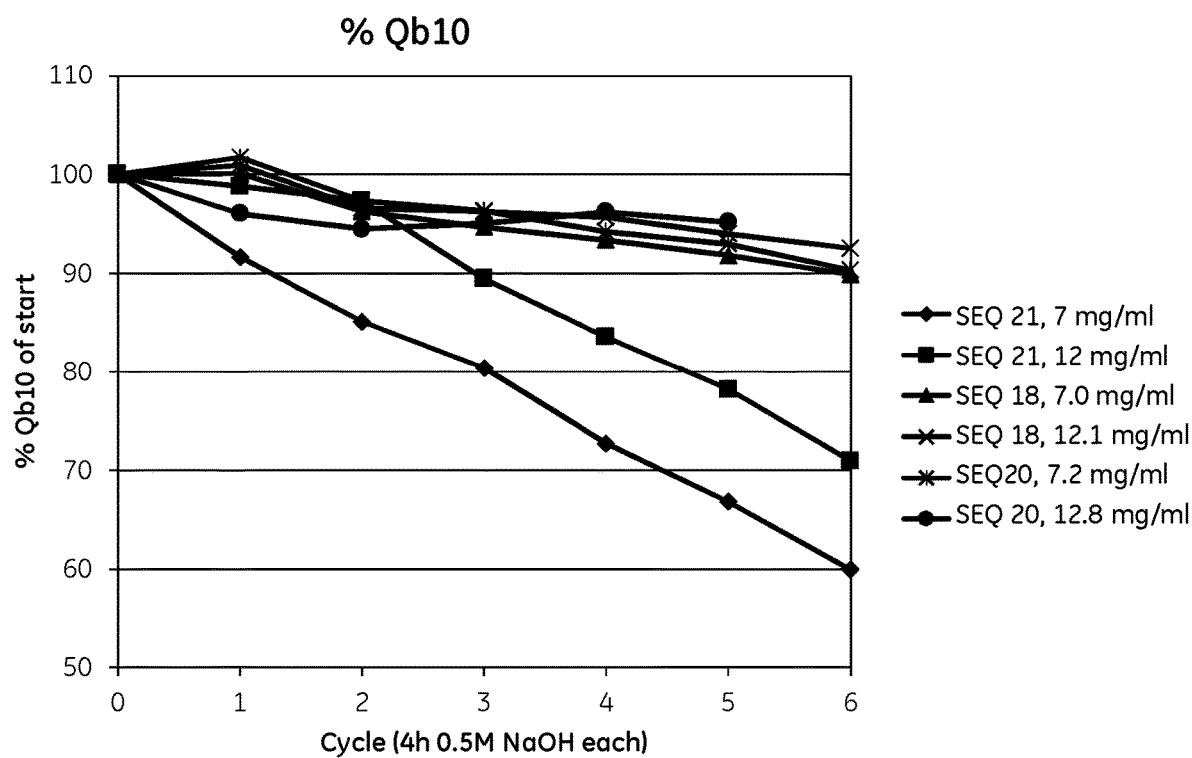
FIG. 3 shows results from Example 4 for the alkali stability (0.5 M NaOH) of parental and mutated tetrameric Zvar (SEQ ID NO:7) polypeptide variants coupled to agarose beads.

The purified tetrameric ligands of Table 2 (all with an additional N-terminal cysteine) were immobilized on agarose beads using the methods described below and assessed for capacity and stability. The results are shown in Table 4 and FIG. 3.

TABLE 4

Matrices with tetrametric ligands, evaluated in columns (0.5M NaOH).

| Ligand | SEQ ID NO. | Ligand content (mg/ml) | Initial IgG capacity Qb10 (mg/ml) | Remaining IgG capacity Qb10 after six 4 h cycles (mg/ml) | Remaining IgG capacity after six 4 h cycles (%) | Capacity retention relative to ref. after six 4 h cycles |
|---|---|---|---|---|---|---|
| Zvar4 | 21 | 7 | 52.5 | 36.5 | 60 | 1 |
| Zvar4 | 21 | 12 | 61.1 | 43.4 | 71 | 1 |
| Zvar(Q9A, N11E, N28A, N43A)4 | 18 | 7.0 | 49.1 | 44.1 | 90 | 1.50 |
| Zvar(Q9A, N11E, N28A, N43A)4 | 18 | 12.1 | 50.0 | 46.2 | 93 | 1.31 |
| Zvar(Q9A, N11E, Q40V, A42K, N43A, L44I)4 | 20 | 7.2 | 49.0 | 44.2 | 90 | 1.50 |
| Zvar(Q9A, N11E, Q40V, A42K, N43A, L44I)4 | 20 | 12.8 | 56.3 | 53.6 | 95 | 1.34 |
| Zvar(N11K, H18K, S33K, D37E, A42R, N43A, L44I, K50R, L51Y)4 | 30 | 9.7 | 56.3 | 52.0 | 92 | 1.53 |
| Zvar(Q9A, N11K, H18K, D37E, A42R)4 | 31 | 10.8 | 56.9 | 52.5 | 92 | 1.30 |

Activation

The base matrix used was rigid cross-linked agarose beads of 85 micrometers (volume-weighted, d50V) median diameter, prepared according to the methods of U.S. Pat. No. 6,602,990, hereby incorporated by reference in its entirety, and with a pore size corresponding to an inverse gel filtration chromatography Kay value of 0.70 for dextran of Mw 110 kDa, according to the methods described in Gel Filtration Principles and Methods, Pharmacia LKB Biotechnology 1991, pp 6-13.

25 mL (g) of drained base matrix, 10.0 mL distilled water and 2.02 g NaOH (s) was mixed in a 100 mL flask with mechanical stirring for 10 min at 25° C. 4.0 mL of epichlorohydrin was added and the reaction progressed for 2 hours. The activated gel was washed with 10 gel sediment volumes (GV) of water.

Coupling

To 20 mL of ligand solution (50 mg/mL) in a 50 ml Falcon tube, 169 mg $NaHCO_3$, 21 mg $Na_2CO_3$, 175 mg NaCl and 7 mg EDTA, was added. The Falcon tube was placed on a roller table for 5-10 min, and then 77 mg of DTE was added. Reduction proceeded for >45 min. The ligand solution was then desalted on a PD10 column packed with Sephadex G-25. The ligand content in the desalted solution was determined by measuring the 276 nm UV absorption.

The activated gel was washed with 3-5 GV 10.1 M phosphate/1 mM EDTA pH 8.61 and the ligand was then coupled according to the method described in U.S. Pat. No. 6,399,750, hereby incorporated by reference in its entirety. All buffers used in the experiments had been degassed by nitrogen gas for at least 5-10 min. The ligand content of the gels could be controlled by varying the amount and concentration of the ligand solution.

After immobilization the gels were washed 3×GV with distilled water. The gels+1 GV 10.1 M phosphate/1 mM EDTA/10% thioglycerol pH 8.61 was mixed and the tubes were left in a shaking table at room temperature overnight. The gels were then washed alternately with 3×GV 10.1 M TRIS/0.15 M NaCl pH 8.61 and 0.5 M HAc and then 8-10×GV with distilled water. Gel samples were sent to an external laboratory for amino acid analysis and the ligand content (mg/ml gel) was calculated from the total amino acid content.

Protein

Gammanorm 165 mg/ml (Octapharma), diluted to 2 mg/ml in Equilibration buffer.

Equilibration Buffer

PBS Phosphate buffer 10 mM+0.14 M NaCl+0.0027 M KCl, pH 7.4 (Medicago)

Adsorption buffer

PBS Phosphate buffer 10 mM+0.14 M NaCl+0.0027 M KCl, pH 7.4 (Medicago)

Elution Buffers 100 mM acetate pH 2.9

Dynamic Binding Capacity 2 ml of resin was packed in TRICORN™ 5 100 columns. The breakthrough capacity was determined with an ÄKTA-Explorer 10 system at a residence time of 6 minutes (0.33 ml/min flow rate). Equilibration buffer was run through the bypass column until a stable baseline was obtained. This was done prior to auto zeroing. Sample was applied to the column until a 100% UV signal was obtained. Then, equilibration buffer was applied again until a stable baseline was obtained.

Sample was loaded onto the column until a UV signal of 85% of maximum absorbance was reached. The column was then washed with 5 column volumes (CV) equilibration buffer at flow rate 0.5 ml/min. The protein was eluted with 5 CV elution buffer at a flow rate of 0.5 ml/min. Then the column was cleaned with 0.5M NaOH at flow rate 0.2 ml/min and re-equilibrated with equilibration buffer.

For calculation of breakthrough capacity at 10%, the equation below was used. That is the amount of IgG that is loaded onto the column until the concentration of IgG in the column effluent is 10% of the IgG concentration in the feed.

$$q_{10\%} = \frac{C_0}{V_C}\left[V_{app} - V_{sys} - \int_{V_{sys}}^{V_{app}} \frac{A(V) - A_{sub}}{A_{100\%} - A_{sub}} * dv \right]$$

$A_{100\%}$=100% UV signal;
$A_{sub}$=absorbance contribution from non-binding IgG subclass;
$A(V)$=absorbance at a given applied volume;
$V_C$=column volume;
$V_{app}$=volume applied until 10% breakthrough;
$V_{sys}$=system dead volume;
$C_0$=feed concentration.

The dynamic binding capacity (DBC) at 10% breakthrough was calculated. The dynamic binding capacity (DBC) was calculated for 10 and 80% breakthrough.

CIP—0.5 M NaOH

The 10% breakthrough DBC (Qb10) was determined both before and after repeated exposures to alkaline cleaning solutions. Each cycle included a CIP step with 0.5 M NaOH pumped through the column at a rate of 0.5/min for 20 min, after which the column was left standing for 4 h. The exposure took place at room temperature (22+/−2° C.). After this incubation, the column was washed with equilibration buffer for 20 min at a flow rate of 0.5 ml/min. Table 4 shows the remaining capacity after six 4 h cycles (i.e. 24 h cumulative exposure time to 0.5 M NaOH), both in absolute numbers and relative to the initial capacity.

Example 5

Figure 4:
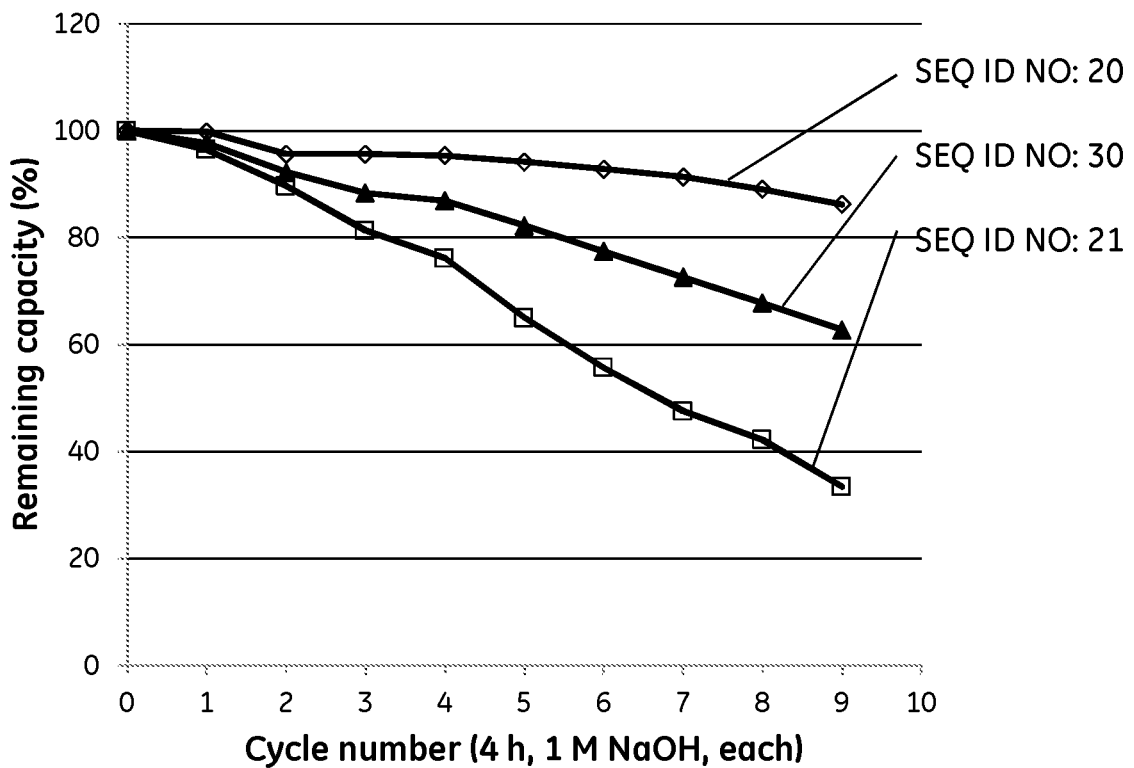
FIG. 4 shows results from Example 4 for the alkali stability (1.0 M NaOH) of parental and mutated tetrameric Zvar (SEQ ID NO:7) polypeptide variants coupled to agarose beads.

Example 4 was repeated with the tetrameric ligands shown in Table 5, but with 1.0 M NaOH used in the CIP steps instead of 0.5 M. The results are shown in Table 5 and in FIG. 4.

TABLE 5

Matrices with tetrametric ligands, evaluated in columns — 1.0M NaOH.

| Ligand | SEQ ID NO. | Ligand content (mg/ml) | Initial IgG capacity Qb10 (mg/ml) | Remaining IgG capacity Qb10 after six 4 h cycles (mg/ml) | Remaining IgG capacity after six 4 h cycles (%) | Capacity retention relative to ref. after six 4 h cycles |
|---|---|---|---|---|---|---|
| Zvar4 | 21 | 12 | 60.1 | 33.5 | 56 | 1 |
| Zvar(Q9A, N11E, Q40V, A42K, N43A, L44I)4 | 20 | 12.8 | 60.3 | 56.0 | 93 | 1.67 |
| Zvar(N11K, H18K, S33K, D37E, A42R, N43A, L44I, K50R, L51Y)4 | 30 | 9.7 | 62.1 | 48.1 | 77 | 1.44 |

Example 6

Base Matrices

The base matrices used were a set of rigid cross-linked agarose bead samples of 59-93 micrometers (volume-weighted, d50V) median diameter (determined on a Malvern Mastersizer 2000 laser diffraction instrument), prepared according to the methods of U.S. Pat. No. 6,602,990 and with a pore size corresponding to an inverse gel filtration chromatography Kd value of 0.62-0.82 for dextran of Mw 110 kDa, according to the methods described above, using HR10/30 columns (GE Healthcare) packed with the prototypes in 0.2 M NaCl and with a range of dextran fractions as probe molecules (flow rate 0.2 ml/min). The dry weight of the bead samples ranged from 53 to 86 mg/ml, as determined by drying 1.0 ml drained filter cake samples at 105° C. over night and weighing.

TABLE 6

Base matrix samples

| Base matrix | Kd | d50v (μm) | Dry weight (mg/ml) |
|---|---|---|---|
| A18 | 0.704 | 59.0 | 56.0 |
| A20 | 0.70 | 69.2 | 55.8 |
| A27 | 0.633 | 87.2 | 74.2 |
| A28 | 0.638 | 67.4 | 70.2 |
| A29 | 0.655 | 92.6 | 57.5 |
| A32 | 0.654 | 73.0 | 70.5 |
| A33 | 0.760 | 73.1 | 55.5 |
| A38 | 0.657 | 70.9 | 56.2 |
| A39 | 0.654 | 66.0 | 79.1 |
| A40 | 0.687 | 64.9 | 74.9 |
| A41 | 0.708 | 81.7 | 67.0 |
| A42 | 0.638 | 88.0 | 59.4 |
| A43 | 0.689 | 87.5 | 77.0 |
| A45 | 0.670 | 56.6 | 66.0 |
| A52 | 0.620 | 53.10 | 63.70 |
| A53 | 0.630 | 52.6 | 86.0 |
| A54 | 0.670 | 61.3 | 75.3 |
| A55 | 0.640 | 62.0 | 69.6 |
| A56 | 0.740 | 61.0 | 56.0 |
| A56-2 | 0.740 | 51.0 | 56.0 |
| A62a | 0.788 | 48.8 | 70.1 |
| A62b | 0.823 | 50.0 | 46.9 |
| A63a | 0.790 | 66.8 | 59.6 |
| A63b | 0.765 | 54.0 | 79.0 |
| A65a | 0.796 | 58.0 | 60.0 |
| A65b | 0.805 | 57.3 | 46.0 |
| B5 | 0.793 | 69.0 | 84.4 |
| C1 | 0.699 | 71.0 | 73.4 |
| C2 | 0.642 | 66.5 | 81.1 |
| C3 | 0.711 | 62.0 | 82.0 |
| C4 | 0.760 | 62.0 | 82.0 |
| H31 | 0.717 | 82.0 | 59.0 |
| H35 | 0.710 | 81.1 | 61.0 |
| H40 | 0.650 | 52.8 | 65.0 |
| I1 | 0.640 | 50.0 | 67.0 |
| 41 | 0.702 | 81.6 | 60.6 |
| 517 | 0.685 | 87.9 | 64.4 |
| 106 | 0.692 | 86.7 | 64.6 |
| 531C | 0.661 | 51.7 | 63.8 |
| P10 | 0.741 | 59.3 | 70.0 |
| S9 | 0.736 | 64.1 | 72.2 |

Coupling 100 ml base matrix was washed with 10 gel volumes distilled water on a glass filter. The gel was weighed (1 g=1 ml) and mixed with 30 ml distilled water and 8.08 g NaOH (0.202 mol) in a 250 ml flask with an agitator. The temperature was adjusted to 27+/−2° C. in a water bath. 16 ml epichlorohydrin (0.202 mol) was added under vigorous agitation (about 250 rpm) during 90+/−10 minutes. The reaction was allowed to continue for another 80+/−10 minutes and the gel was then washed with >10 gel volumes distilled water on a glass filter until neutral pH was reached. This activated gel was used directly for coupling as below.

To 16.4 mL of ligand solution (50 mg/mL) in a 50 ml Falcon tube, 139 mg NaHCO$_3$, 17.4 mg Na$_2$CO$_3$, 143.8 mg NaCl and 141 mg EDTA, was added. The Falcon tube was placed on a roller table for 5-10 min, and then 63 mg of DTE was added. Reduction proceeded for >45 min. The ligand solution was then desalted on a PD10 column packed with Sephadex G-25. The ligand content in the desalted solution was determined by measuring the 276 nm UV absorption.

The activated gel was washed with 3-5 GV 10.1 M phosphate/1 mM EDTA pH 8.61 and the ligand was then coupled according to the method described in U.S. Pat. No. 6,399,750 5.2.2, although with considerably higher ligand amounts (see below). All buffers used in the experiments had been degassed by nitrogen gas for at least 5-10 min. The ligand content of the gels was controlled by varying the amount and concentration of the ligand solution, adding 5-20 mg ligand per ml gel. The ligand was either a tetramer (SEQ ID NO:20) or a hexamer (SEQ ID NO:33) of an alkali-stabilized mutant.

After immobilization the gels were washed 3×GV with distilled water. The gels+1 GV 10.1 M phosphate/1 mM EDTA/10% thioglycerol pH 8.61 was mixed and the tubes were left in a shaking table at room temperature overnight. The gels were then washed alternately with 3×GV 10.1 M TRIS/0.15 M NaCl pH 8.61 and 0.5 M HAc and then 8-10×GV with distilled water. Gel samples were sent to an external laboratory for amino acid analysis and the ligand content (mg/ml gel) was calculated from the total amino acid content.

Evaluation

The Qb10% dynamic capacity for polyclonal human IgG at 2.4 and 6 min residence time was determined as outlined in Example 4.

TABLE 7

Prototype results

| Prototype | Base matrix | Ligand content (mg/ml) | Multimer | Qb10% 2.4 min (mg/ml) | Qb10% 6 min (mg/ml) |
|---|---|---|---|---|---|
| N1 | A38 | 7.45 | tetramer | 44.4 | 58.25 |
| N2 | A20 | 7.3 | tetramer | 45.12 | 57.21 |
| N3 | A42 | 6.72 | tetramer | 33.56 | 50.02 |
| N4 | A29 | 7.3 | tetramer | 36.34 | 51.8 |
| N5 | A28 | 7.9 | tetramer | 42.38 | 58.25 |
| N6 | A39 | 6.96 | tetramer | 41.88 | 54.67 |
| N7 | A27 | 7.5 | tetramer | 29.19 | 48.73 |
| N8 | A43 | 6.99 | tetramer | 33.43 | 49.79 |
| N9 | A38 | 11.34 | tetramer | 48.1 | 72.78 |
| N10 | A20 | 10.6 | tetramer | 50.66 | 70.07 |
| N11 | A42 | 11.1 | tetramer | 32.25 | 57.78 |
| N12 | A29 | 11 | tetramer | 34.85 | 64.68 |
| N13 | A28 | 11.9 | tetramer | 39.92 | 63.75 |
| N14 | A39 | 10.48 | tetramer | 44.37 | 64.79 |
| N15 | A27 | 12.1 | tetramer | 24.8 | 55.56 |
| N16 | A43 | 10.51 | tetramer | 31.82 | 58.04 |
| N17 | A41 | 8.83 | tetramer | 38.5 | 56.8 |
| N18 | A41 | 8.83 | tetramer | 37.84 | 58.6 |
| N19 | A41 | 8.83 | tetramer | 35.06 | 57.23 |
| N20 | A41 | 5.0 | tetramer | 35.64 | 46.04 |
| N21 | A41 | 13.0 | tetramer | 34.95 | 62.23 |
| N22 | A40 | 13.15 | tetramer | 56.85 | 71.09 |
| N23 | A33 | 7.33 | tetramer | 48.69 | 55.76 |
| N24 | A40 | 11.03 | tetramer | 54.96 | 73.8 |
| 033A | A38 | 7.5 | tetramer | 44 | 58 |
| 033B | A38 | 11.3 | tetramer | 48 | 73 |
| 097A | A20 | 7.3 | tetramer | 45 | 57 |
| 097B | A20 | 10.6 | tetramer | 51 | 70 |
| 003A | A28 | 7.9 | tetramer | 42 | 58 |

TABLE 7-continued

Prototype results

| Prototype | Base matrix | Ligand content (mg/ml) | Multimer | Qb10% 2.4 min (mg/ml) | Qb10% 6 min (mg/ml) |
|---|---|---|---|---|---|
| 003B | A28 | 11.9 | tetramer | 40 | 64 |
| 003C | A28 | 15.8 | tetramer | 37 | 67 |
| 038A | A39 | 7.0 | tetramer | 42 | 55 |
| 038B | A39 | 10.5 | tetramer | 44 | 65 |
| 074 | A40 | 13.2 | tetramer | 57 | 71 |
| 093 | A33 | 7.3 | tetramer | 49 | 56 |
| 058A | A40 | 11.0 | tetramer | 55 | 74 |
| 077 | A18 | 8.2 | tetramer | 52 | 59 |
| 010 | A32 | 10.7 | tetramer | 40 | 57 |
| 099 | A32 | 13.3 | tetramer | 37 | 66 |
| 030A | B5 | 6.3 | tetramer | 32 | 38 |
| 030B | B5 | 9.6 | tetramer | 45 | 47 |
| 293A | C1 | 5.4 | tetramer | 38 | 47 |
| 293B | C1 | 10.8 | tetramer | 43 | 60 |
| 294A | C2 | 5.1 | tetramer | 39 | 46 |
| 294B | C2 | 10.5 | tetramer | 42 | 57 |
| 336A | H40 | 5.6 | tetramer | 47 | 52 |
| 336B | H40 | 9.1 | tetramer | 52 | 67 |
| 091 | A18 | 13.4 | tetramer | N/A | 63 |
| 092 | A20 | 12.8 | tetramer | 49 | 67 |
| 080 | A33 | 9.4 | tetramer | 51 | 58 |
| 089 | A40 | 6.1 | tetramer | 49 | 59 |
| 688A | A62a | 6.6 | tetramer | 41 | 46 |
| 688B | A62a | 14.8 | tetramer | 55 | 62 |
| 871 | A62a | 9.7 | tetramer | 48 | 60 |
| 934A | A63a | 6.6 | tetramer | 40 | 44 |
| 934B | A63a | 14.0 | tetramer | 48 | 56 |
| 017B | A65a | 13.1 | tetramer | 56 | 64 |
| 041A | A62b | 5.2 | tetramer | 40 | N/A |
| 041B | A62b | 11.1 | tetramer | 52 | N/A |
| 116A | A65b | 5.8 | tetramer | 42 | 46 |
| 116B | A65b | 8.8 | tetramer | 49 | 56 |
| 017A | A65a | 6.1 | tetramer | 40 | 44 |
| 387A | A62a | 6.4 | tetramer | 43 | 45 |
| 387B | A62a | 7.5 | tetramer | 47 | 56 |
| 432 | A63a | 6.1 | tetramer | 39 | 44 |
| 433A | A65a | 6.6 | tetramer | 42 | 47 |
| 433B | A65a | 13.6 | tetramer | 52 | 61 |
| 579A | I1 | 6.1 | tetramer | 45 | 51 |
| 579B | I1 | 11.2 | tetramer | 57 | 68 |
| 064A | C3 | 5.9 | tetramer | 44 | 52 |
| 064B | C3 | 9.0 | tetramer | 49 | 62 |
| 064C | C3 | 14.3 | tetramer | 51 | 70 |
| 352A | C4 | 10.1 | tetramer | 55 | 63 |
| 352B | C4 | 14.4 | tetramer | 59 | 67 |
| 066A | C3 | 6.8 | hexamer | 48 | 59 |
| 066B | C3 | 11.9 | hexamer | 51 | 73 |
| 066C | C3 | 15.1 | hexamer | 43 | 61 |
| 353A | C4 | 11.2 | hexamer | 62 | 74 |
| 353B | C4 | 15.2 | hexamer | 57 | 82 |
| 872A | A62a | 9.6 | hexamer | 56 | 72 |
| 872B | A62a | 14.5 | hexamer | 62 | 84 |
| 869A | H40 | 6.9 | hexamer | 50 | 56 |
| 869B | H40 | 14.3 | hexamer | 56 | 75 |
| 869C | H40 | 23.0 | hexamer | 41 | 65 |
| 962A | H35 | 6.8 | hexamer | 36 | 49 |
| 962B | H35 | 12.3 | hexamer | 31 | 54 |
| 962C | H35 | 20.3 | hexamer | 20 | 43 |
| 112A | A56 | 7.9 | hexamer | 47 | 55 |
| 112B | A56 | 12.4 | hexamer | 57 | 73 |
| 112C | A56 | 19.2 | hexamer | 55 | 80 |
| 113A | A56 | 7.1 | hexamer | 48 | 57 |
| 113B | A56 | 12.4 | hexamer | 53 | 73 |
| 113C | A56 | 15.2 | hexamer | 48 | 76 |
| 212A | H31 | 6.5 | hexamer | 37 | 38 |
| 212B | H31 | 10.4 | hexamer | 50 | 61 |
| 212C | H31 | 20.0 | hexamer | 31 | 52 |
| 213A | A33 | 6.5 | hexamer | 44 | 53 |
| 213B | A33 | 10.9 | hexamer | 50 | 65 |
| 213C | A33 | 11.1 | hexamer | 50 | 68 |
| 432A | A20 | 6.4 | hexamer | 41 | 56 |
| 432B | A20 | 12.4 | hexamer | 38 | 64 |
| 432C | A20 | 21.1 | hexamer | 44 | 43 |
| 433A | A38 | 5.9 | hexamer | 47 | 57 |

TABLE 7-continued

Prototype results

| Prototype | Base matrix | Ligand content (mg/ml) | Multimer | Qb10% 2.4 min (mg/ml) | Qb10% 6 min (mg/ml) |
|---|---|---|---|---|---|
| 433B | A38 | 11.6 | hexamer | 48 | 72 |
| 433C | A38 | 15.8 | hexamer | 36 | 62 |
| 742A | A54 | 6.7 | hexamer | 38 | 46 |
| 742B | A54 | 12.6 | hexamer | 45 | 52 |
| 742C | A54 | 21.1 | hexamer | 38 | 65 |
| 726A | A63b | 6.4 | hexamer | 42 | 46 |
| 726B | A63b | 10.6 | hexamer | 49 | 60 |
| 726C | A63b | 16.7 | hexamer | 53 | 69 |
| 793A | A56-2 | 6.8 | hexamer | 50 | 58 |
| 793B | A56-2 | 12.5 | hexamer | 59 | 72 |
| 793C | A56-2 | 19.2 | hexamer | 61 | 82 |
| 517 | 517 | 12.0 | tetramer* | 35 | 56 |
| 106 | 106 | 5.8 | tetramer* | 33 | 45 |
| 531C | 531C | 11.2 | tetramer* | 54 | 65 |
| P10 | P10 | 19.0 | hexamer |  | 76 |
| S9 | S9 | 18.4 | hexamer | 56 | 75 |

*SEQ ID NO: 21

Example 7

Figure 5:
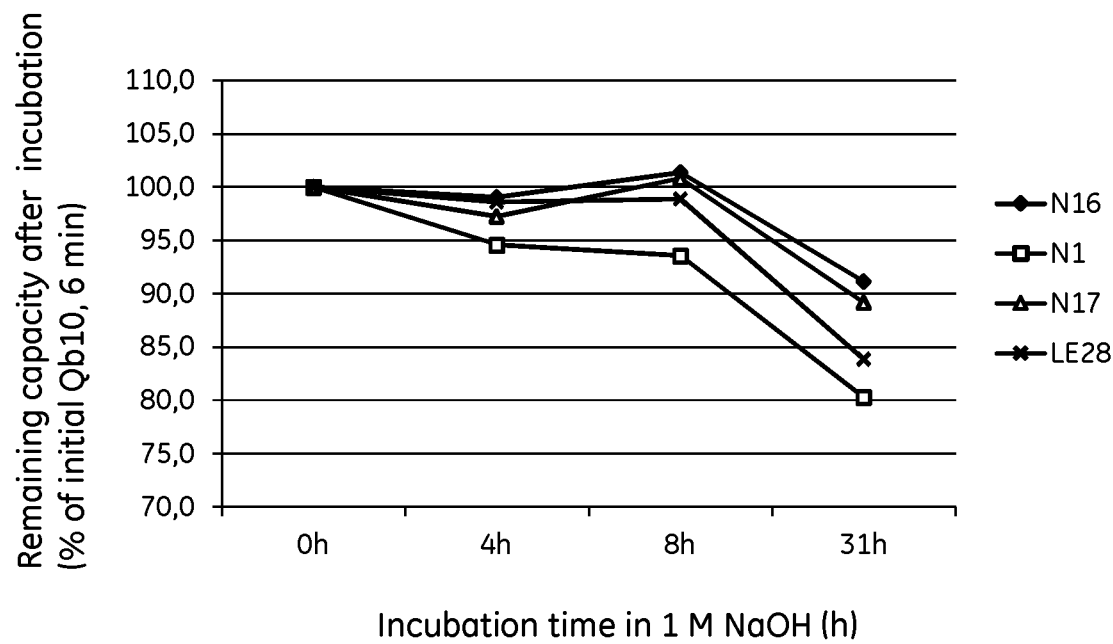
FIG. 5 shows results from Example 7 for the alkali stability (1.0 M NaOH) of agarose beads with different amounts of mutated multimer variants (SEQ ID NO:20) coupled. The results are plotted as the relative remaining dynamic capacity (Qb10%, 6 min residence time) vs. incubation time in 1 M NaOH.
Figure 6:
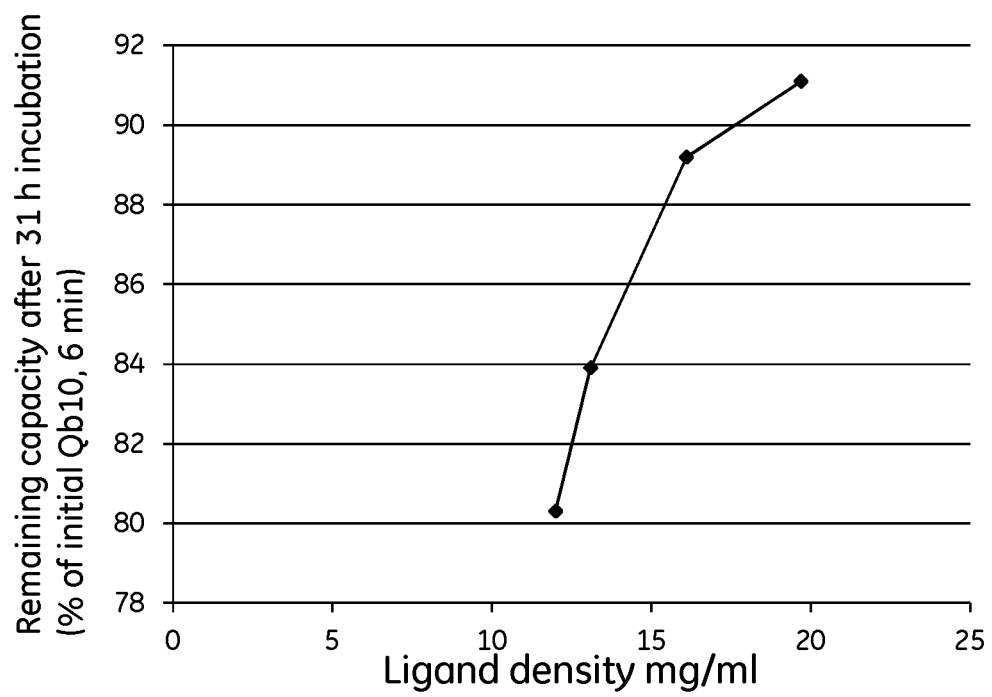
FIG. 6 shows results from Example 7 for the alkali stability (1.0 M NaOH) of agarose beads with different amounts of mutated multimer variants (SEQ ID NO:20) coupled. The results are plotted as the relative remaining dynamic capacity (Qb10%, 6 min residence time) after 31 h incubation in 1 M NaOH vs. the ligand content of the prototypes.

A series of prototypes, prepared as above, with different ligand content (tetramer, SEQ ID NO:20) were incubated in 1 M NaOH for 4, 8 and 31 hours at 22+/−2° C. and the dynamic IgG capacity (Qb10%, 6 min residence time) was measured before and after incubation. The prototypes are shown in Table 8 and the results in FIGS. 5 and 6. It can be seen that the stability towards this harsh alkali treatment increases with increasing ligand content.

TABLE 8

Samples for incubation in 1M NaOH

| Prototype | Ligand content (mg/ml) | Qb10%, 6 min, before incubation (mg/ml) |
|---|---|---|
| N1 | 12 | 78 |
| LE28 | 13 | 79 |
| N17 | 16 | 73 |
| N16 | 20 | 73 |

Example 8

Pressure-Flow Testing of Matrices 300 ml sedimented matrix was packed in a FINELINE 35 column (GE Healthcare Life Sciences, Uppsala, Sweden), with 35 mm inner diameter and 330 mm tube height. The gel was suspended in distilled water to produce a slurry volume of 620 ml and the height of the packed bed was 300+/−10 mm. The packing pressure was 0.10+/−0.02 bar (10+/−2 kPa).

Distilled water was then pumped through the column at increasing pump rates and the flow rate (expressed as the linear flow velocity, cm/h) and back pressure (MPa) was measured after 5 min for each pump setting. The measurements were continued until a max flow rate and a max pressure was reached, i.e. the flow rate and back pressure achieved when the flow rate starts to diminish at increasing back pressures.

TABLE 9

Pressure flow performance of matrices

| Matrix | Max flow velocity, cm/h | Max pressure (MPa) |
|---|---|---|
| 517 | 1343 | 0.56 |
| 106 | 1306 | 0.56 |
| 531C | 513 | 0.51 |
| P10 | 862 | 0.60 |
| S9 | 1172 | 0.64 |

The P10 and S9 matrices have a higher rigidity, as indicated by the max pressure, and can thus sustain comparatively high flow velocities despite their low (59-64 micrometers) median particle diameters.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

ITEMIZED LIST OF EMBODIMENTS i. An Fc-binding polypeptide which comprises a sequence as defined by, or having at least 90% or at least 95% or 98% identity to SEQ ID NO:53.

$X_1$Q $X_2$AFYEIL$X_3$LP NLTEEQR$X_4$$X_5$F I$X_6$$X_7$LKD$X_8$PS$X_9$ S$X_{10}$$X_{11}$$X_{12}$LAEAK$X_{13}$$X_{14}$N$X_{15}$AQ (SEQ ID NO:53)

wherein individually of each other:
$X_1$=A or Q or is deleted
$X_2$=E, K, Y, T, F, L, W, I, M, V, A, H or R
$X_3$=H or K
$X_4$=A or N
$X_5$=A, G, S, Y, Q, T, N, F, L, W, I, M, V, D, E, H, R or K
$X_6$=Q or E
$X_7$=S or K
$X_8$=E or D
$X_9$=Q or V or is deleted
$X_{10}$=K, R or A or is deleted
$X_{11}$=A, E or N or is deleted
$X_{12}$=I or L
$X_{13}$=K or R
$X_{14}$=L or Y
$X_{15}$=D, F, Y, W, K or R ii. The polypeptide of embodiment i, wherein:
$X_1$=A or is deleted, $X_2$=E, $X_3$=H, $X_4$=N, $X_6$=Q, $X_7$=S, $X_8$=D, $X_9$=V or is deleted, $X_{10}$=K or is deleted, $X_{11}$=A or is deleted, $X_{12}$=I, $X_{13}$=K, $X_{14}$=L.

iii. The polypeptide of embodiment i or ii, wherein $X_1$=A, $X_2$=E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=L iv. The polypeptide of embodiment i or ii, wherein $X_1$ is deleted, $X_2$=E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

v. The polypeptide of embodiment i or ii, wherein $X_1$=A, $X_2$=E, $X_3$=H, $X_4$=N, $X_5$=S, Y, Q, T, N, F, L, W, I, M, V, D, E, H, R or K, $X_6$=Q, $X_7$=S, $X_8$=D, $X_9$=V, $X_{10}$=K, $X_1$=A, $X_{12}$=I, $X_{13}$=K, $X_{14}$=L and $X_{15}$=D.

vi. The polypeptide of embodiment i or ii, wherein $X_1$=A, $X_2$=E, $X_3$=H, $X_4$=N, $X_5$=A, $X_6$=Q, $X_7$=S, $X_8$=D, $X_9$ is deleted, $X_{10}$=K, $X_{11}$=A, $X_{12}$=I, $X_{13}$=K, $X_{14}$=L and $X_{15}$=D.

vii. The polypeptide of embodiment i or ii, wherein $X_1$=A, $X_2$=E, $X_3$=H, $X_4$=N, $X_5$=A, $X_6$=Q, $X_7$=S, $X_8$=D, $X_9$=V, $X_{10}$ is deleted, $X_1$=A, $X_{12}$=I, $X_{13}$=K, $X_{14}$=L and $X_{15}$=D.

viii. The polypeptide of embodiment i or ii, wherein $X_1$=A, $X_2$=E, $X_3$=H, $X_4$=N, $X_5$=A, $X_6$=Q, $X_7$=S, $X_8$=D, $X_9$=V, $X_{10}$=K, $X_1$ is deleted, $X_{12}$=I, $X_{13}$=K, $X_{14}$=L and $X_{15}$=D.

ix. The polypeptide of embodiment i or ii, wherein $X_1$=A, $X_2$=E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=F, Y, W, K or R.

x. An Fc-binding polypeptide comprising a mutant of a parental Fc-binding domain of *Staphylococcus* Protein A (SpA), as defined by, or having at least 90% such as at least 95% or 98% identity to, SEQ ID NO: 1, SEQ ID NO: 2, SEQ ID NO:3, SEQ ID NO: 4, SEQ ID NO: 5, SEQ ID NO:6, SEQ ID NO:7, SEQ ID NO:22, SEQ ID NO:51 or SEQ ID NO:52, wherein at least the asparagine or serine residue at the position corresponding to position 11 in SEQ ID NO:4-7 has been mutated to an amino acid selected from the group consisting of glutamic acid, lysine, tyrosine, threonine, phenylalanine, leucine, isoleucine, tryptophan, methionine, valine, alanine, histidine and arginine.

xi. The polypeptide of embodiment x, comprising a mutant of a parental Fc-binding domain of *Staphylococcus* Protein A (SpA), as defined by, or having at least 90% such as at least 95% or 98% identity to, SEQ ID NO:51 or SEQ ID NO:52.

xii. The polypeptide of embodiment x or xi, wherein the amino acid residue at the position corresponding to position 11 in SEQ ID NO:4-7 is a glutamic acid.

xiii. The polypeptide of any one of embodiments x-xii, wherein the amino acid residue at the position corresponding to position 11 in SEQ ID NO:4-7 is a lysine.

xiv. The polypeptide of any one of embodiments x-xiii, wherein the amino acid residue at the position corresponding to position 29 in SEQ ID NO:4-7 is a glycine, serine, tyrosine, glutamine, threonine, asparagine, phenylalanine, leucine, tryptophan, isoleucine, methionine, valine, aspartic acid, glutamic acid, histidine, arginine or lysine.

xv. The polypeptide of any one of embodiments x-xiv, wherein the amino acid residue at the position corresponding to position 9 in SEQ ID NO:4-7 is an alanine.

xvi. The polypeptide of any one of embodiments x-xv, wherein the amino acid residue at the position corresponding to position 9 in SEQ ID NO:4-7 has been deleted.

xvii. The polypeptide of any one of embodiments x-xvi, wherein the amino acid residue at the position corresponding to position 50 in SEQ ID NO:4-7 is an arginine or a glutamic acid, such as an arginine.

xviii. The polypeptide of any one of embodiments x-xvii, wherein the amino acid residue at the position corresponding to position 43 in SEQ ID NO:4-7 has been deleted.

xix. The polypeptide of any one of embodiments x-xviii, wherein the amino acid residue at the position corresponding to position 28 in SEQ ID NO:4-7 is an alanine or an asparagine.

xx. The polypeptide of any one of embodiments x-xix, wherein the amino acid residue at the position corresponding to position 40 in SEQ ID NO:4-7 is selected from the group consisting of asparagine, alanine, glutamic acid and valine.

xxi. The polypeptide of any one of embodiments x-xx, wherein the amino acid residue at the position corresponding to position 40 in SEQ ID NO:4-7 has been deleted.

xxii. The polypeptide according to any one of embodiments x-xxi, wherein the amino acid residue at the position corresponding to position 42 in SEQ ID NO:4-7 is an alanine, lysine or arginine, such as an arginine.

xxiii. The polypeptide according to any one of embodiments x-xxii, wherein the amino acid residue at the position corresponding to position 42 in SEQ ID NO:4-7 has been deleted.

xxiv. The polypeptide according to any one of embodiments x-xxiii, wherein the amino acid residue at the position corresponding to position 44 in SEQ ID NO:4-7 is a leucine or an isoleucine, such as an isoleucine.

xxv. The polypeptide according to any one of embodiments x-xxiv, wherein the amino acid residue at the position corresponding to position 44 in SEQ ID NO:4-7 has been deleted.

xxvi. The polypeptide according to any one of embodiments x-xxv, wherein the amino acid residue at the position corresponding to position 53 in SEQ ID NO:4-7 is a phenylalanine, a tyrosine, a tryptophan, an arginine or a lysine.

xxvii. The polypeptide according to any one of embodiments x-xxvi, wherein the amino acid residue at the position corresponding to position 18 in SEQ ID NO:4-7 is a lysine or a histidine, such as a lysine.

xxviii. The polypeptide according to any one of embodiments x-xxvii, wherein the amino acid residue at the position corresponding to position 33 in SEQ ID NO:4-7 is a lysine or a serine, such as a lysine.

xxix. The polypeptide according to any one of embodiments x-xxviii, wherein the amino acid residue at the position corresponding to position 37 in SEQ ID NO:4-7 is a glutamic acid or an aspartic acid, such as a glutamic acid.

xxx. The polypeptide according to any one of embodiments x-xxix, wherein the amino acid residue at the position corresponding to position 51 in SEQ ID NO:4-7 is a tyrosine or a leucine, such as a tyrosine.

xxxi. The polypeptide according to any one of embodiments x-xxx, wherein one or more of the amino acid residues at the positions corresponding to positions 1, 2, 3, 4, 5, 6, 7, 8, 56, 57 or 58 in SEQ ID NO: 4-7 have been deleted.

xxxii. The polypeptide according to any one of embodiments x-xxxi, wherein the mutation is selected from the group consisting of:

Q9A,N11E,A29G,Q40V,A42K,N43A,L44I;
Q9A,N11E,A29S,Q40V,A42K,N43A,L44I;
Q9A,N11E,A29Y,Q40V,A42K,N43A,L44I;
Q9A,N11E,A29Q,Q40V,A42K,N43A,L44I;
Q9A,N11E,A29T,Q40V,A42K,N43A,L44I;
Q9A,N11E,A29N,Q40V,A42K,N43A,L44I;
Q9A,N11E,A29F,Q40V,A42K,N43A,L44I;
Q9A,N11E,A29L,Q40V,A42K,N43A,L44I;
Q9A,N11E,A29W,Q40V,A42K,N43A,L44I;
Q9A,N11E,A29I,Q40V,A42K,N43A,L44I;
Q9A,N11E,A29M,Q40V,A42K,N43A,L44I;
Q9A,N11E,A29V,Q40V,A42K,N43A,L44I;
Q9A,N11E,A29D,Q40V,A42K,N43A,L44I;
Q9A,N11E,A29E,Q40V,A42K,N43A,L44I;
Q9A,N11E,A29H,Q40V,A42K,N43A,L44I;
Q9A,N11E,A29R,Q40V,A42K,N43A,L44I; and
Q9A,N11E,A29K,Q40V,A42K,N43A,L44I.

xxxiii. The polypeptide according to any one of embodiments x-xxxii, wherein the mutation is selected from the group consisting of:
Q9A,N11E,Q40V,A42K,N43A,L44I,D53F;
Q9A,N11E,Q40V,A42K,N43A,L44I,D53Y;
Q9A,N11E,Q40V,A42K,N43A,L44I,D53W;
Q9A,N11E,Q40V,A42K,N43A,L44I,D53K; and
Q9A,N11E,Q40V,A42K,N43A,L44I,D53R.

xxxiv. The polypeptide according to any one of embodiments x-xxxiii, wherein the mutation is selected from the group consisting of:
Q9del,N11E,Q40V,A42K,N43A,L44I;
Q9A,N11E,Q40del,A42K,N43A,L44I;
Q9A,N11E,Q40V,A42del,N43A,L44I; and
Q9A,N11E,Q40V,A42K,N43del,L44I.

xxxv. The polypeptide according to any one of embodiments x-xxxiv, wherein the mutation is selected from the group consisting of:
D2del,A3del,K4del,Q9A,N11E,Q40V,A42K,N43A,L44I;
V1del,D2del,Q9A,N11E,Q40V,A42K,N43A,L44I, K58del;
V1del,D2del,A3del,Q9A,N11E,Q40V,A42K,N43A,L44I, P57del,K58del;
K4del,F5del,D6del,K7del,E8del,Q9A,N11E,Q40V, A42K,N43A,L44I;
Q9A,N11E,Q40V,A42K,N43A,L44I,A56del,P57del, K58del;
V1del,D2del,A3del,Q9A,N11E,Q40V,A42K,N43A,L44I;
V1del,D2del,A3del,K4del,F5del,D6del,K7del,E8del, Q9A,N11E,Q40V,A42K,N43A,L44I; and
Q9A,N11E,Q40V,A42K,N43A,L44I,K58_insYEDG.

xxxvi. The polypeptide according to any one of embodiments i-xxxi, comprising or consisting essentially of a sequence having at least 90% identity to an amino acid sequence selected from the group consisting of: SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69 and SEQ ID NO:70.

xxxvii. The polypeptide according to any one of embodiments i-xxxi, comprising or consisting essentially of a sequence having at least 90% identity to an amino acid sequence selected from the group consisting of: SEQ ID NO:71, SEQ ID NO:72, SEQ ID NO:73, SEQ ID NO:74 and SEQ ID NO:75.

xxxviii. The polypeptide according to any one of embodiments i-xxxi, comprising or consisting essentially of a sequence having at least 90% identity to an amino acid sequence selected from the group consisting of: SEQ ID NO:76, SEQ ID NO:77, SEQ ID NO:78 and SEQ ID NO:79.

xxxix. The polypeptide according to any one of embodiments i-xxxi, comprising or consisting essentially of a sequence having at least 90% identity to an amino acid sequence selected from the group consisting of: SEQ ID NO:89, SEQ ID NO:90, SEQ ID NO:91, SEQ ID NO:92, SEQ ID NO:93, SEQ ID NO:94 and SEQ ID NO:95.

xl. The polypeptide according to any preceding embodiment, which polypeptide has an improved alkaline stability compared to a polypeptide as defined by SEQ ID NO:1, SEQ ID NO:2, SEQ ID NO:3, SEQ ID NO:4, SEQ ID NO:5, SEQ ID NO:6 or SEQ ID NO:7, such as by SEQ ID NO:7.

xli. The polypeptide according to any preceding embodiment, which polypeptide has an improved alkaline stability compared to a parental polypeptide as defined by SEQ ID NO:1, SEQ ID NO:2, SEQ ID NO:3, SEQ ID NO:4, SEQ ID NO:5, SEQ ID NO:6 or SEQ ID NO:7, such as by SEQ ID NO:7.

xlii. The polypeptide according to embodiment xl or xli, wherein the alkaline stability is improved as measured by the remaining IgG-binding capacity, after 24, 25 h incubation in 0.5 M or 1.0 M aqueous NaOH at 22+/−2° C.

xliii. A multimer comprising or consisting essentially of a plurality of polypeptides as defined by any preceding embodiment.

xliv. The multimer according to embodiment xliii, wherein the polypeptides are linked by linkers comprising up to 25 amino acids, such as 3-25 or 3-20 amino acids.

xlv. The multimer of embodiment xliii or xliv, wherein at least two polypeptides are linked by linkers comprising or consisting essentially of a sequence having at least 90% identity with an amino acid sequence selected from the group consisting of APKVDAKFDKE (SEQ ID NO:96), APKVDNKFNKE (SEQ ID NO:97), APKADNKFNKE (SEQ ID NO:98), APKVFDKE (SEQ ID NO:99), APAKFDKE (SEQ ID NO:100), AKFDKE (SEQ ID NO:101), APKVDA (SEQ ID NO:102), VDAKFDKE (SEQ ID NO:103), APKKFDKE (SEQ ID NO:104), APK, APKYEDGVDAKFDKE (SEQ ID NO:105) and YEDG (SEQ ID NO:106).

xlvi. The multimer according to embodiment xliv or xlv, which is a dimer, trimer, tetramer, pentamer, hexamer, heptamer, octamer or nonamer.

xlvii. The multimer according to any one of embodiments xliv-xlvi, which comprises or consists essentially of a sequence selected from the group of sequences defined by SEQ ID NO:80, SEQ ID NO:81, SEQ ID NO:82, SEQ ID NO:83, SEQ ID NO:84, SEQ ID NO:85, SEQ ID NO:86 and SEQ ID NO:87.

xlviii. The polypeptide or multimer according to any preceding embodiment, further comprising at, or within 1-5 amino acid residues from, the C-terminal or N-terminal one or more coupling element, selected from the group consisting of one or more cysteine residues, a plurality of lysine residues and a plurality of histidine residues.

xlix. A nucleic acid or a vector encoding a polypeptide or multimer according to any preceding embodiment.

l. An expression system, which comprises a nucleic acid or vector according to embodiment xlix.

li. A separation matrix, wherein a plurality of polypeptides or multimers according to any one of embodiment i-xlviii have been coupled to a solid support.

lii. A separation matrix comprising at least 11 mg/ml Fc-binding ligands covalently coupled to a porous support, wherein:
  a) said ligands comprise multimers of alkali-stabilized Protein A domains,
  b) said porous support comprises cross-linked polymer particles having a volume-weighted median diameter (d50,v) of 55-70 micrometers and a dry solids weight of 55-80 mg/ml.

liii. A separation matrix comprising at least 15, such as 15-21 or 15-18 mg/ml Fc-binding ligands covalently coupled to a porous support, wherein said ligands comprise multimers of alkali-stabilized Protein A domains.

liv. The separation matrix of embodiment li or liii, wherein said cross-linked polymer particles comprise cross-linked polysaccharide particles.

lv. The separation matrix of any one of embodiments li-liv, wherein said cross-linked polymer particles comprise cross-linked agarose particles.

lvi. The separation matrix of any one of embodiments li-lv, wherein said cross-linked polymer particles have a pore size corresponding to an inverse gel filtration chromatography Kd value of 0.70-0.85 for dextran of Mw 110 kDa.

lvii. The separation matrix of any one of embodiments li-lvi, which has a max pressure of at least 0.58, such as at least 0.60, MPa when packed at 300+/−10 mm bed height in a FINELINE 35 column.

lviii. The separation matrix of any one of embodiments li-lvii, wherein said multimers comprise tetramers, pentamers, hexamers or heptamers of alkali-stabilized Protein A domains.

lix. The separation matrix of any one of embodiments li-lviii, wherein said multimers comprise hexamers of alkali-stabilized Protein A domains.

lx. The separation matrix of any one of embodiments li-lix, wherein the polypeptides are linked by linkers comprising up to 25 amino acids, such as 3-25 or 3-20 amino acids.

lxi. The separation matrix of any one of embodiments li-lx, wherein at least two polypeptides are linked by linkers comprising or consisting essentially of a sequence having at least 90% identity with an amino acid sequence selected from the group consisting of APKVDAKFDKE (SEQ ID NO:96), APKVDNKFNKE (SEQ ID NO:97), APKADNKFNKE (SEQ ID NO:98), APKVFDKE (SEQ ID NO:99), APAKFDKE (SEQ ID NO:100), AKFDKE (SEQ ID NO:101), APKVDA (SEQ ID NO:102), VDAKFDKE (SEQ ID NO:103), APKKFDKE (SEQ ID NO:104), APK, APKYEDGVDAKFDKE (SEQ ID NO:105) and YEDG (SEQ ID NO:106).

lxii. The separation matrix of any one of embodiments li-lxi, having a 10% breakthrough dynamic binding capacity for IgG of at least 45 mg/ml, such as at least 50 or at least 55 mg/ml mg/ml at 2.4 min residence time.

lxiii. The separation matrix of any one of embodiments li-lxii, having a 10% breakthrough dynamic binding capacity for IgG of at least 60 mg/ml, such as at least 65, at least 70 or at least 75 mg/ml at 6 min residence time.

lxiv. The separation matrix of any one of embodiments li-lxiii, wherein the 10% breakthrough dynamic binding capacity for IgG at 2.4 or 6 min residence time is reduced by less than 20% after incubation 31 h in 1.0 M aqueous NaOH at 22+/−2 C.

lxv. The separation matrix of any one of embodiments li-lxiv, having a dissociation constant for IgG2 of below 0.2 mg/ml, such as below 0.1 mg/ml, in 20 mM phosphate buffer, 180 mM NaCl, pH 7.5.

lxvi. The separation matrix according to any one of embodiments li-lxv, wherein the polypeptides or multimers have been coupled to the solid support or porous support via thioether bonds.

lxvii. The separation matrix according to any one of embodiments li-lxvi, wherein the solid support or porous support is a polysaccharide.

lxviii. The separation matrix according to any one of embodiments li-lxvii, wherein the IgG capacity of the matrix after 24 incubation in 0.5 M NaOH at 22+/−2° C. is at least 80, such as at least 85, at least 90 or at least 95% of the IgG capacity before the incubation.

lxix. The separation matrix according to any one of embodiments li-lxviii, wherein the IgG capacity of the matrix after 24 incubation in 1.0 M NaOH at 22+/−2° C. is at least 70, such as at least 80 or at least 90% of the IgG capacity before the incubation.

lxx. The separation matrix of any one of embodiments li-lxix, wherein said alkali-stabilized Protein A domains or plurality of polypeptides/multimers comprise(s) mutants of a parental Fc-binding domain of Staphylococcus Protein A (SpA), as defined by, or having at least 80% such as at least 90%, 95% or 98% identity to, SEQ ID NO: 1, SEQ ID NO: 2, SEQ ID NO:3, SEQ ID NO: 4, SEQ ID NO: 5, SEQ ID NO:6, SEQ ID NO:7, SEQ ID NO:22, SEQ ID NO:51 or SEQ ID NO:52, wherein at least the asparagine or serine residue at the position corresponding to position 11 in SEQ ID NO:4-7 has been mutated to an amino acid selected from the group consisting of glutamic acid, lysine, tyrosine, threonine, phenylalanine, leucine, isoleucine, tryptophan, methionine, valine, alanine, histidine and arginine.

lxxi. The separation matrix of embodiment lxx, wherein the amino acid residue at the position corresponding to position 11 in SEQ ID NO:4-7 is, or has been mutated to, a glutamic acid or a lysine.

lxxii. The separation matrix of embodiment lxx or lxxi, wherein the amino acid residue at the position corresponding to position 40 in SEQ ID NO:4-7 is, or has been mutated to, a valine.

lxxiii. The separation matrix of any one of embodiments li-lxix, wherein said alkali-stabilized Protein A domains or plurality of polypeptides/multimers comprise(s) an Fc-binding polypeptide having an amino acid sequence as defined by, or having at least 80%, such as at least 90, 95 or 98%, identity to SEQ ID NO:53.

$X_1Q \quad X_2AFYEILX_3LP \quad NLTEEQRX_4X_5F$
$IX_6X_7LKDX_8PSX_9$
$SX_{10}X_{11}X_{12}LAEAKX_{13}X_{14}NX_{15}AQ$ (SEQ ID NO:53)

wherein individually of each other:
$X_1$=A or Q or is deleted
$X_2$=E, K, Y, T, F, L, W, I, M, V, A, H or R
$X_3$=H or K
$X_4$=A or N
$X_5$=A, G, S, Y, Q, T, N, F, L, W, I, M, V, D, E, H, R or K
$X_6$=Q or E
$X_7$=S or K
$X_8$=E or D
$X_9$=Q or V or is deleted
$X_{10}$=K, R or A or is deleted
$X_{11}$=A, E or N or is deleted
$X_{12}$=J or L
$X_{13}$=K or R
$X_{14}$=L or Y
$X_{15}$=D, F, Y, W, K or R lxxiv. The separation matrix of embodiment lxxiiii, wherein individually of each other: $X_1$=A or is deleted, $X_2$=E, $X_3$=H, $X_4$=N, $X_6$=Q, $X_7$=S, $X_8$=D, $X_9$=V or is deleted, $X_{10}$=K or is deleted, $X_{11}$=A or is deleted, $X_{12}$=I, $X_{13}$=K, $X_{14}$=L.

lxxv. The separation matrix of embodiment lxxiii, wherein individually of each other: $X_1$=A, $X_2$=E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

lxxvi. The separation matrix of embodiment lxxiii, wherein individually of each other: wherein $X_1$ is A, $X_2$=E, $X_3$=H, $X_4$=N, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

lxxvii. The separation matrix of embodiment lxxiii, wherein individually of each other: wherein X is A, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

lxxviii. The separation matrix according to any one of embodiments li-lxxvii, wherein said multimers or polypeptides further comprise at, or within 1-5 amino acid residues from, the C-terminal or N-terminal one or more coupling element, selected from the group consisting of one or more cysteine residues, a plurality of lysine residues and a plurality of histidine residues.

lxxix. The separation matrix according to any one of embodiments li-lxxviii wherein said multimers or polypeptides further comprise at the N-terminal a leader sequence, comprising 1-20 amino acid residues.

lxxx. A method of isolating an immunoglobulin, wherein a separation matrix according to any one of embodiments li-lxxix is used.

lxxxi. The method of embodiment lxxx, comprising the steps of:
a) contacting a liquid sample comprising an immunoglobulin with a separation matrix according to any one of embodiments li-lxxix,
b) washing said separation matrix with a washing liquid,
c) eluting the immunoglobulin from the separation matrix with an elution liquid, and
d) cleaning the separation matrix with a cleaning liquid.

lxxxii. The method of embodiment lxxxi, wherein the cleaning liquid is alkaline, such as with a pH of 13-14.

lxxxiii. The method of embodiment lxxxi or lxxxii, wherein the cleaning liquid comprises 0.1-1.0 M NaOH or KOH, such as 0.5-1.0 M or 0.4-1.0 M NaOH or KOH.

lxxxiv. The method of any one of embodiments lxxxi-lxxxiii, wherein steps a)-d) are repeated at least 10 times, such as at least 50 times or 50-200 times.

lxxxv. The method of any one of embodiments lxxxi-lxxxiv, wherein steps a)-c) are repeated at least 10 times, such as at least 50 times or 50-200 times and wherein step d) is performed after a plurality of instances of step c), such as at least 10 or at least 50 times.

The invention claimed is:

1. A separation matrix comprising at least 15 mg/ml Fc-binding ligands covalently coupled to a porous support, wherein:

the ligands comprise multimers of alkali-stabilized Protein A domains;

the porous support comprises cross-linked polymer particles having a volume-weighted median diameter (d50, v) of from 56 μm to 70 μm;

the separation matrix has a max pressure of at least 0.58 MPa when packed at 300+/−10 mm bed height in a 35 mm separation column; and the Protein A domains comprise an Fc-binding polypeptide defined by, or having at least 80% identity to SEQ ID NO: 53 and $X_1QX_2AFYEILX_3LPNLTEEQRX_4X_5FIX_6X_7 LKDX_8PSX_9SX_{10}X_{11}X_{12}LAEAKX_{13}X_{14}N\ X_{15}AQ$ (SEQ ID NO: 53), wherein individually of each other:

$X_1$=A or Q or is deleted;
$X_2$=E, K, Y, T, F, L, W, I, M, V, A, H, or R;
$X_3$=H or K;
$X_4$=A or N;
$X_5$=A, G, S, Y, Q, T, N, F, L, W, I, M, V, D, E, H, R, or K;
$X_6$=Q or E;
$X_7$=S or K;
$X_8$=E or D;
$X_9$=W or V or is deleted;
$X_{10}$=K, R, or A, or is deleted;
$X_{11}$=A, E, or N, or is deleted;
$X_{12}$=I or L;
$X_{13}$=K or R;
$X_{14}$=L or Y; and
$X_{15}$=D, F, Y, W, K, or R.

2. The separation matrix of claim 1, wherein the cross-linked polymer particles have a dry solids weight of from 55 mg/ml to 80 mg/ml.

3. The separation matrix of claim 1, wherein the cross-linked polymer particles have a dry solids weight of from 60 mg/ml to 78 mg/ml.

4. The separation matrix of claim 1, wherein the cross-linked polymer particles have a dry solids weight of from 65 mg/ml to 78 mg/ml.

5. The separation matrix of claim 1, wherein the cross-linked polymer particles have a volume-weighted median diameter (d50,v) of from 56 μm to 66 μm.

6. The separation matrix of claim 1, wherein the cross-linked polymer particles comprise cross-liked polysaccharide particles.

7. The separation matrix of claim 1, wherein the cross-linked polymer particles comprise cross-linked agarose particles.

8. The separation matrix of claim 1, wherein the cross-linked polymer particles have a pore size corresponding to an inverse gel filtration chromatography Kd value of 0.69-0.85 for dextran of Mx 100 kDa.

9. The separation matrix of claim 1, wherein the multimers comprise tetramers, pentamers, hexamers, or heptamers of alkali-stabilized Protein A domains.

10. The separation matrix of claim 1, wherein the multimers comprise hexamers of alkali-stabilized Protein A domains.

11. The separation matrix of claim 1, having a 10% breakthrough dynamic binding capacity for IgG of at least 45 mg/ml at 2.4 minutes residence time.

12. The separation matrix of claim 1, having a 10% breakthrough dynamic binding capacity for IgG of at least 50 mg/ml at 2.4 minutes residence time.

13. The separation matrix of claim 1, having a 10% breakthrough dynamic binding capacity for IgG of at least 55 mg/ml at 2.4 minutes residence time.

14. The separation matrix of claim 1, having a 10% breakthrough dynamic binding capacity for IgG of at least 60 mg/ml at 6 minutes residence time.

15. The separation matrix of claim 1, having a 10% breakthrough dynamic binding capacity for IgG of at least 65 mg/ml at 6 minutes residence time.

16. The separation matrix of claim 1, having a 10% breakthrough dynamic binding capacity for IgG of at least 70 mg/ml at 6 minutes residence time.

17. The separation matrix of claim 1, having a 10% breakthrough dynamic binding capacity for IgG of at least 75 mg/ml at 6 minutes residence time.

18. The separation matrix of claim 11, wherein the 10% breakthrough dynamic binding capacity for IgG at 2.4 minutes residence time is reduced by less than 20% after incubation for 31 hours in 1.0 M aqueous NaOH at 22+/−2° C.

19. The separation matrix of claim 1, having a dissociation constant for IgG2 of below 0.2 mg/ml in 20 mM phosphate buffer, 180 mM NaCl, pH 7.5.

20. The separation matrix of claim 1, having a dissociation constant for IgG2 of below 0.1 mg/ml in 20 mM phosphate buffer, 180 mM NaCl, pH 7.5.

21. The separation matrix of claim 1, wherein individually of each other:
$X_1$=A or is deleted;
$X_2$=E;
$X_3$=H;
$X_4$=N;
$X_6$=Q;
$X_7$=S;
$X_8$=D;
$X_9$=V or is deleted;
$X_{10}$=K or is deleted;
$X_{11}$=A or is deleted;
$X_{12}$=I;
$X_{13}$=K; and
$X_{14}$=L.

22. The separation matrix of claim 1, wherein the amino acid sequence has at least 90% identity to SEQ ID NO: 53.

23. The separation matrix of claim 1, wherein the amino acid sequence has at least 95% identity to SEQ ID NO: 53.

24. The separation matrix of claim 1, wherein the amino acid sequence has at least a 98% identity to SEQ ID NO: 53.

25. The separation matrix of claim 1, wherein the amino acid sequence is identical to SEQ ID NO: 53.

26. The separation matrix of claim 1, wherein the polypeptides are linked by linkers comprising up to 25 amino acids.

27. The separation matrix of claim 1, wherein at least two polypeptides are linked by likers comprising or consisting essentially of a sequence having at least 90% identity with an amino acid sequence selected from the group consisting of APKVDAKFDKE (SEQ ID NO: 96), APKVDNKFNKE (SEQ ID NO: 97), APKADNKFNKE (SEQ ID NO: 98), APKVFDKE (SEQ ID NO: 99), APAKFDKE (SEQ ID NO: 100), AKFDKE (SEQ ID NO: 101), APKVDA (SEQ ID NO: 102), VDAKFDKE (SEQ ID NO: 103), APKKFDKE (SEQ ID NO: 104), APK, APKYEDGVDAKFDKE (SEQ ID NO: 105), and YEDG (SEQ ID NO: 106).

28. The separation matrix of claim 1, comprising from 15 mg/ml to 21 mg/ml Fc-binding ligands covalently coupled to the porous support.

29. The separation matrix of claim 1, comprising from 17 mg/ml to 21 mg/ml Fc-biding ligands covalently coupled to the porous support.

30. The separation matrix of claim 1, comprising from 18 mg/ml to 20 mg/ml Fc-binding ligands covalently coupled to the porous support.

31. A method of isolating an immunoglobulin, comprising the steps of:
a) contacting an immunoglobulin with a separation matrix according to claim 1;
b) washing the separation matrix with a washing liquid;
c) eluting the immunoglobulin from the separation matrix with an elution liquid; and
d) cleaning the separation matrix with a cleaning liquid.

32. The method of claim 31, wherein the cleaning liquid comprises from 0.1 to 1.0 M NaOH or KOH.

33. The method of claim 32, wherein steps a)-d) are repeated at least 10 times.

34. The method of claim 32, wherein in step c) the elution liquid has a pH of from 2.5 to 4.5.

35. The method of claim 32, wherein in step b) the washing liquid has a pH of from 6 to 8.

36. The method of claim 32, wherein in step b) residence time of the liquid on the separation matrix is from 2 minutes to 20 minutes.

37. The method of claim 32, wherein the cleaning liquid comprises at least 0.5 M NaOH.

38. The method of claim 33, wherein in step d) contact time between the separation matrix and the cleaning liquid is less than 10 minutes.

* * * * *